(12) United States Patent
Shin et al.

(10) Patent No.: US 8,525,158 B2
(45) Date of Patent: Sep. 3, 2013

(54) ANTHRACENE DERIVATIVE AND ORGANIC ELECTROLUMINESCENCE ELEMENT USING THE SAME

(75) Inventors: Chang-Ju Shin, Gyeonggi-do (KR); Tae-Hyung Kim, Gyeonggi-do (KR); Kyoung-Soo Kim, Daejeon (KR); Jung-Sub Lee, Gyeonggi-do (KR)

(73) Assignee: Doosan Corporation (KR)

( * ) Notice: Subject to any disclaimer, the term of this patent is extended or adjusted under 35 U.S.C. 154(b) by 235 days.

(21) Appl. No.: 13/061,730

(22) PCT Filed: Sep. 1, 2009

(86) PCT No.: PCT/KR2009/004917
§ 371 (c)(1),
(2), (4) Date: May 19, 2011

(87) PCT Pub. No.: WO2010/027181
PCT Pub. Date: Mar. 11, 2010

(65) Prior Publication Data
US 2011/0210320 A1    Sep. 1, 2011

(30) Foreign Application Priority Data

Sep. 2, 2008  (KR) .................. 10-2008-0086113
Jun. 22, 2009  (KR) .................. 10-2009-0055440

(51) Int. Cl.
*H01L 35/24* (2006.01)
(52) U.S. Cl.
USPC .................. 257/40; 257/E51.001

(58) Field of Classification Search
USPC ............................................ 257/40, E51.001
See application file for complete search history.

(56) References Cited

FOREIGN PATENT DOCUMENTS

| JP | 2004-2351 A | 1/2004 |
|---|---|---|
| JP | 2005-47868 A | 2/2005 |
| JP | 2006-176448 A | 7/2006 |
| JP | 2012510988 | 5/2012 |

OTHER PUBLICATIONS

International Search Report for International Application No. PCT/KR2009/004917 dated Apr. 15, 2010 with English translation.

*Primary Examiner* — Anthony Ho
(74) *Attorney, Agent, or Firm* — Cantor Colburn LLP

(57) ABSTRACT

The present invention relates to an anthracene derivative and an organic electroluminescent device using the same. More specifically, the present invention relates to: a novel compound which has a core (for example, an indenoanthracene core) where both an anthracene moiety with excellent device characteristics and a fluorene moiety with excellent fluorescent properties are fused, wherein substituents (for example, a heterocyclic group such as a benzimidazole group, a benzothiazole group, a benzoxazole group, a pyridinyl group or a bipyridinyl group) with an electron transfer capacity are substituted to the core; and an organic electroluminescence element which has improved luminous efficiency, brightness, thermal stability, driving voltage, and lifetime, by comprising an organic layer which is positioned between a positive electrode and negative electrode and contains the novel compound.

6 Claims, No Drawings

ANTHRACENE DERIVATIVE AND ORGANIC ELECTROLUMINESCENCE ELEMENT USING THE SAME

This is a U.S. national stage application of International Application No. PCT/KR2009/004917, filed on Sep. 1, 2009. Priority under 35 U.S.C. 119(a) and 35 U.S.C. 365(b) is claimed from Korean Application Nos. 10-2008-0086113, filed Sep. 2, 2008, and 10-2009-0055440, filed Jun. 22, 2009 the disclosure of each of which are also incorporated herein by reference.

TECHNICAL FIELD

The present invention relates to a novel anthracene derivative and an organic electroluminescent device using the same. More particularly, the present invention relates to a novel compound having a core where an anthracene moiety with excellent device characteristics is fused with a fluorene moiety or the like with excellent fluorescent properties, wherein a substituent having an electron transport capability is substituted for the core; and an organic electroluminescent device including an organic material layer containing the novel compound, the organic material layer being intervened between an anode and a cathode, which is enhanced in luminous efficiency, luminance, thermal stability, driving voltage, lifetime, etc.

BACKGROUND ART

Generally, an organic light-emitting phenomenon refers to the conversion of an electrical energy to light energy using an organic material. In other words, in a case where an organic material layer is positioned between a positive electrode (e.g. an anode) and a negative electrode (e.g. a cathode), when a voltage is applied between the two electrodes, holes from the anode and electrons from the cathode are injected into the organic material layer. When the injected holes combine with the injected electrons, excitons are formed. Then, when the excitons return to a ground state, light is generated.

For research on such an organic electroluminescent device, Bernanose in the 1950's applied a high AC voltage to a polymer thin film containing organic dye, and observed light emission from the organic thin film. Then, in 1965, he generated singlet excitons by applying current to anthracene single crystal, and thus obtained blue fluorescence.

As one method for efficiently fabricating an organic electroluminescent device, a research for fabricating an organic material layer in a multi-layer structure, instead of in a single layer structure, within the device, has been conducted. In 1987, Tang reported an organic electroluminescent device with a layered structure including function layers such as a hole layer and a light emitting layer. Most of currently used organic electroluminescent devices include a substrate, an anode, a hole injection layer receiving holes from the anode, a hole transport layer transporting holes, a light emitting layer emitting light through recombination of holes and electrons, an electron transport layer transporting electrons, an electron injection layer receiving electrons from a cathode, and the cathode. The reason the organic electroluminescent device is manufactured in a multi-layered structure is that a hole and an electron have different moving speeds. Thus, when hole injection/transport layers, and electron injection/transport layers are appropriately formed, holes and electrons can be effectively transported. This balances holes and electrons within a device, thereby increasing luminous efficiency.

The first report on a material for electron transport was on an oxadiazole derivative (PBD). Then, a triazole derivative (TAZ) and a phenanthroline derivative (BCP) were reported to show an electron transport capability. Also, it was reported that as an electron transport layer, organic metal complexes from among organic monomolecular materials, which have a high stability against electrons and showing a relatively high electron moving speed, are preferable. Especially, Alq3 having a high stability and a high electron affinity was reported to be the most excellent, and is currently generally used. Also, there are conventionally known electron transport materials such as a flavon derivative (Sanyo), or germanium and silicon cyclopentadienone derivatives (Chisso) (Japanese Patent Publication Nos. 1998-017860, and 1999-087067).

Also, as materials for electron injection/transport layers, organic monomolecular materials having an imidazole group, an oxazole group, and a thiazole group have conventionally frequently been reported. However, before these materials were reported as the electron transport materials, the application of the materials' metal complex compounds to a blue light emitting layer or a blue-green light emitting layer of an organic light emitting device had been already reported in EU 0700917 A2 (Motorola).

TPBI, which was reported from Kodak in 1996 and disclosed in U.S. Pat. No. 5,645,948, is known to be a representative electron transport layer material having an imidazole group. Structurally, it contains three N-phenyl benzimidazole groups at 1,3,5 substitution positions of benzene. Also, functionally, it can not only transport electrons but also block holes from a light emitting layer. However, there is a problem in that TPBI has a low thermal stability for actual application to a device.

Also, there are other electron transport materials disclosed in Japanese Patent Publication Hei 11-345686, which were reported to contain an oxazole group, and a thiazole group, and to be capable of being applied to a light emitting layer. However, they are not yet put to practical use in view of driving voltage, luminance, and device lifetime.

Accordingly, in order to overcome the above described problems of a conventional technology, and to further improve the characteristics of an organic electroluminescent device, it is continuously required to develop a more stable and more efficient material capable of being used as an electron transport material in the organic electroluminescent device.

DISCLOSURE

Technical Problem

In view of the above problems, the present invention provides a novel compound applicable to an organic electroluminescent device. Also, the present invention provides an organic electroluminescent device including the novel compound, which requires a low driving voltage, and is enhanced in luminous efficiency, luminance, thermal stability, and lifetime, etc.

Technical Solution

The present invention provides a compound represented by Formula 1 below.

[Formula 1]

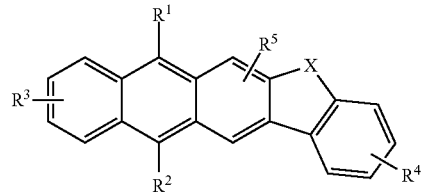

In Formula 1, X is selected from the group consisting of $CR^6R^7$, $NR^6$, O, S, $S(=O)$, $S(=O)_2$ and $SiR^6R^7$; and $R^1$ through $R^7$ are the same or different and each independently selected from the group consisting of hydrogen (H), deuterium (D), an alkyl group of $C_1$~$C_{40}$, an alkenyl group of $C_2$~$C_{40}$, an alkynyl group of $C_2$~$C_{40}$, a cycloalkyl group of $C_3$~$C_{40}$, a heterocycloalkyl group of $C_3$~$C_{40}$, an arylalkyl group of $C_6$~$C_{40}$, an alkyloxy group of $C_1$~$C_{40}$, an aryloxy group of $C_5$~$C_{40}$, an aryl group of $C_5$~$C_{40}$, a heteroaryl group of $C_5$~$C_{40}$, a substituent represented by Formula 2 below, and a substituent represented by Formula 3 below.

Herein, at least one of $R^1$ through $R^4$ is a substituent represented by Formula 2, or a substituent represented by Formula 3.

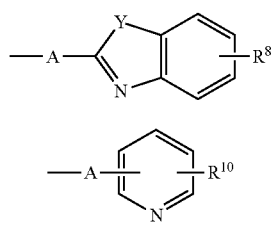

[Formula 2]

[Formula 3]

In Formulas 2 and 3, Y is selected from the group including N—$R^9$, S, and O;

$R^8$ through $R^{10}$ are the same or different and each independently selected from the group consisting of hydrogen (H), deuterium (D), an alkyl group of $C_1$~$C_{40}$, an alkenyl group of $C_2$~$C_{40}$, an alkynyl group of $C_2$~$C_{40}$, a cycloalkyl group of $C_3$~$C_{40}$, a heterocycloalkyl group of $C_3$~$C_{40}$, an arylalkyl group of $C_6$~$C_{40}$, an alkyloxy group of $C_1$~$C_{40}$, an aryloxy group of $C_5$~$C_{40}$, an aryl group of $C_5$~$C_{40}$, and a heteroaryl group of $C_5$~$C_{40}$; and A represents a single bond, an arylene group of $C_5$~$C_{40}$, or a heteroarylene group of $C_5$~$C_{40}$.

Also, the present invention provides an organic electroluminescent device including an anode, a cathode, and one or more organic material layers intervened between the anode and the cathode, wherein at least one layer of the organic material layers includes the compound represented by Formula 1 according to the present invention. In the present invention, the organic material layer including the compound represented by Formula 1 is preferably an electron transport layer.

Advantageous Effects

The inventive compound represented by Formula 1 shows a high electron transport capability. Thus, an organic light emitting device employing the compound as a material for an electron transport layer can show a higher performance as compared to a conventional device employing Alq3, in view of voltage and efficiency. Accordingly, the inventive compound represented by Formula 1 can highly contribute to the improvement in performance and lifetime of an organic light emitting device. Especially, such an improvement in an electron transport capability can highly contribute to the maximization of performance in full-color organic light emitting panels.

MODE FOR INVENTION

In the present invention, the compound represented by Formula 1 has a core (e.g., an indenoanthracene core) where an anthracene moiety with excellent device characteristics is fused with a fluorene moiety or the like with excellent fluorescent properties, wherein a substituent (represented by Formula 2 or 3, e.g. a heterocyclic group such as a benzimidazole group, a benzothiazole group, a benzoxazole group, a pyridinyl group or a bipyridinyl group) having an electron transport capability is substituted for the core. The compound is a kind of anthracene derivative.

Accordingly, in the present invention, the compound represented by Formula 1 may be used as a hole injection material, a hole transport material, a light emitting material, an electron transport material, or an electron injection material in an organic light emitting device, and preferably used as an electron transport material, or an electron injection/transport material.

In the present invention, in $R^1$ through $R^{10}$ in the compound represented by Formula 1, the alkyl group of $C_1$~$C_{40}$, the alkenyl group of $C_2$~$C_{40}$, the alkynyl group of $C_2$~$C_{40}$, the cycloalkyl group of $C_3$~$C_{40}$, the heterocycloalkyl group of $C_3$~$C_{40}$, the arylalkyl group of $C_6$~$C_{40}$, the alkyloxy group of $C_1$~$C_{40}$, the aryloxy group of $C_5$~$C_{40}$, the aryl group of $C_5$~$C_{40}$, and the heteroaryl group of $C_5$-$C_{40}$ may be each independently substituted by at least one selected from the group consisting of deuterium, halogen, a nitrile group, a nitro group, an alkyl group of $C_1$~$C_{40}$ an alkenyl group of $C_2$~$C_{40}$, an alkynyl group of $C_2$~$C_{40}$, an alkoxy group of $C_1$~$C_{40}$, an amino group of $C_1$~$C_{40}$, a cycloalkyl group of $C_3$~$C_{40}$, a heterocycloalkyl group of $C_3$~$C_{40}$, an arylalkyl group of $C_6$-$C_{40}$, an aryl group of $C_5$~$C_{40}$ or a heteroaryl group of $C_5$~$C_{40}$. For example, hydrogen of the alkyl group may be substituted by the above mentioned substituent.

In the present invention, in the compound represented by Formula 1, at least one of $R^1$ through $R^4$ is a substituent represented by Formula 2, or a substituent represented by Formula 3.

In $R^1$ through $R^{10}$, non-limiting examples of the heteroaryl group of $C_5$~$C_{40}$ include pyridinyl, quinolinyl, isoquinolinyl, carbazolyl, N-carbazolphenyl, etc., but the present invention is not limited thereto.

Also, in $R^1$ through $R^{10}$, the aryl group of $C_5$~$C_{40}$ may be selected from the group consisting of the chemical structures represented by Formula 4 below, but the present invention is not limited thereto.

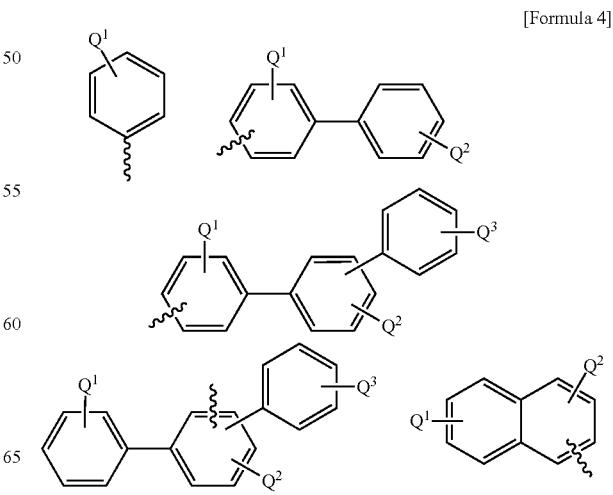

[Formula 4]

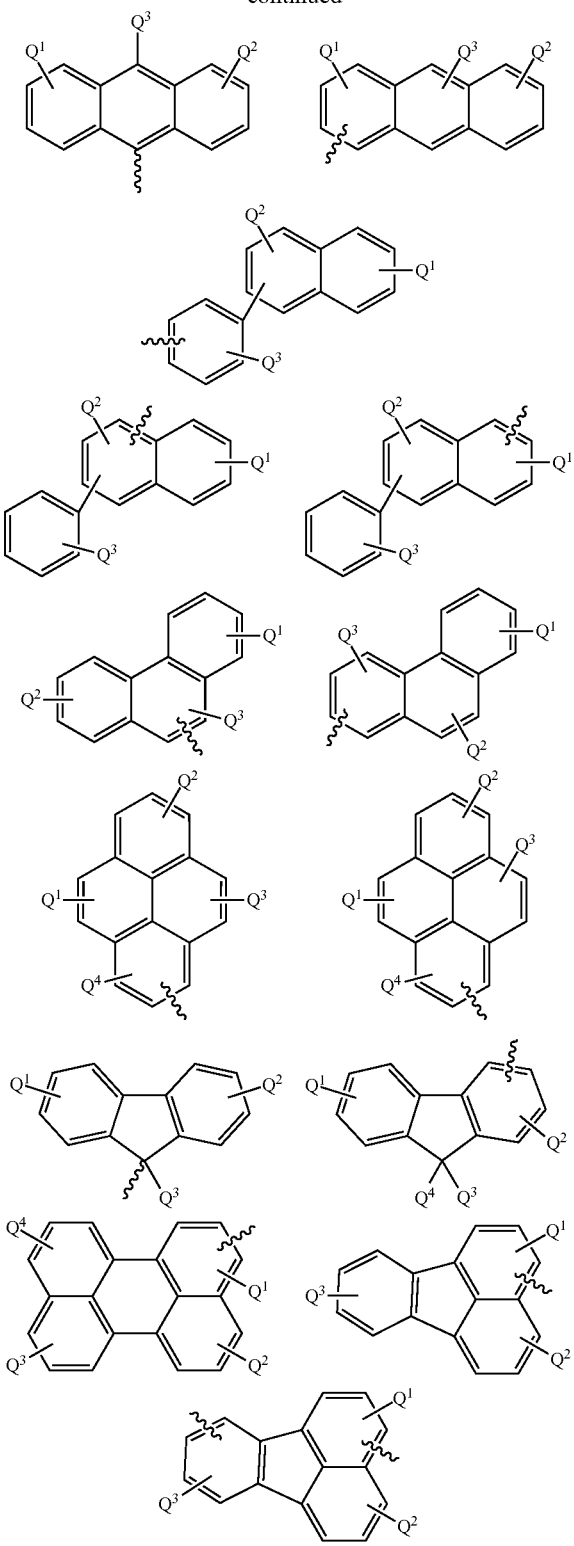

heterocycloalkyl group of $C_3$~$C_{40}$, an aryl alkyl group of $C_6$~$C_{40}$, an aryl group of $C_5$~$C_{40}$, and a heteroaryl group of $C_5$~$C_{40}$.

Also, in $Q^1$ through $Q^4$, the alkyl group of $C_1$~$C_{40}$, the alkenyl group of $C_2$~$C_{40}$, the alkoxy group of $C_1$~$C_{40}$, the amino group of $C_1$~$C_{40}$, the cycloalkyl group of $C_3$~$C_{40}$, the heterocycloalkyl group of $C_3$~$C_{40}$, the aryl group of $C_5$~$C_{40}$ and a heteroaryl group of $C_5$~$C_{40}$ may be each independently substituted by at least one selected from the group consisting of deuterium, halogen, a nitrile group, a nitro group, an alkyl group of $C_1$~$C_{40}$ an alkenyl group of $C_2$~$C_{40}$, an alkynyl group of $C_2$~$C_{40}$, an alkoxy group of $C_1$~$C_{40}$ an amino group of $C_1$~$C_{40}$, a cycloalkyl group of $C_3$~$C_{40}$, a heterocycloalkyl group of $C_3$~$C_{40}$, an arylalkyl group of $C_6$~$C_{40}$, an aryl group of $C_5$~$C_{40}$ and a heteroaryl group of $C_5$~$C_{40}$.

Also, in the substituents represented by Formulas 2 and 3, A represents a single bond, an arylene group of $C_5$~$C_{40}$, or a heteroarylene group of $C_5$~$C_{40}$. The arylene group of $C_5$~$C_{40}$ may be selected from the group consisting of the chemical structures represented by Formula 4. Also, non-limiting examples of the heteroarylene group of $C_5$~$C_{40}$ include pyridinyl, quinoline, isoquinoline, etc.

Representative examples of the compound represented by Formula 1 of the present invention include the following compounds A to E, but the compound represented by Formula 1 of the present invention is not limited thereto.

[Compound A]

Inv1

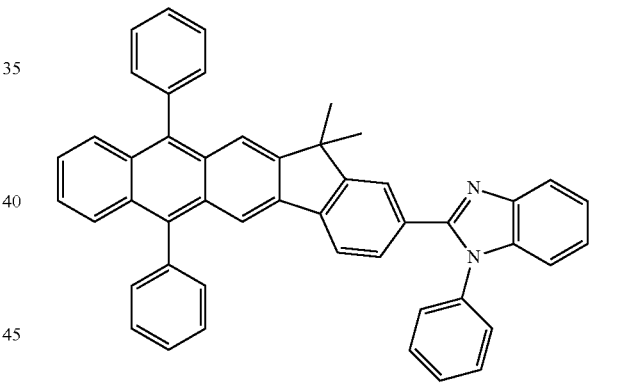

Inv-2

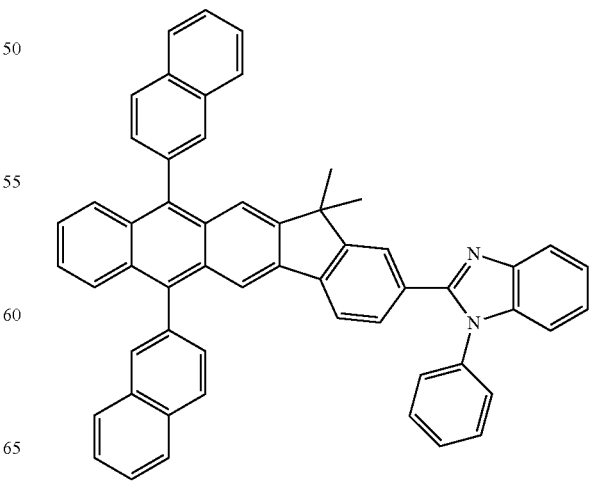

In Formula 4, $Q^1$ through $Q^4$ are the same or different and each independently selected from the group consisting of hydrogen, deuterium, halogen, a nitrile group, a nitro group, an alkyl group of $C_1$~$C_{40}$, an alkenyl group of $C_2$~$C_{40}$, an alkynyl group of $C_2$~$C_{40}$, an alkoxy group of $C_1$~$C_{40}$, an amino group of $C_1$~$C_{40}$, a cycloalkyl group of $C_3$~$C_{40}$, a

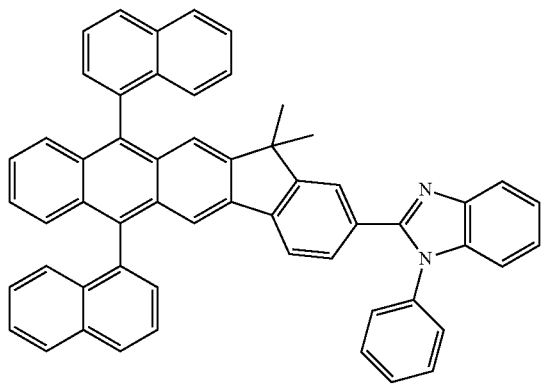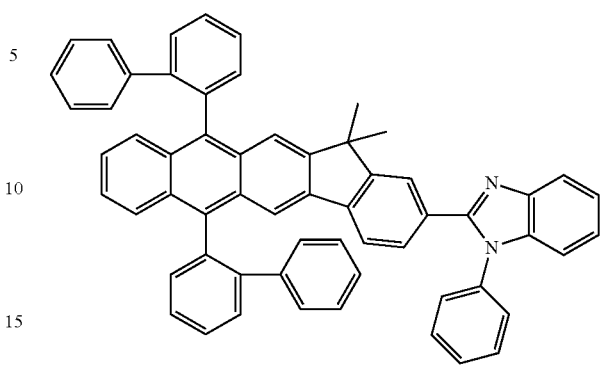

Inv-9
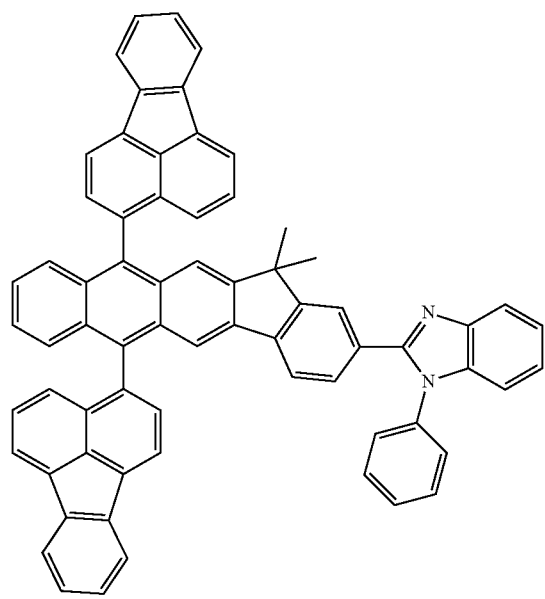
Inv-12
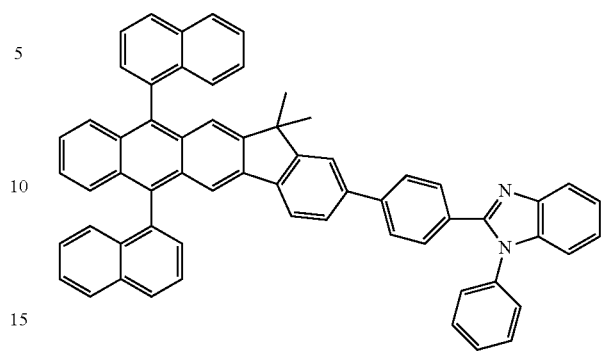
Inv-13
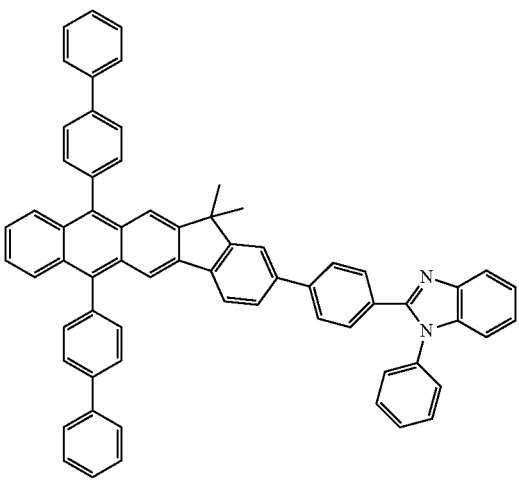
Inv10
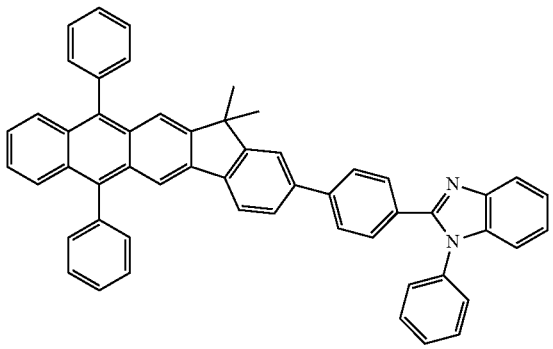
Inv-14
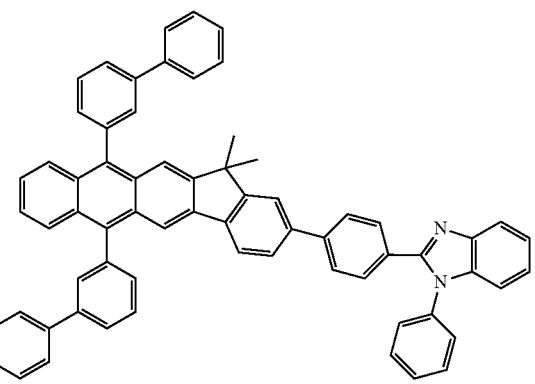
Inv-11
Inv-15
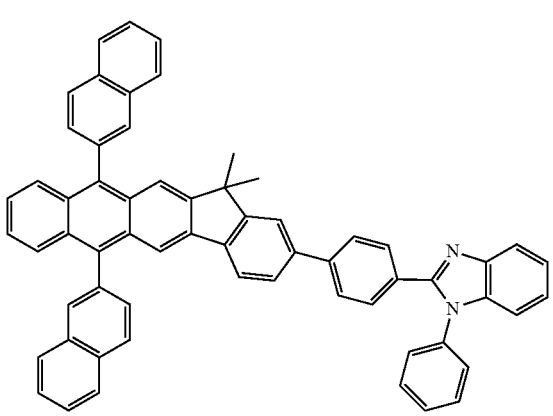

Inv-16
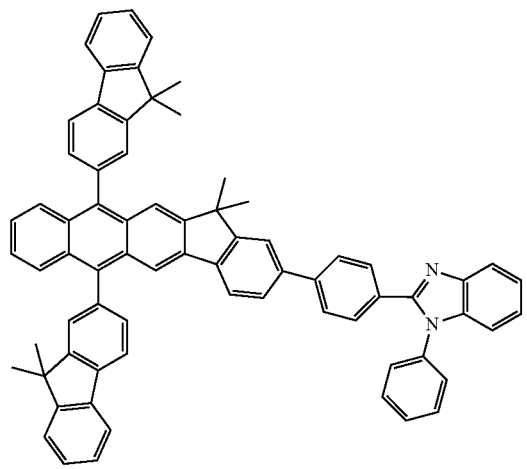
Inv-17
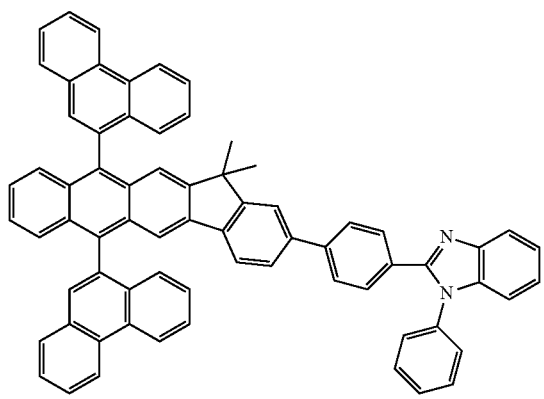
Inv-18
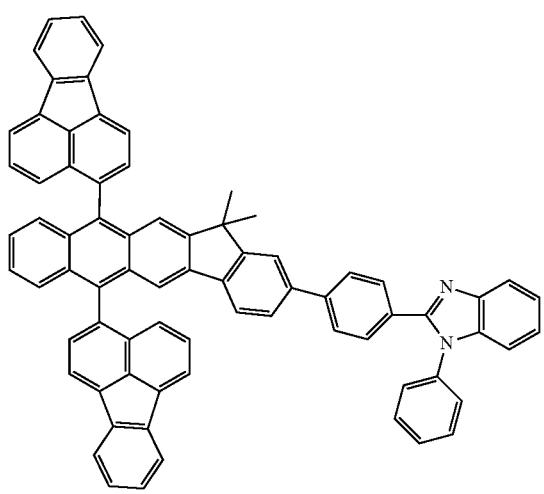
Inv-19
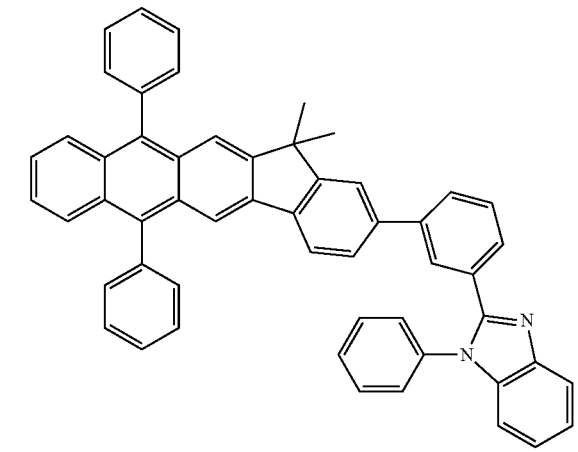
Inv-20
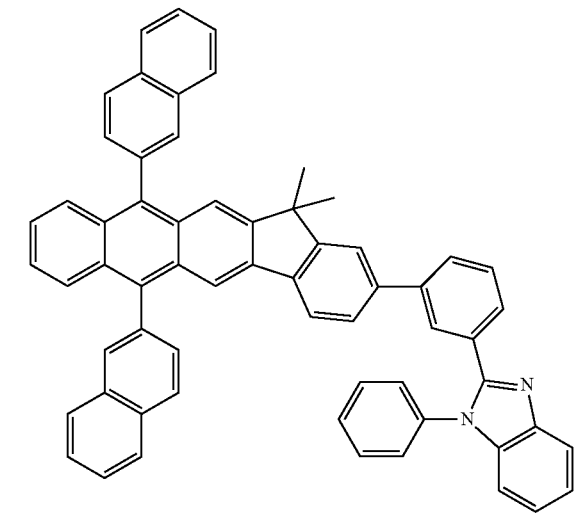
Inv-21
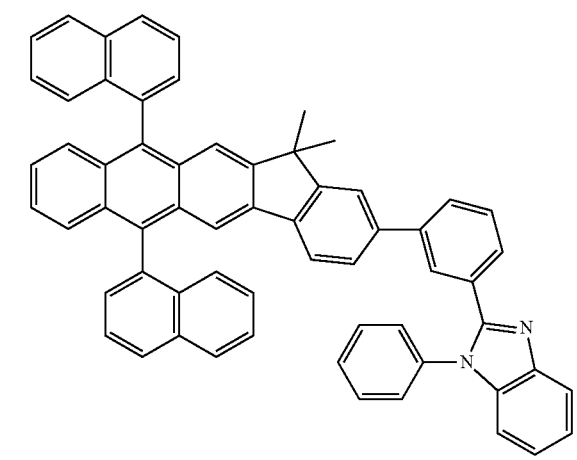

Inv-22
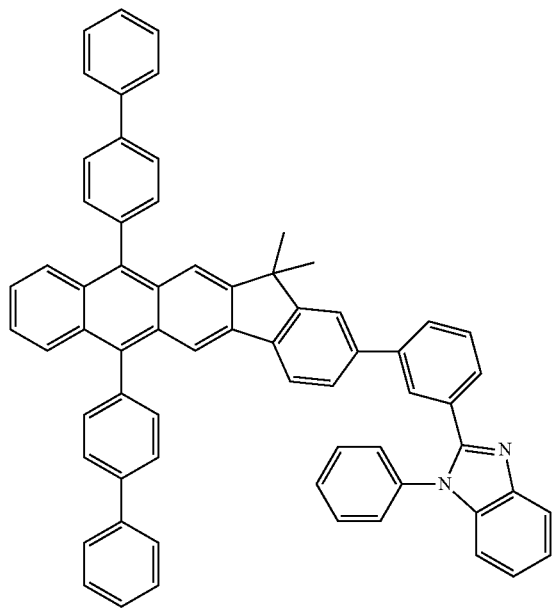
Inv-23
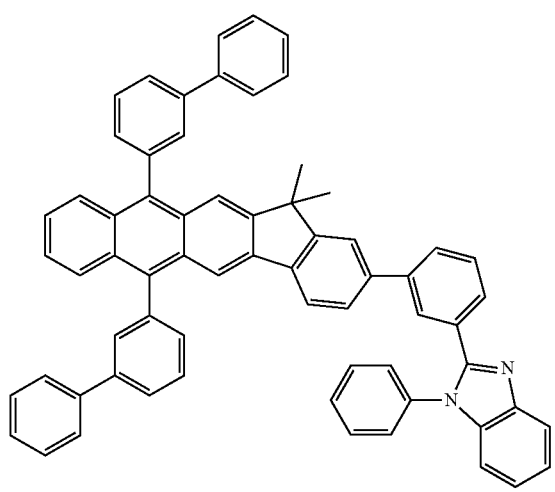
Inv-24
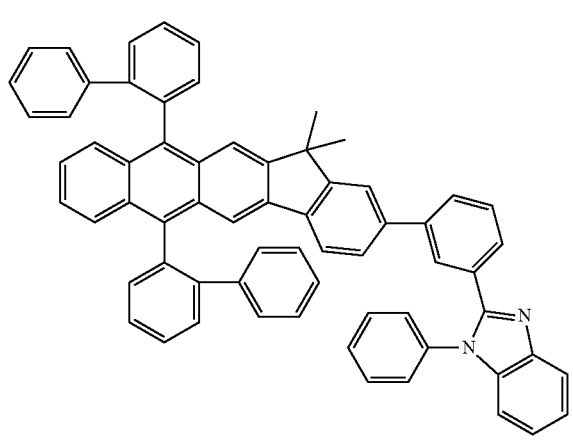
Inv-25
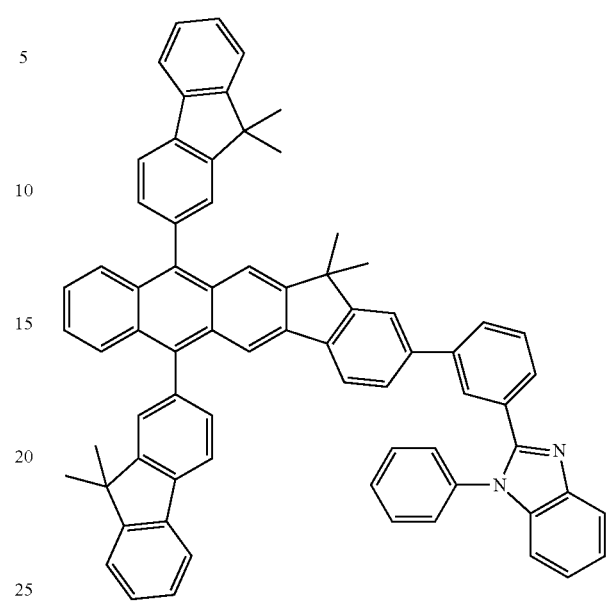
Inv-26
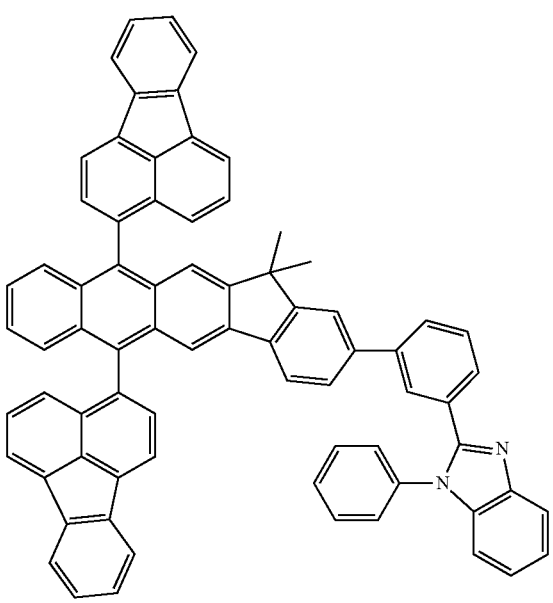

Inv-27
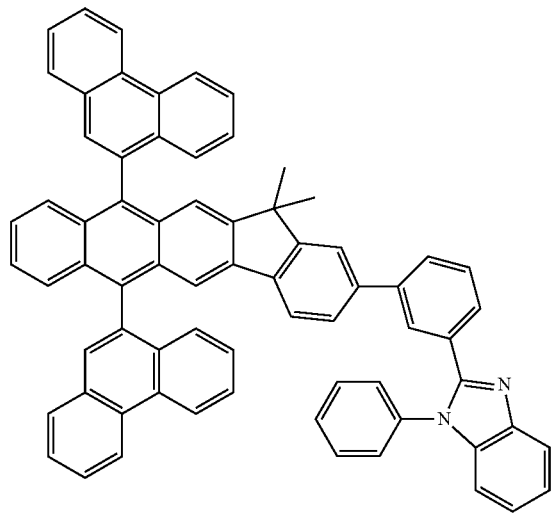
Inv-28
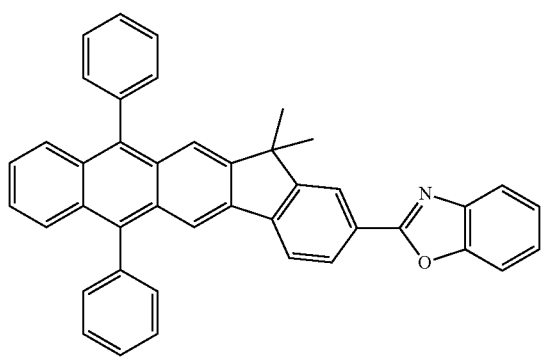
Inv-29
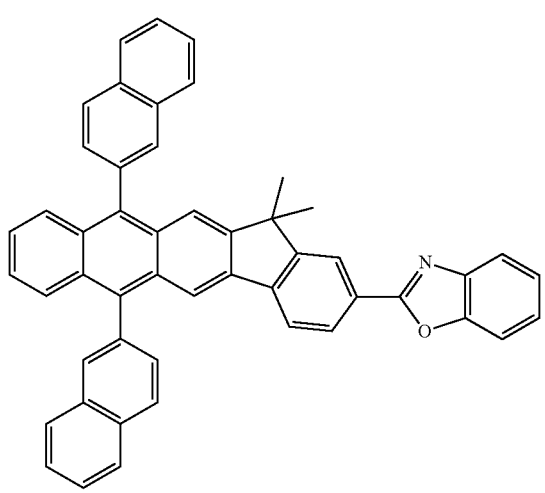
Inv-30
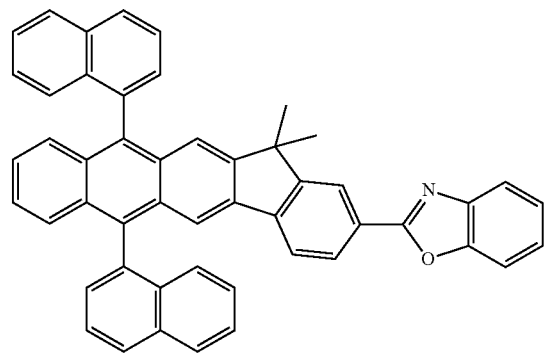
Inv-31
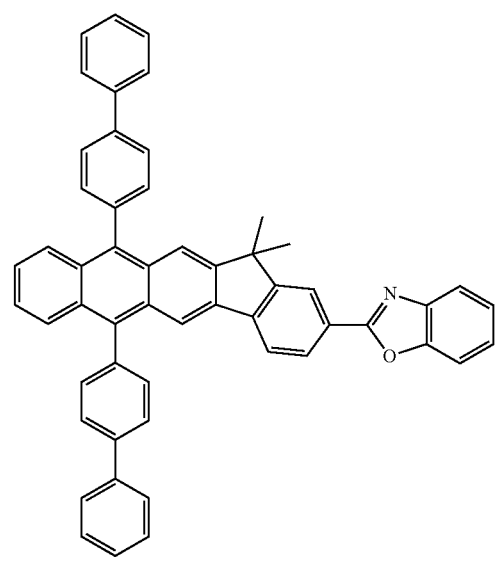
Inv-32
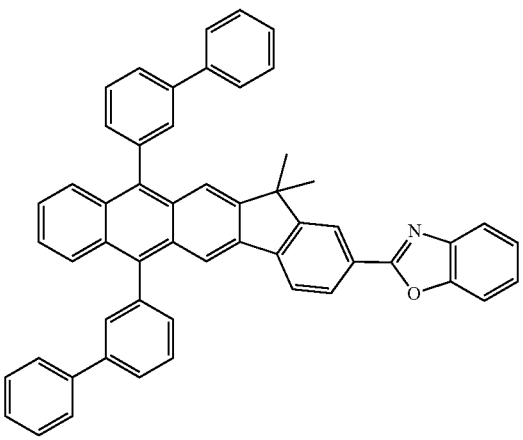

Inv-33
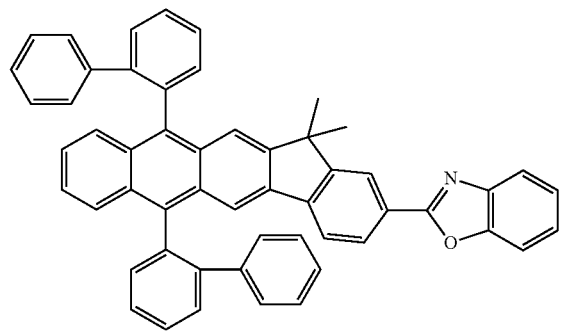
Inv-34
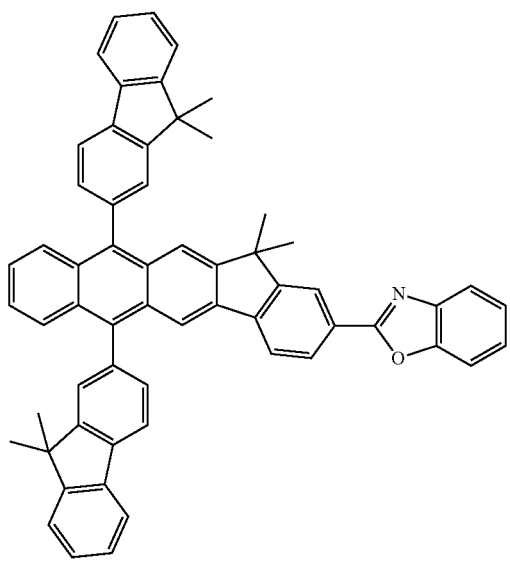
Inv-35
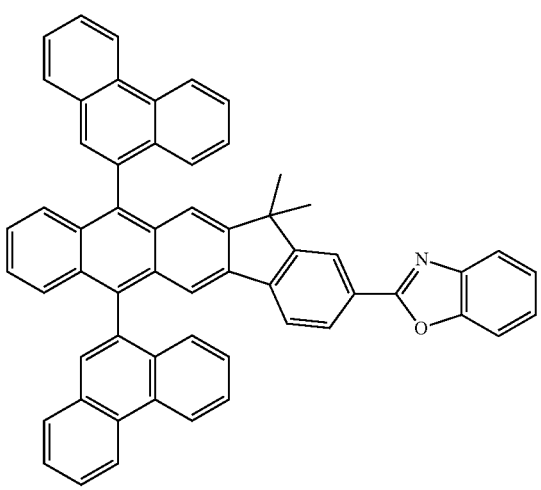
Inv-36
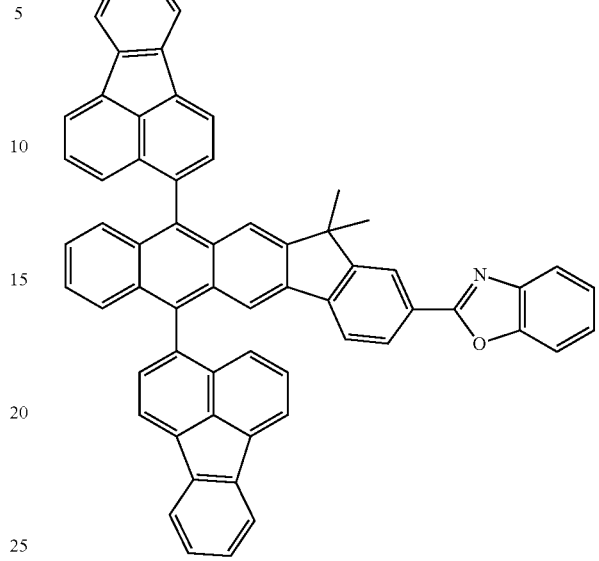
Inv-37
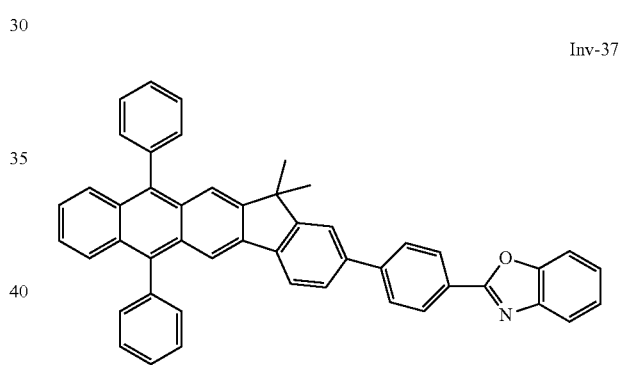
Inv-38
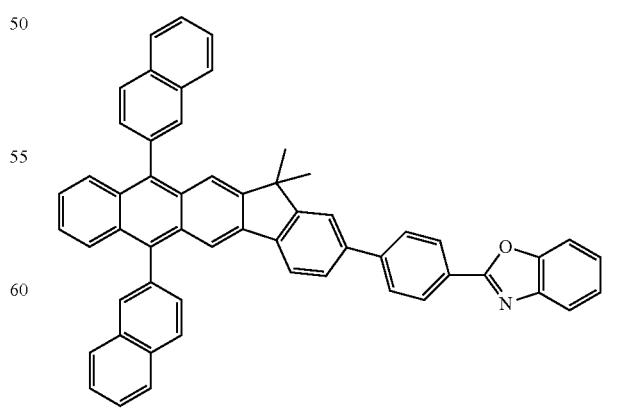

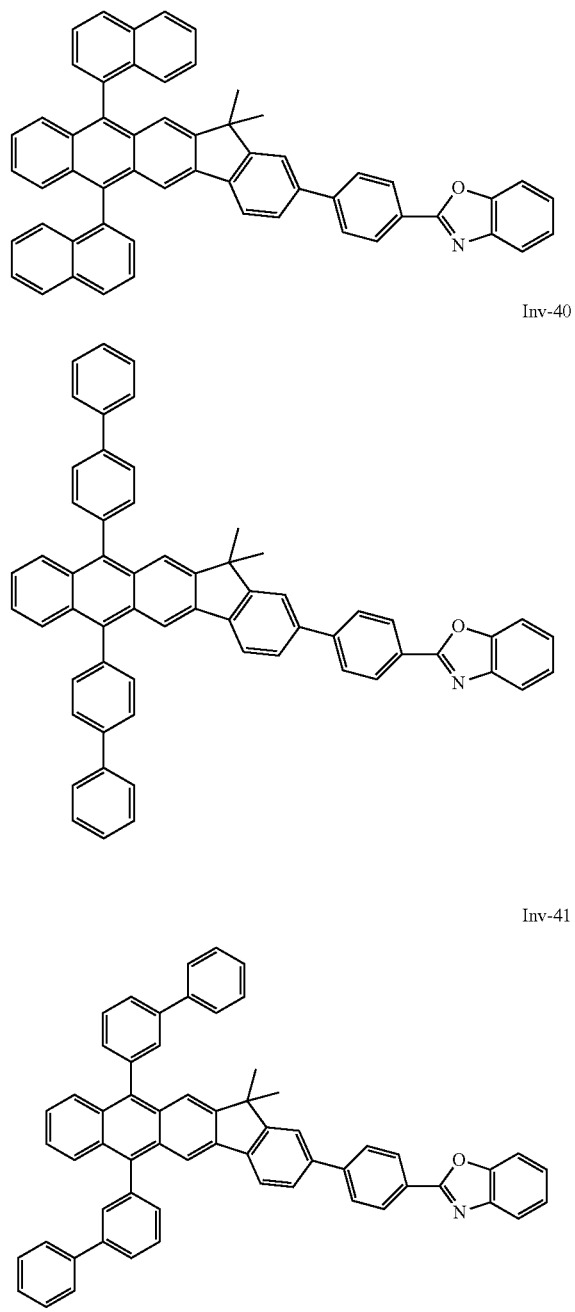
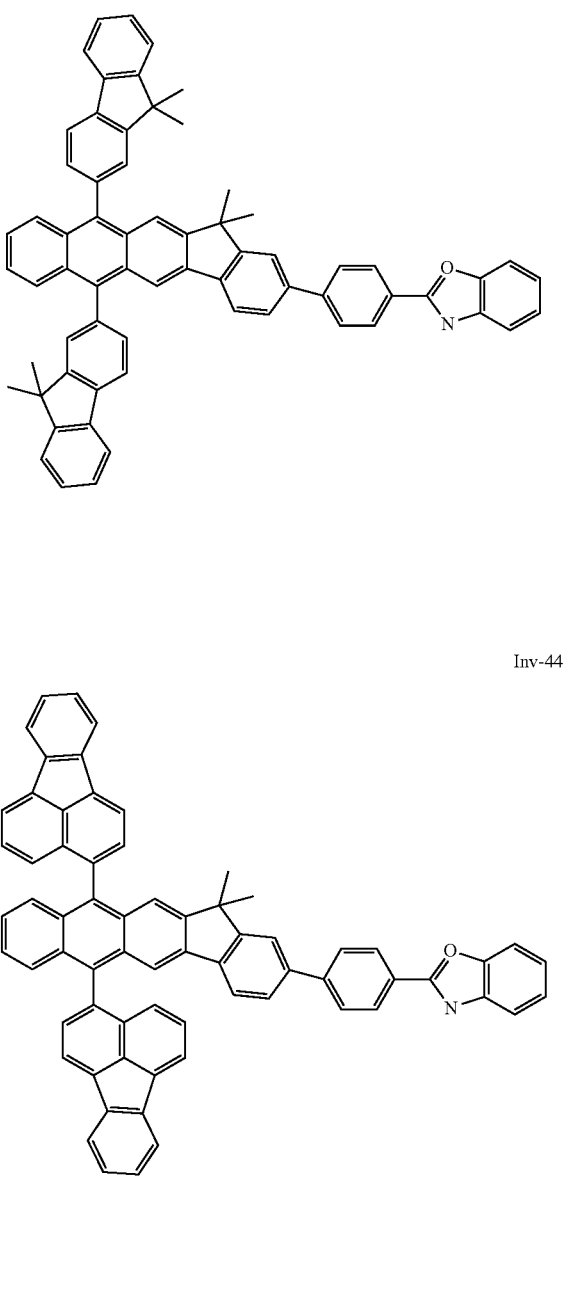

Inv-46
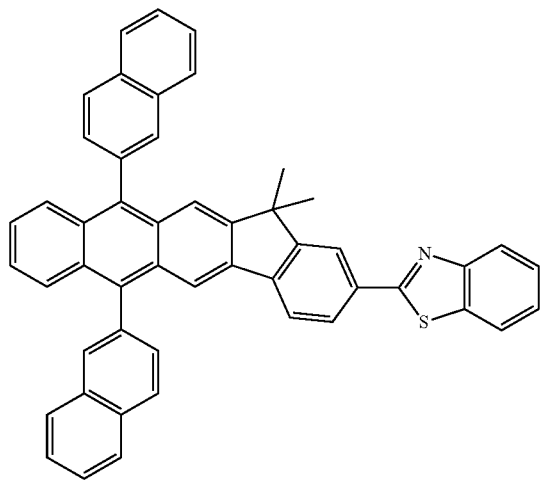
Inv-47
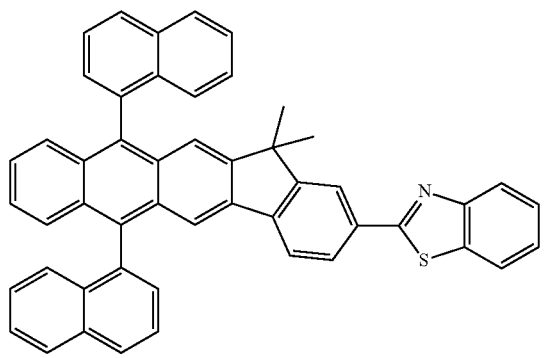
Inv-48
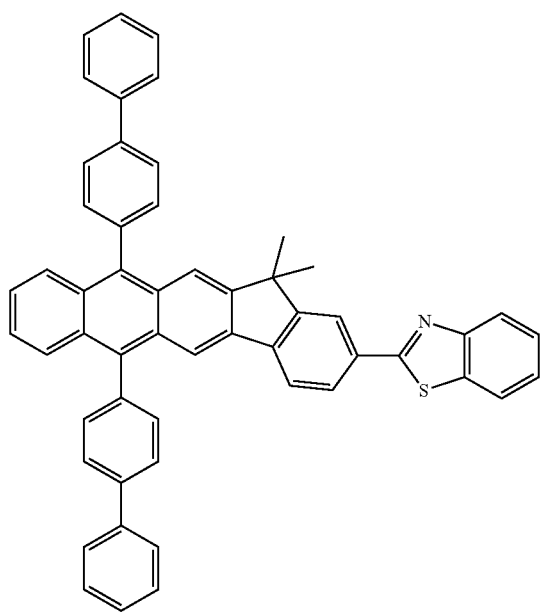
Inv-49
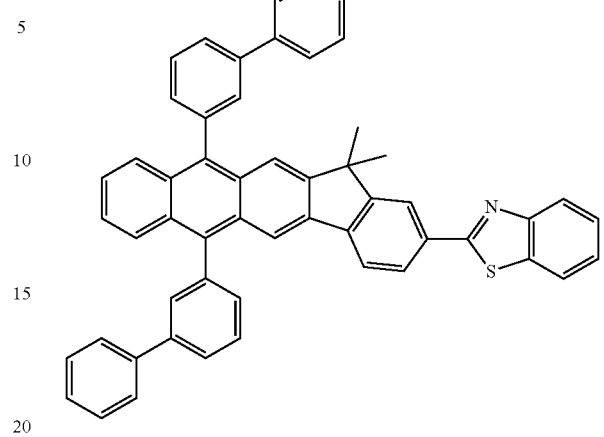
Inv-50
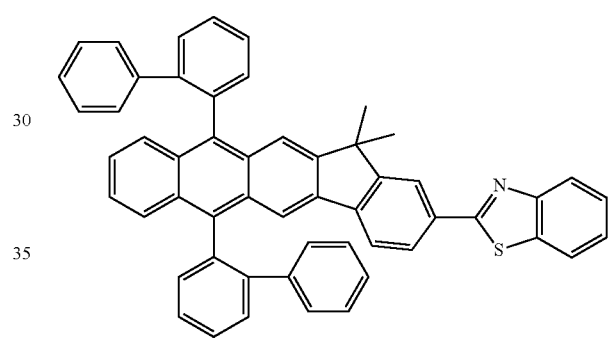
Inv-51
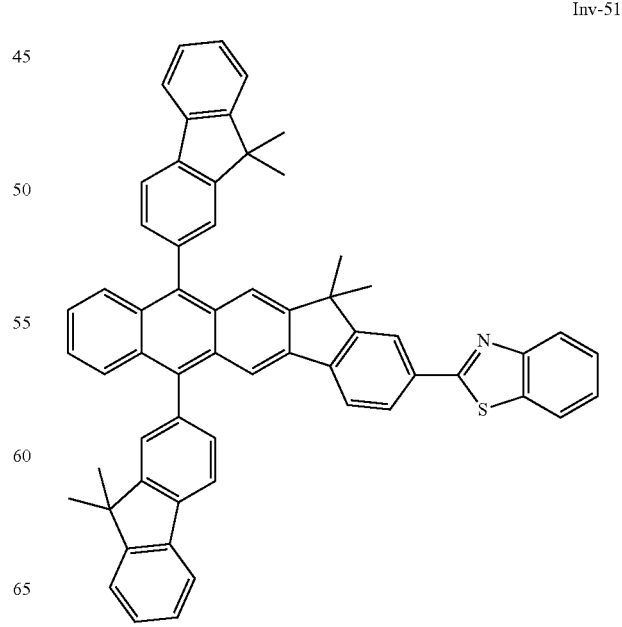

Inv-52
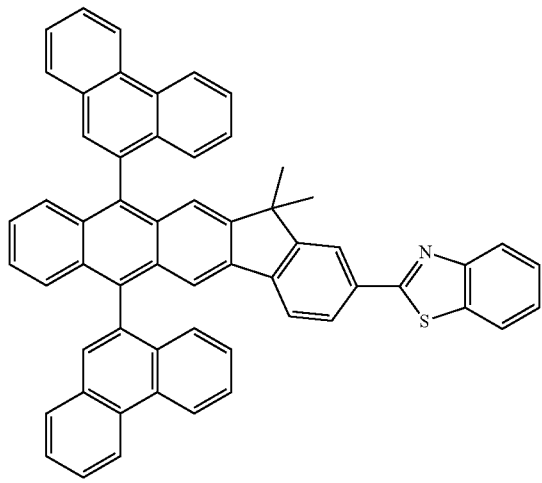
Inv-53
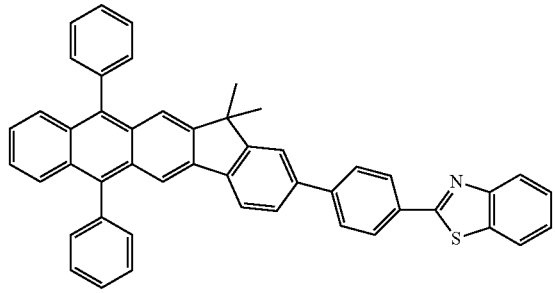
Inv-54
Inv-55
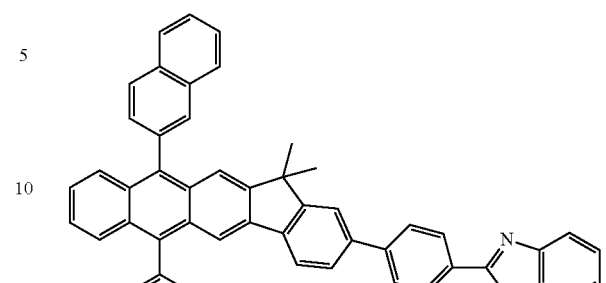
Inv-56
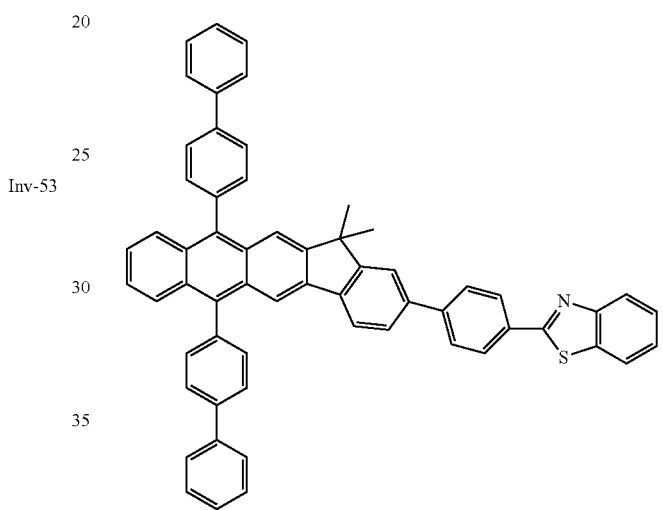
Inv-57
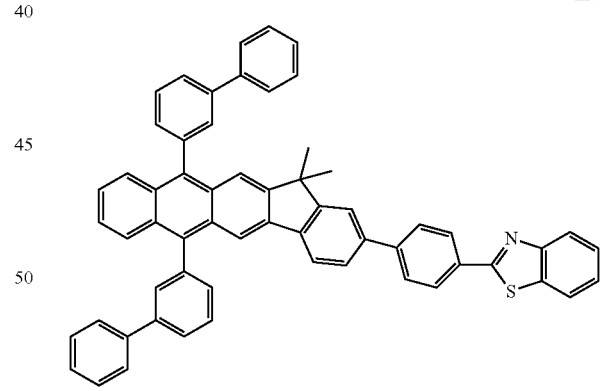
Inv-58
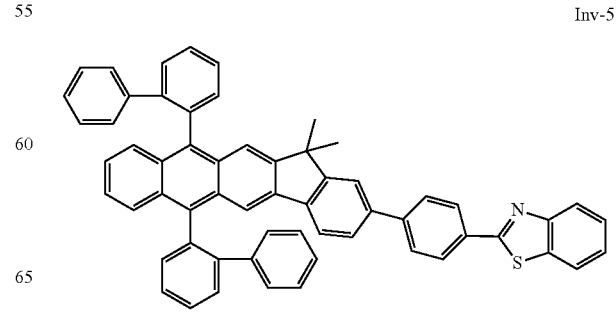

Inv-59
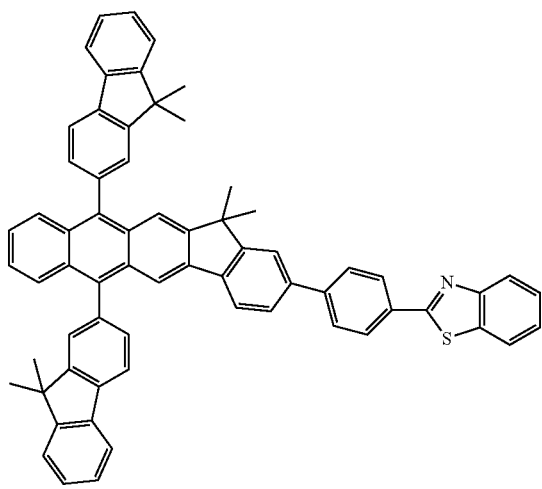
Inv-62
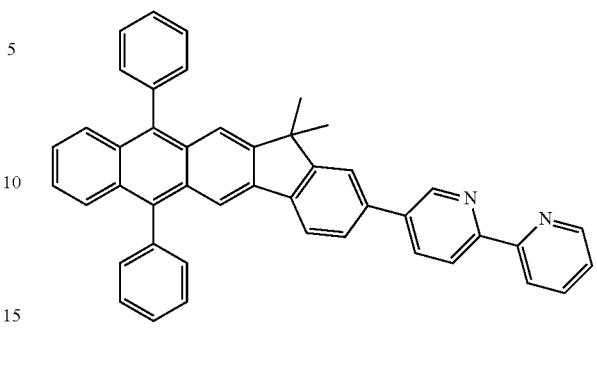
Inv-60
Inv-63
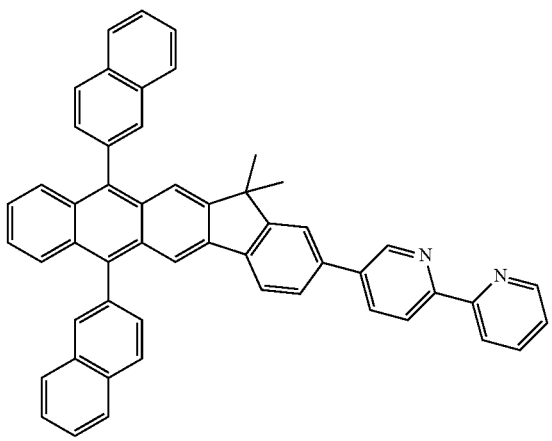
Inv-61
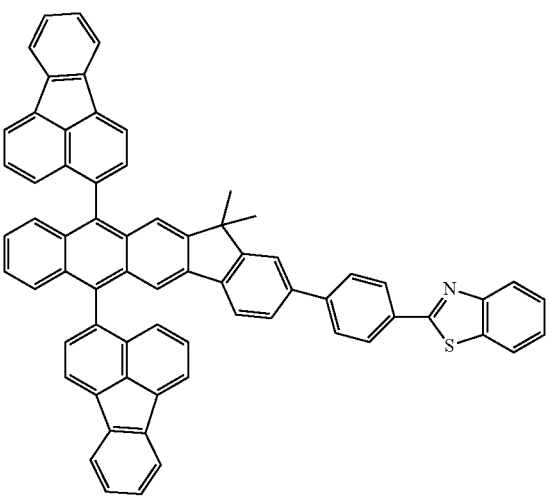
Inv-64
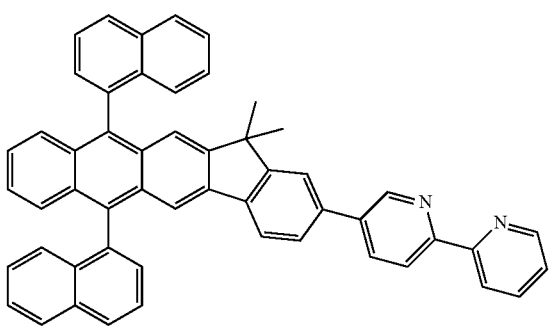

Inv-65
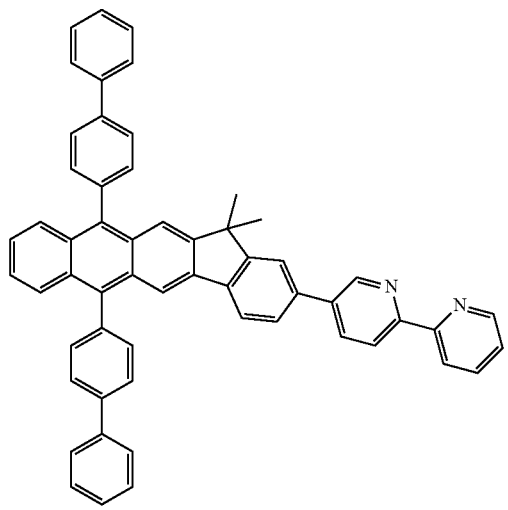
Inv-66
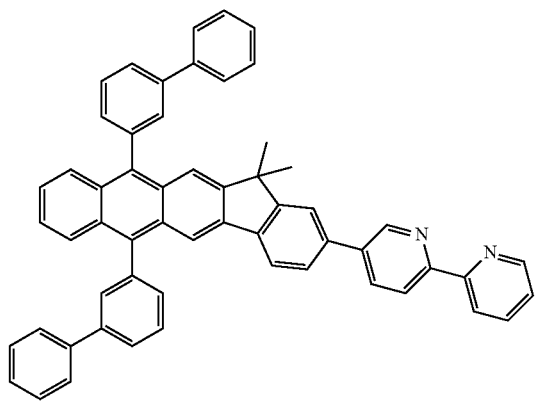
Inv-67
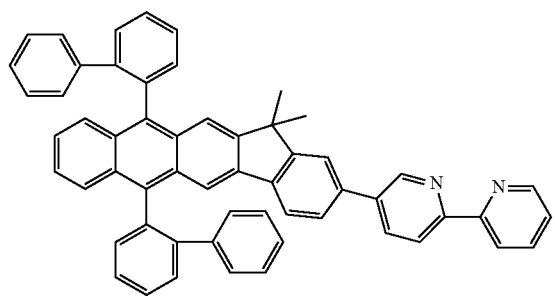
Inv-68
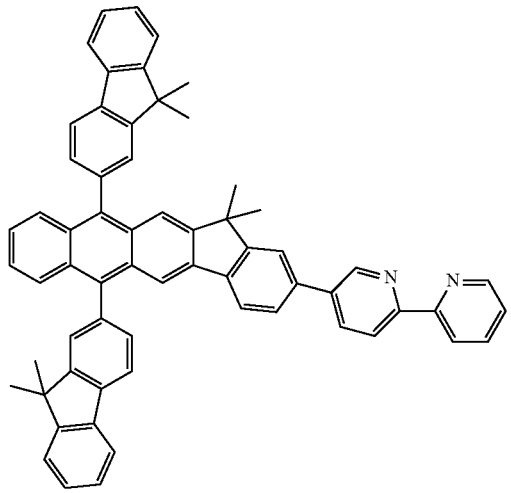
Inv-69
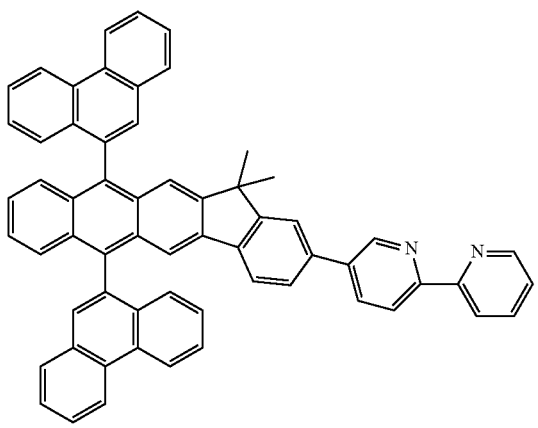
Inv-70
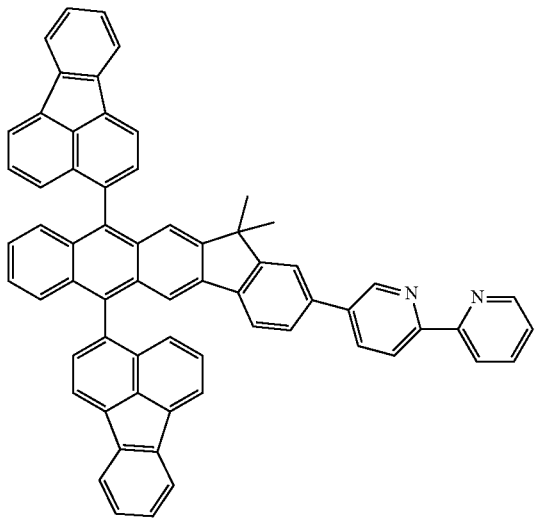

[Compound B]
Inv-71
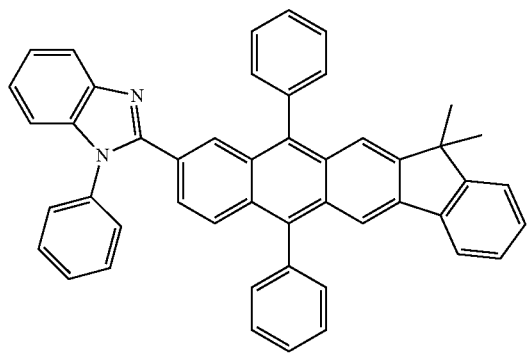
Inv-72
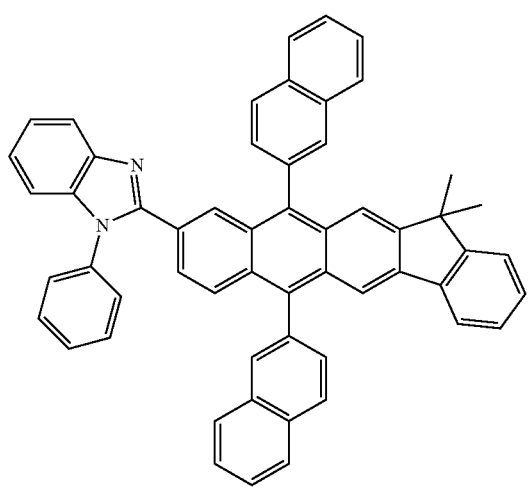
Inv-73
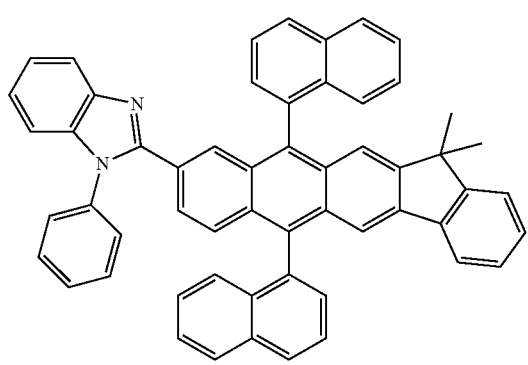
Inv-74
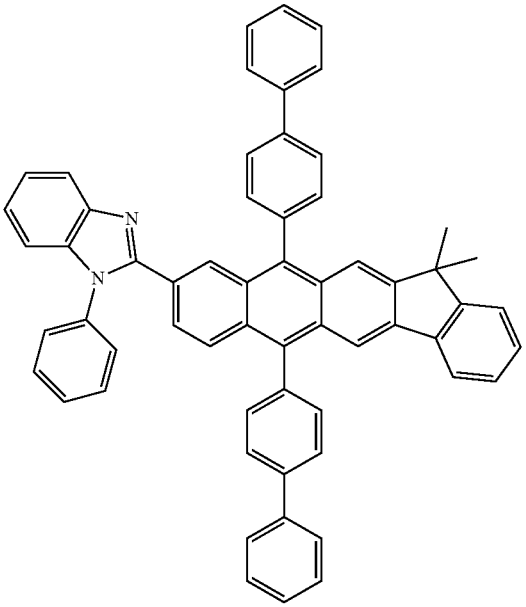
Inv-75
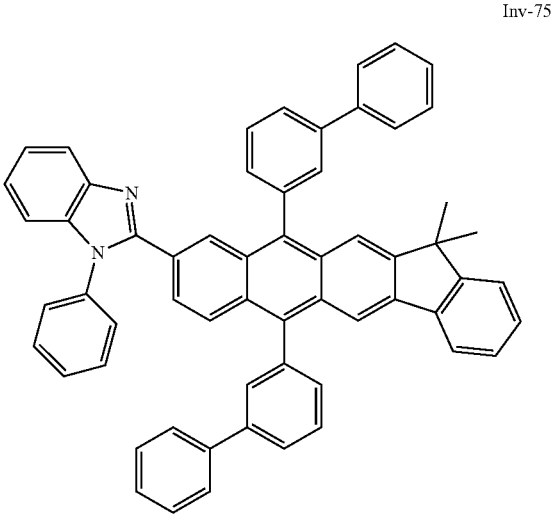
Inv-76
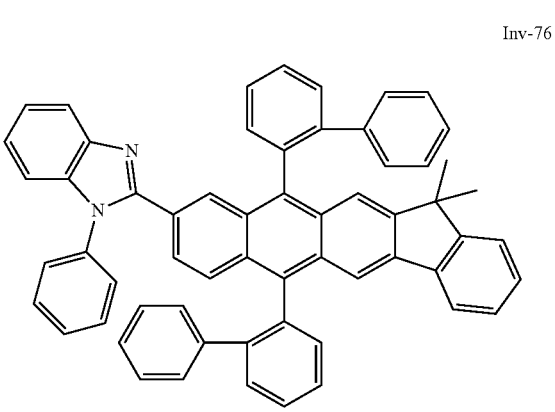

Inv-77
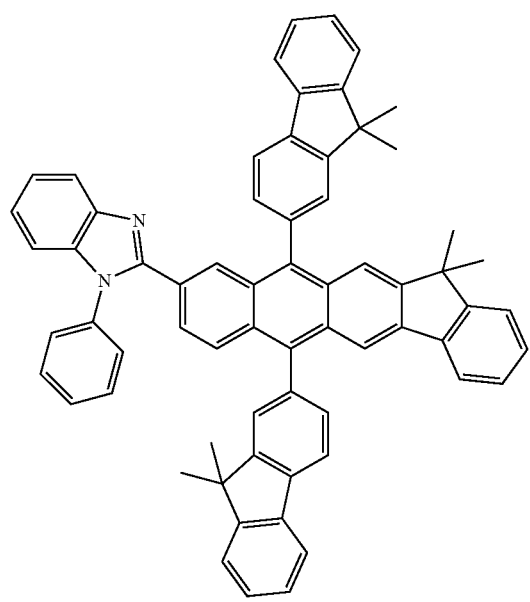
Inv-78
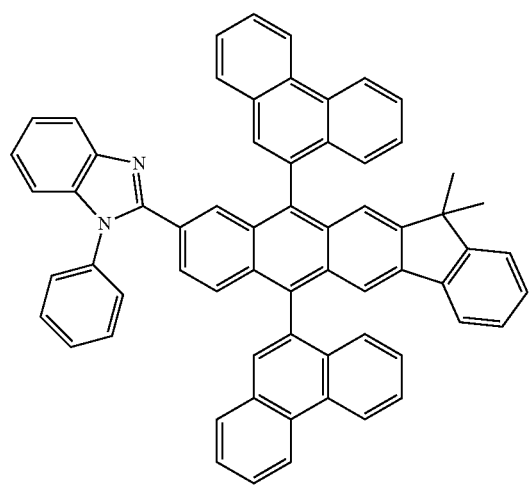
Inv-79
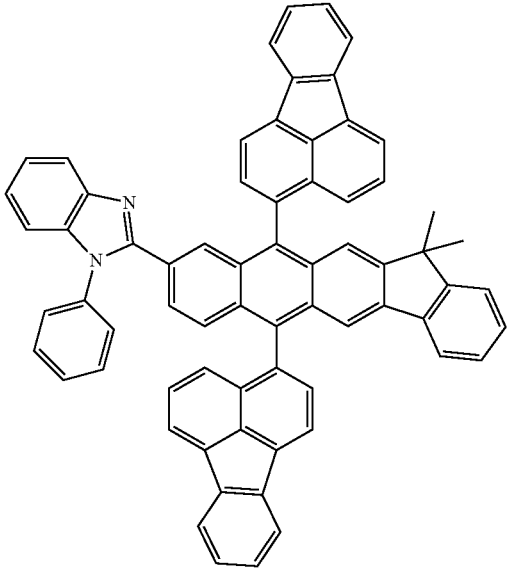
Inv-80
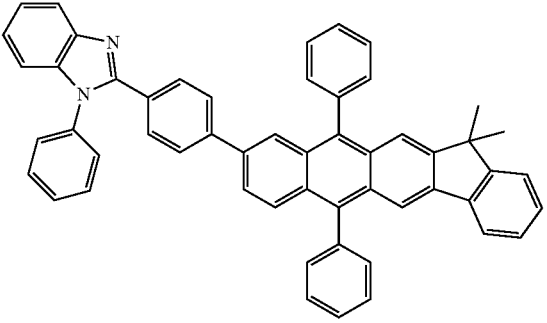
Inv-81
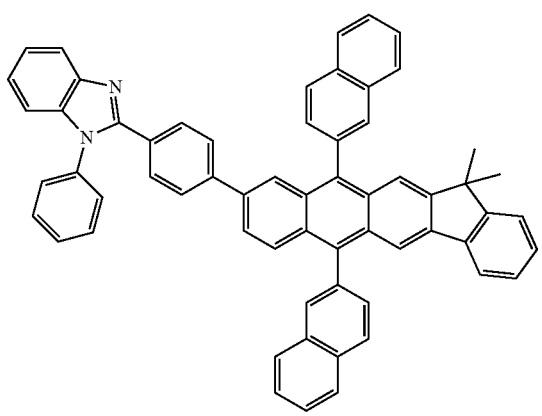

Inv-82
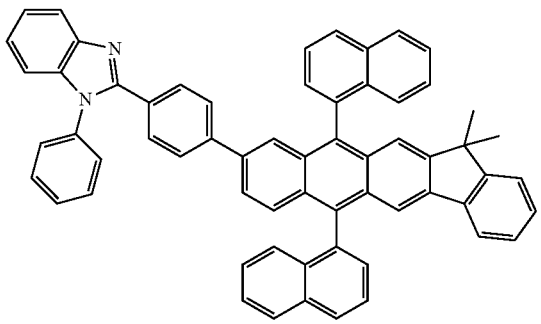
Inv-83
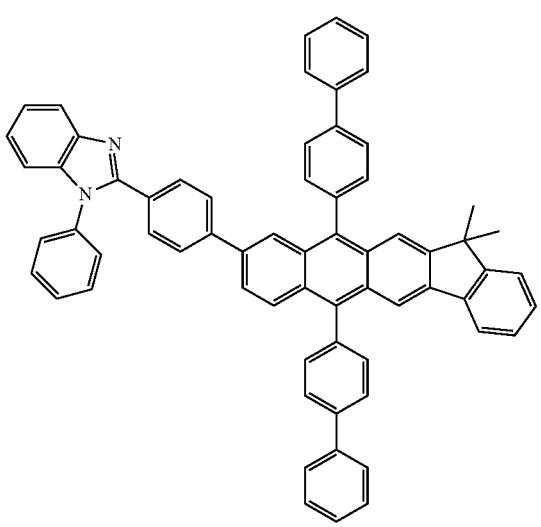
Inv-84
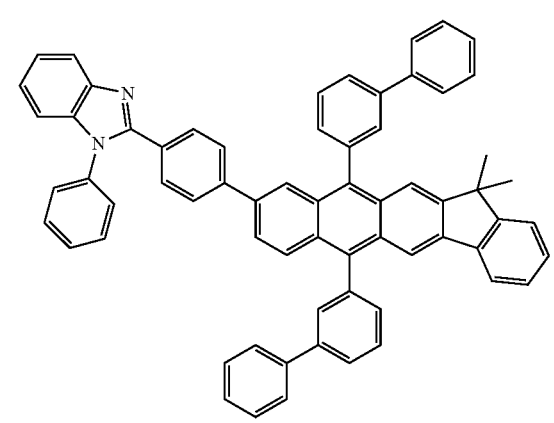
Inv-85
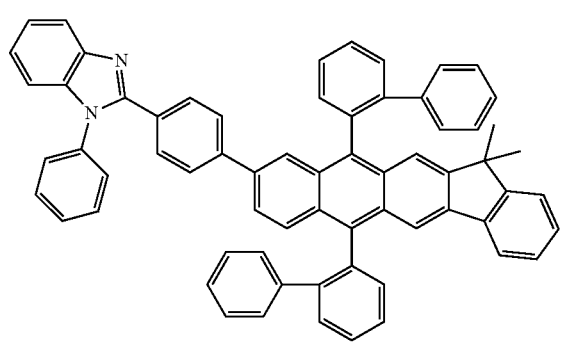
Inv86
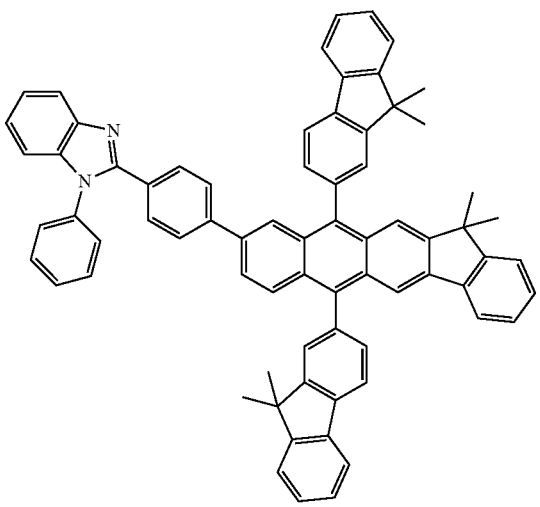
Inv-87
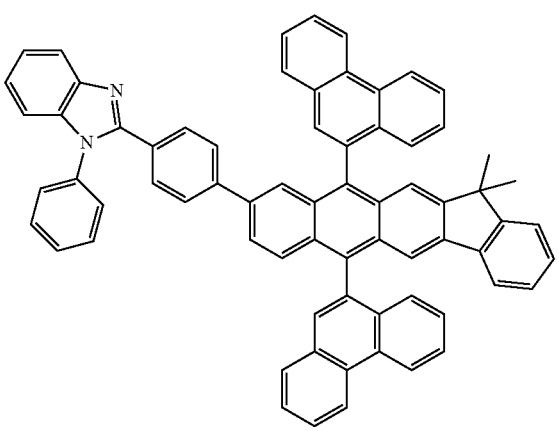
Inv-88
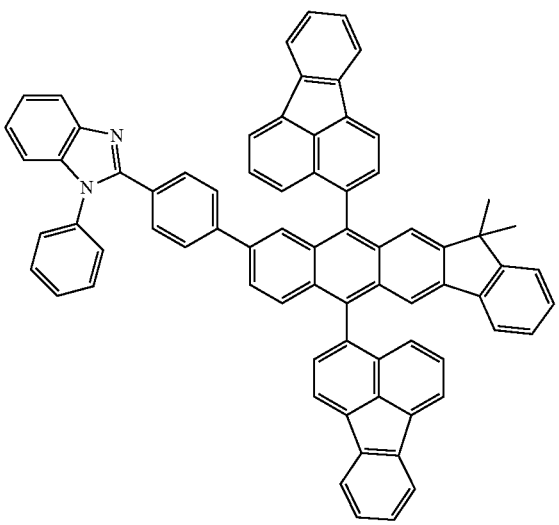

Inv-89
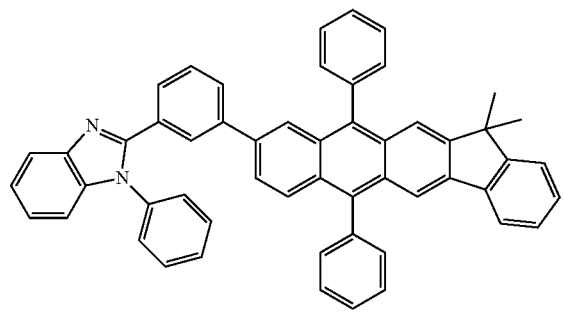
Inv-90
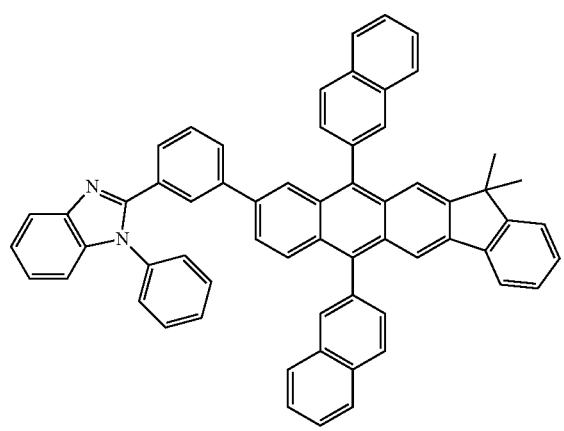
Inv-91
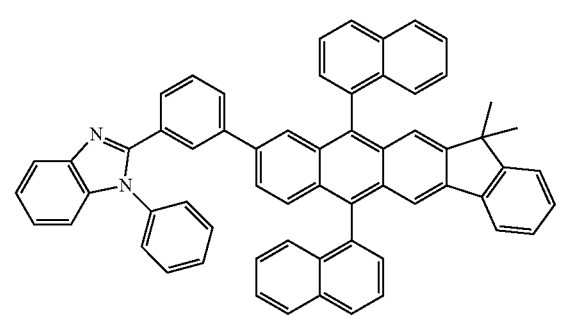
Inv-92
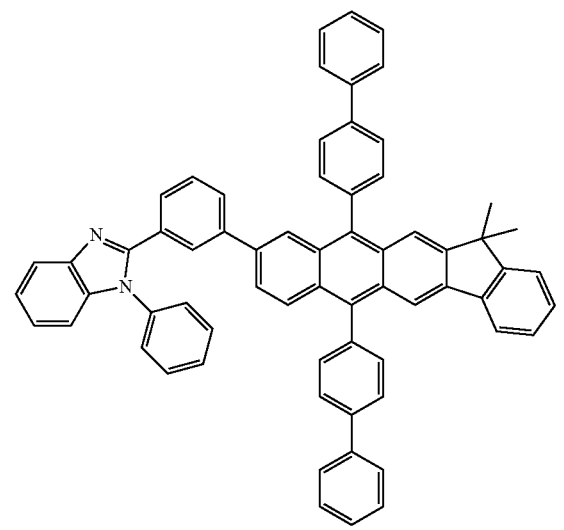
Inv-93
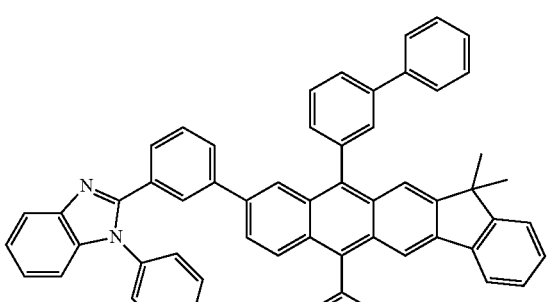
Inv-94
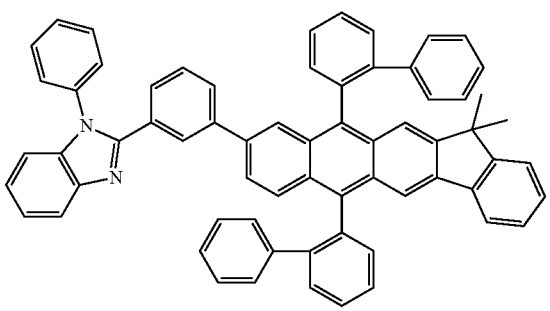
Inv-95
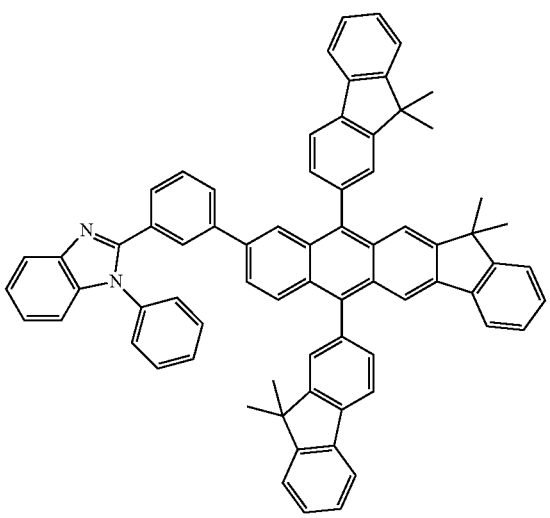

Inv-96
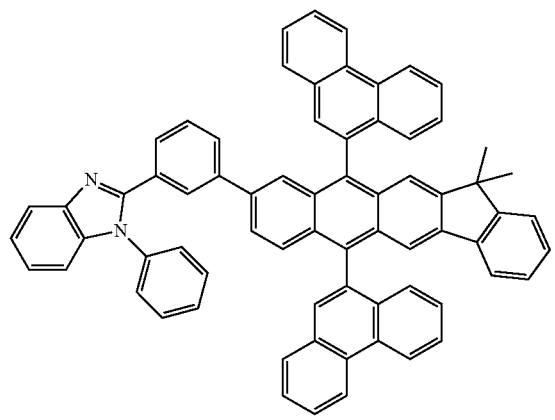
Inv-97
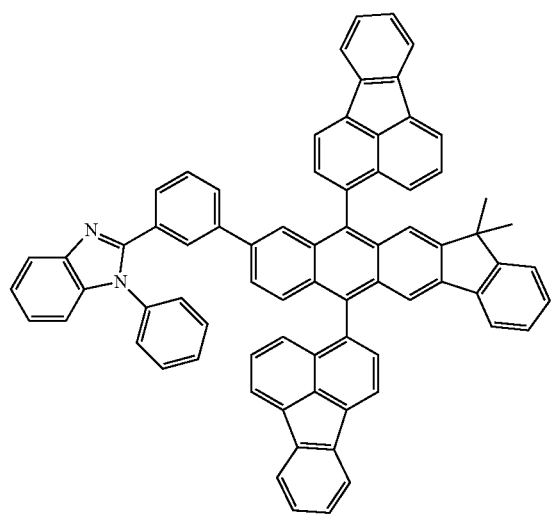
Inv-98
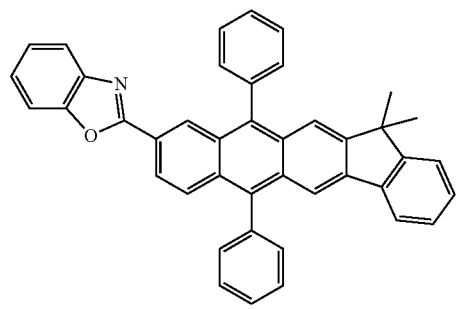
Inv-99
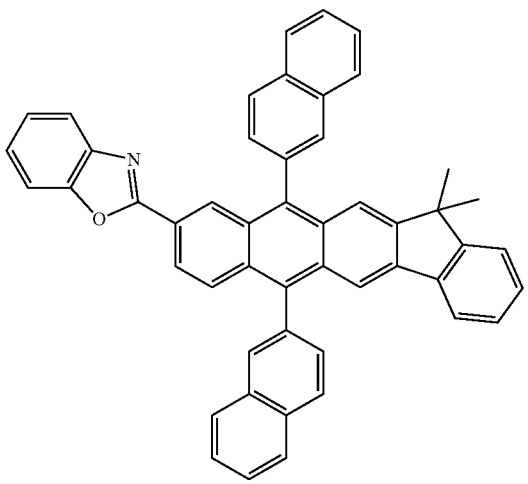
Inv-100
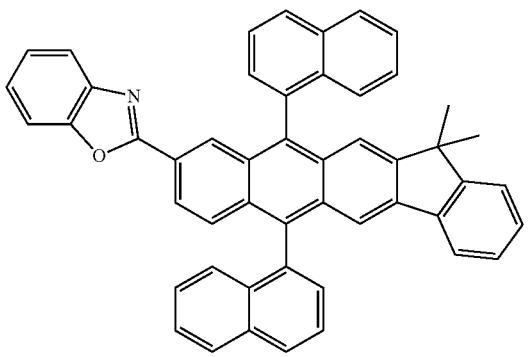
Inv-101
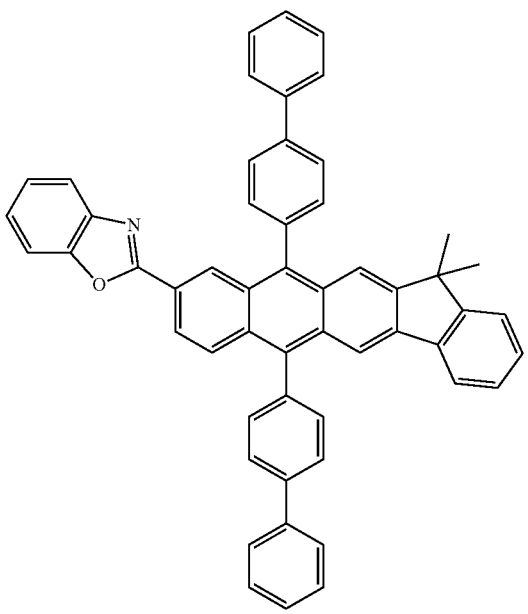

Inv-102
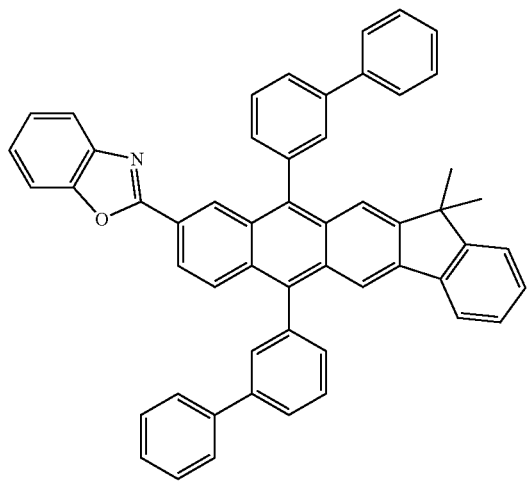
Inv-105
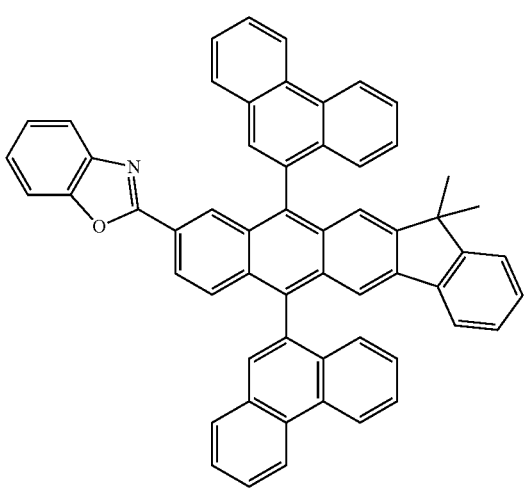
Inv-103
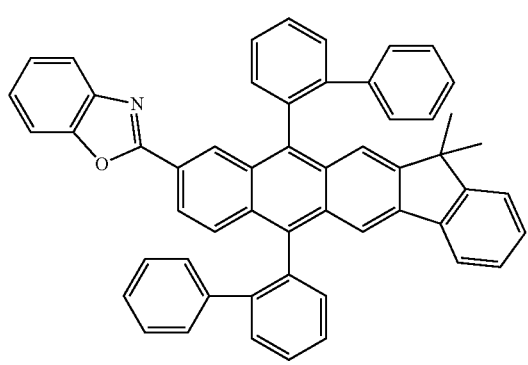
Inv-106
Inv-104
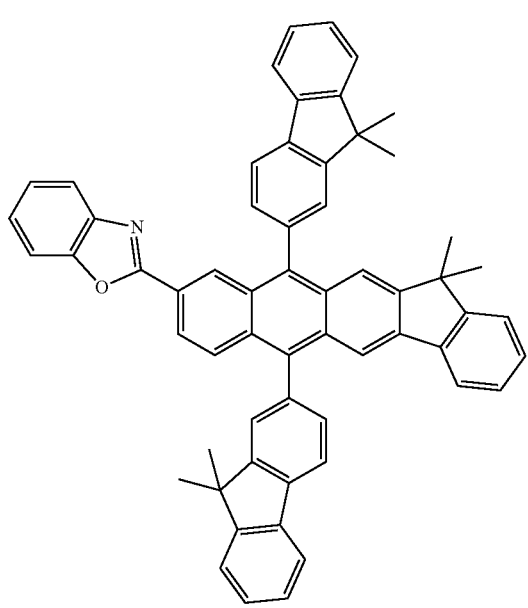
Inv-107
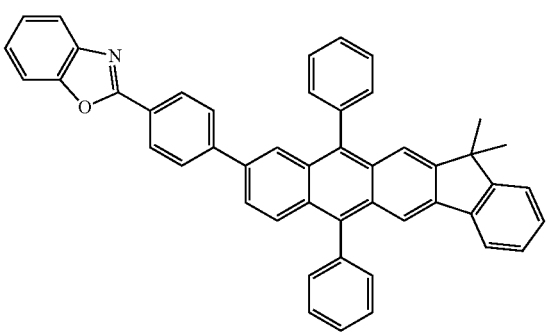

Inv-108
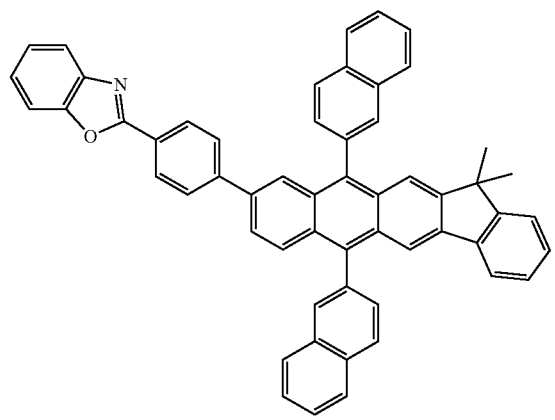
Inv-111
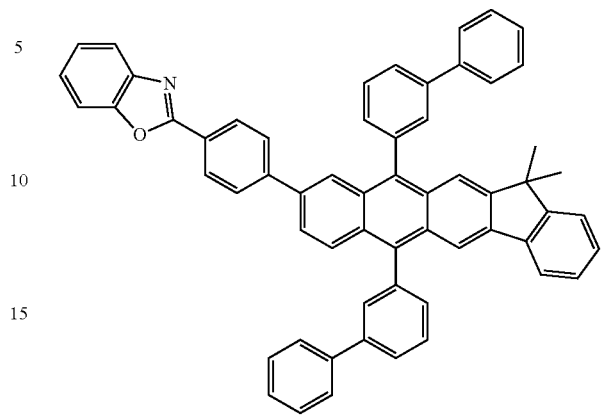
Inv-109
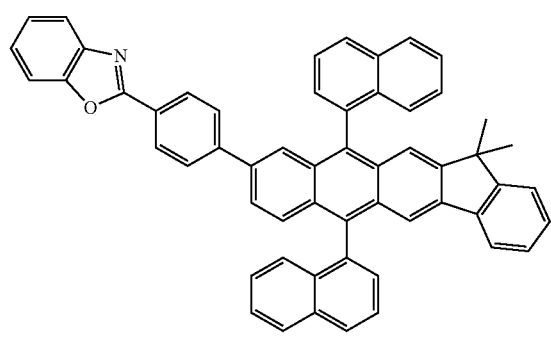
Inv-113
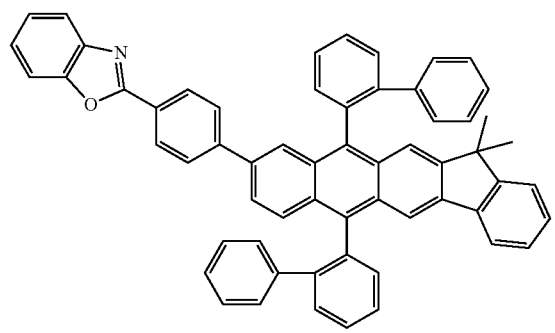
Inv-110
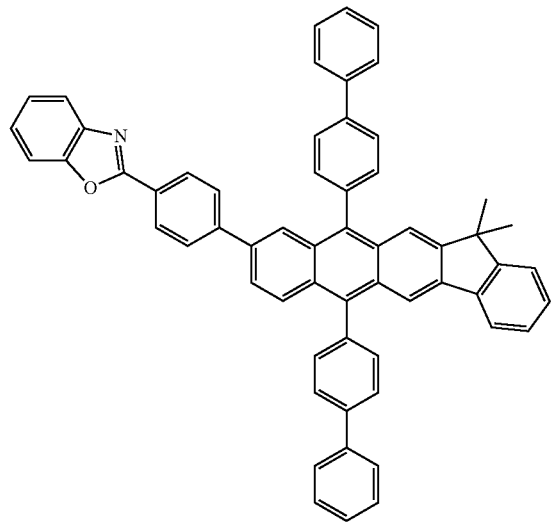
Inv-114
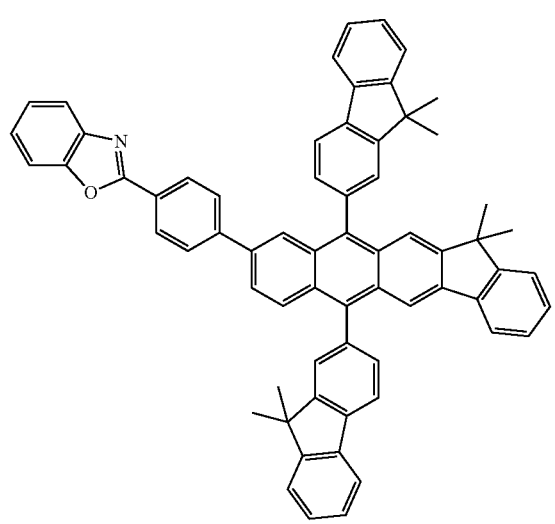

Inv115
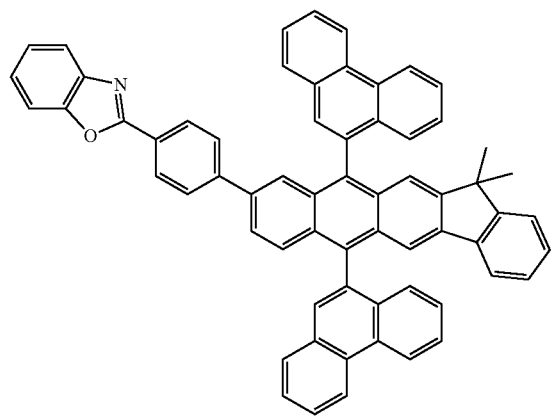
Inv-116
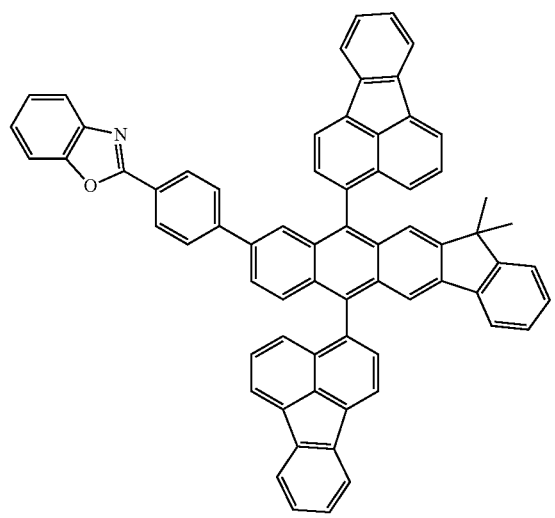
Inv-117
Inv-118
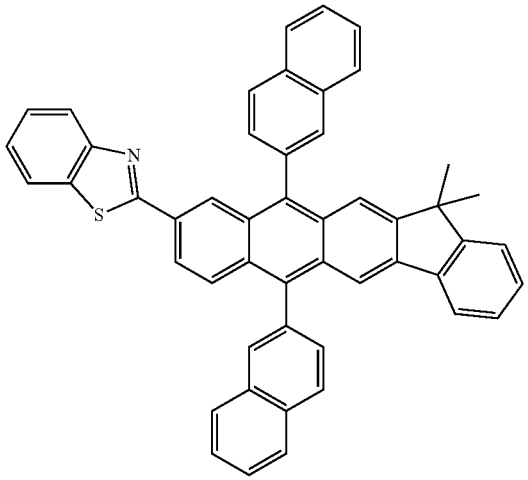
Inv-119
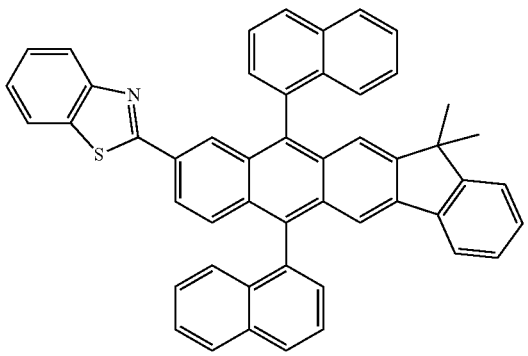
Inv120
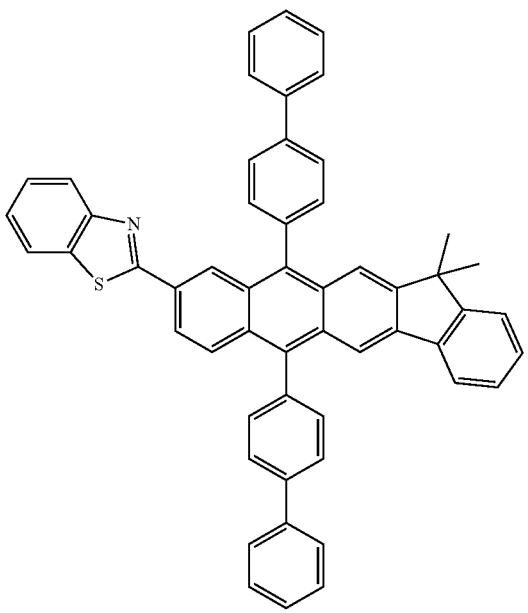

Inv121
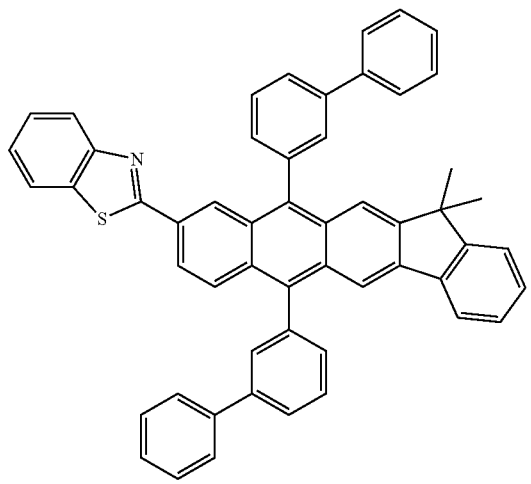
Inv-124
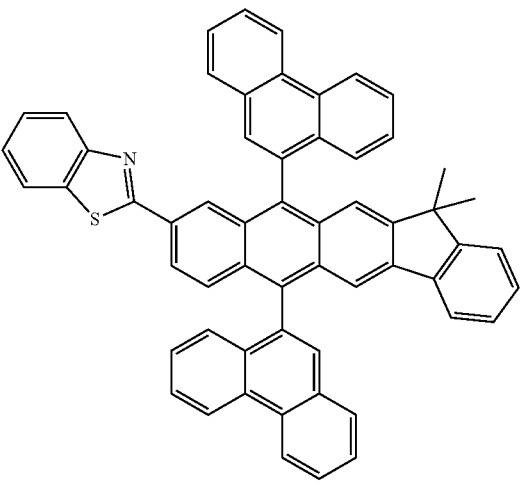
Inv-122
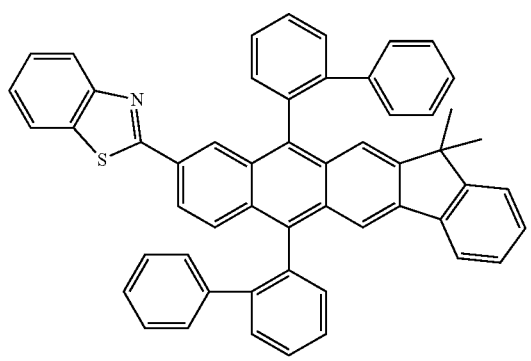
Inv125
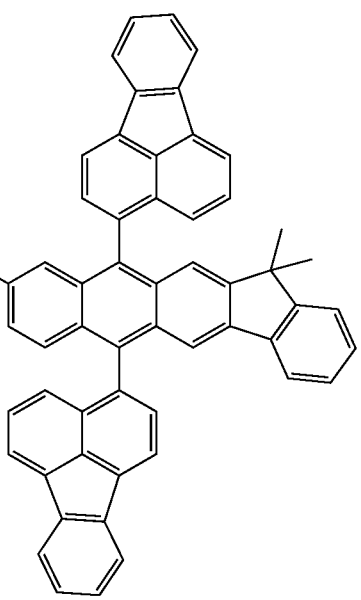
Inv-123
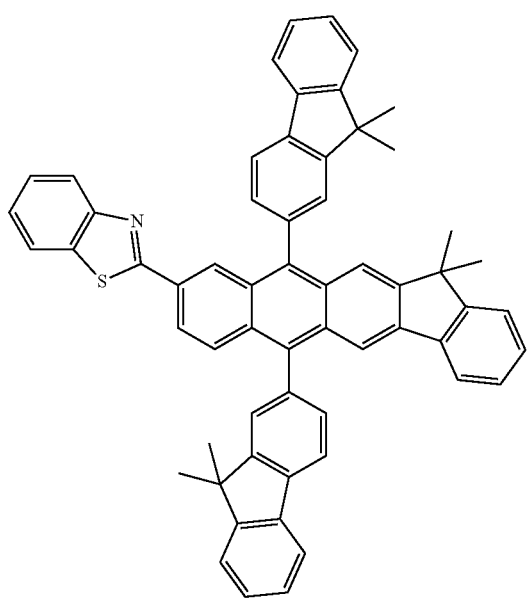
Inv126
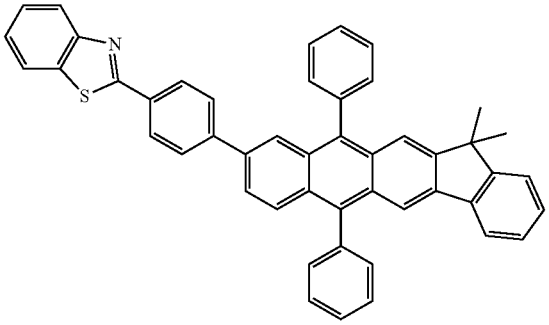

Inv127
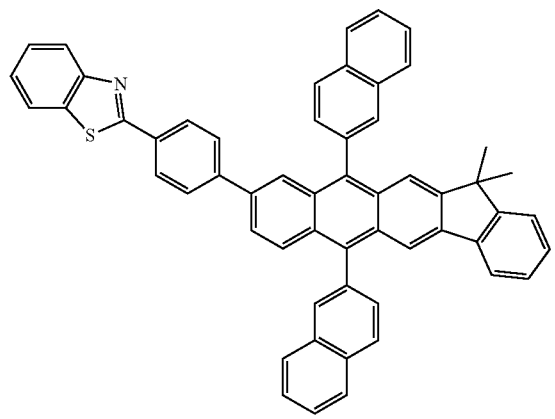
Inv128
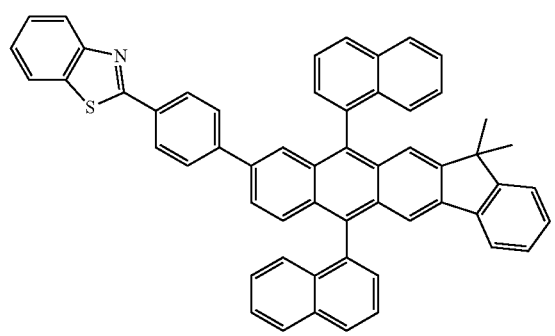
Inv-129
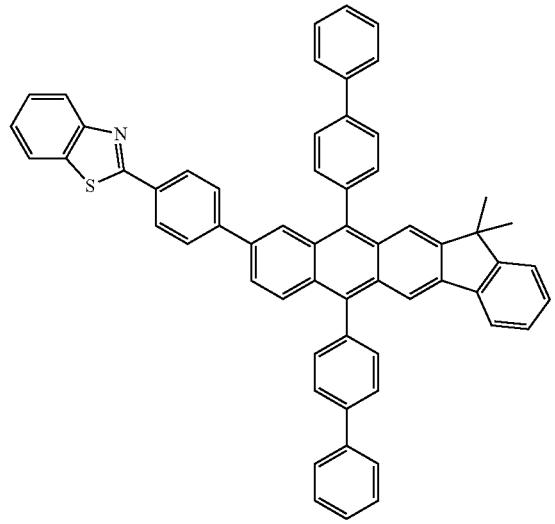
Inv-130
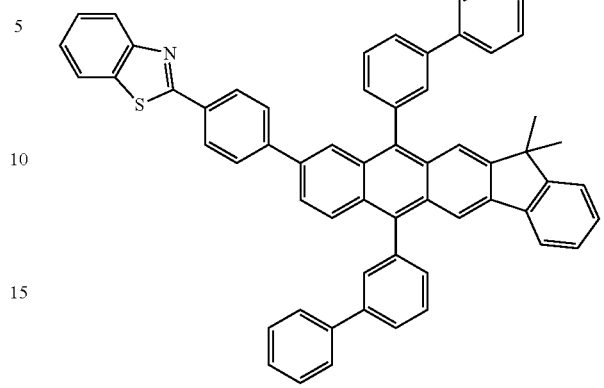
Inv-131
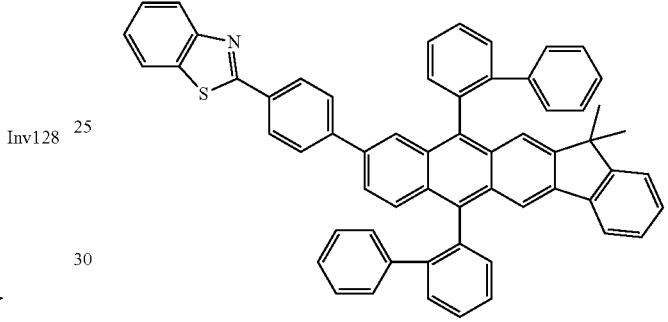
[Compound C]
Inv-132
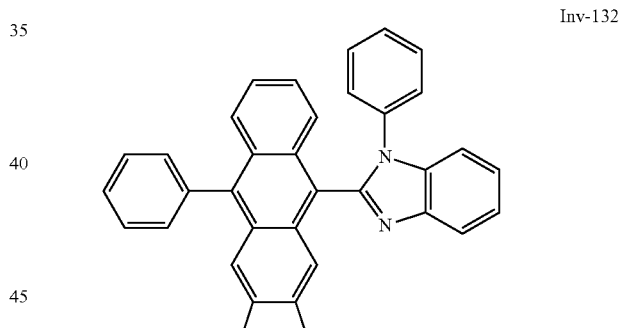
Inv-133
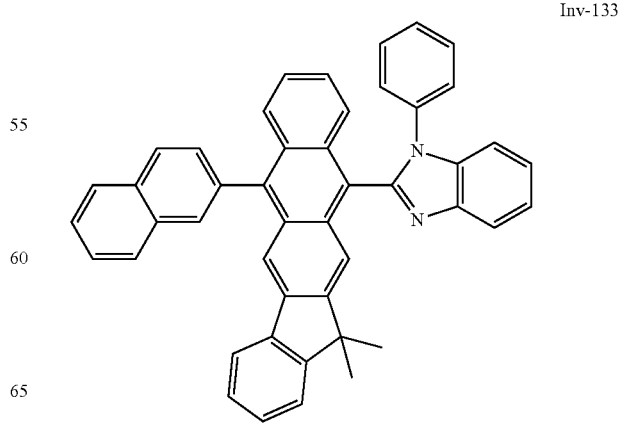

Inv-134
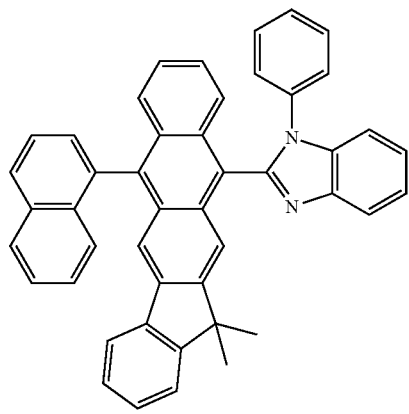
Inv-137
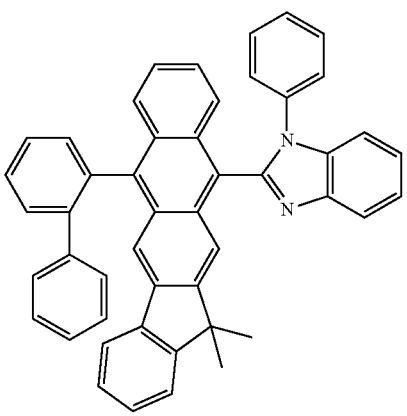
Inv-135
Inv-138
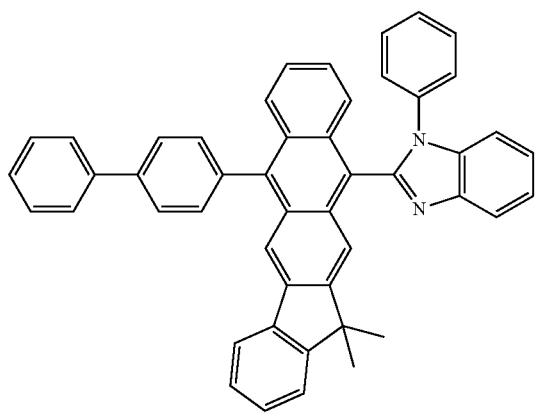
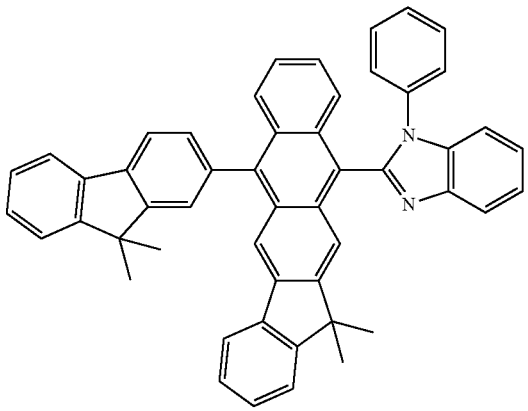
Inv-136
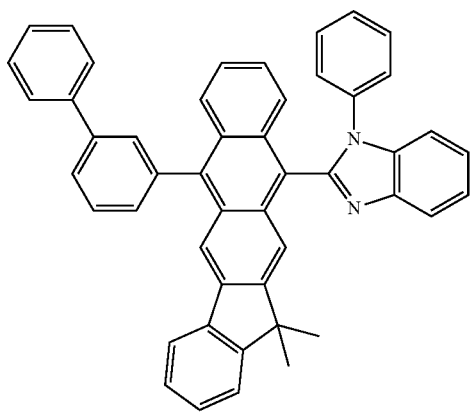
Inv-139

Inv-140
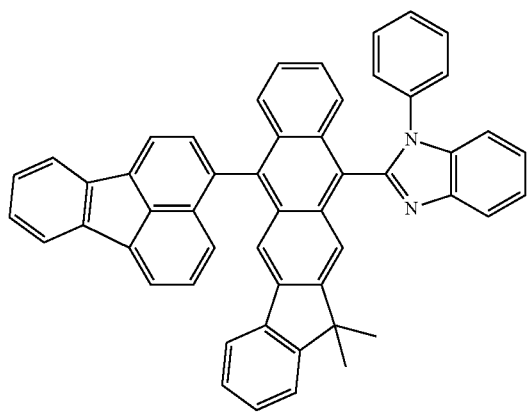
Inv-141
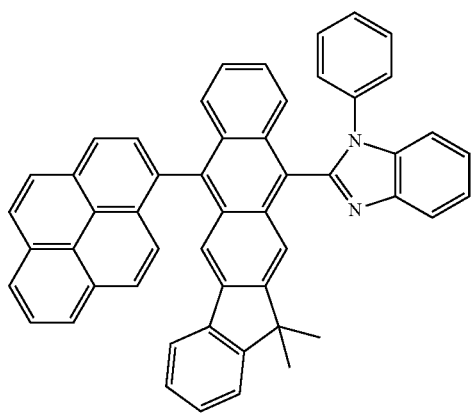
Inv-142
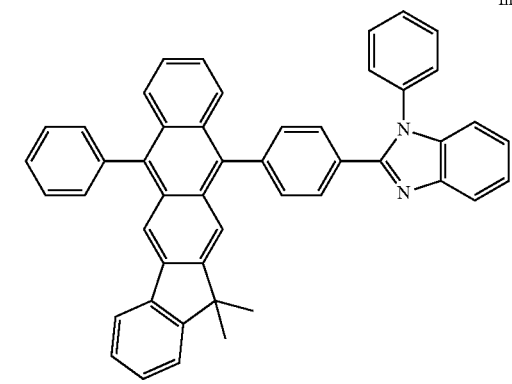
Inv-143
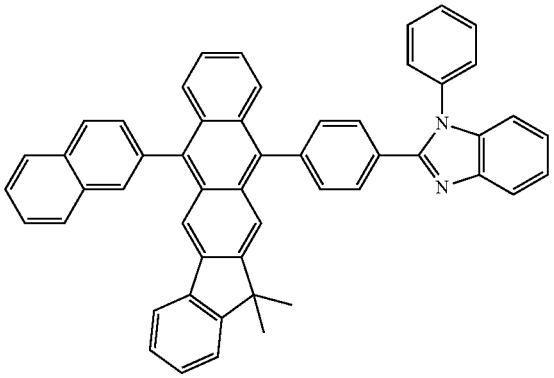
Inv-144
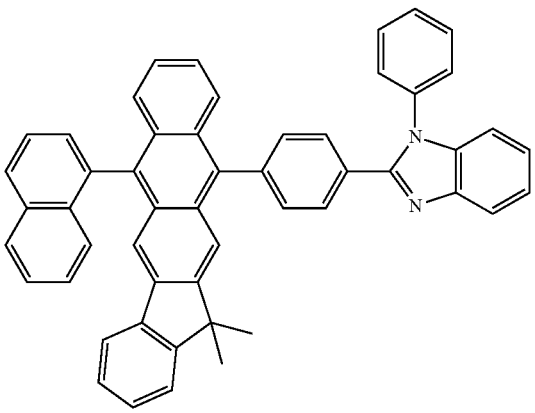
Inv-145
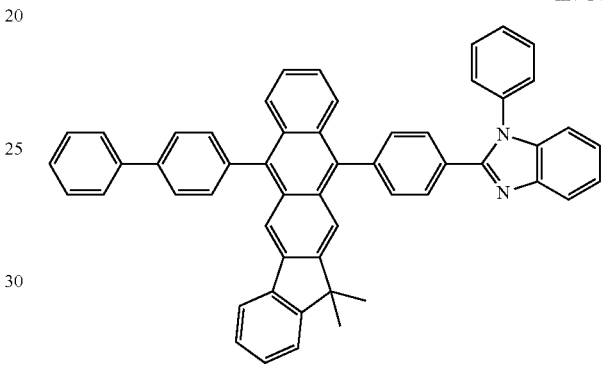
Inv-146
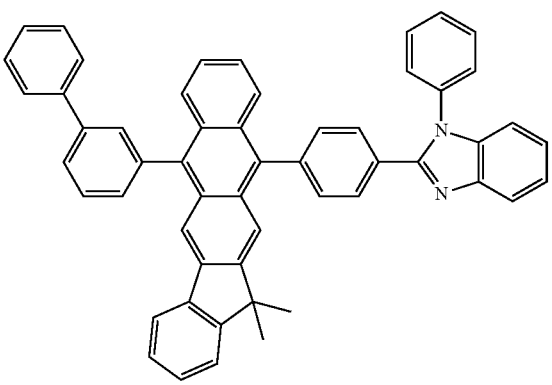
Inv-147
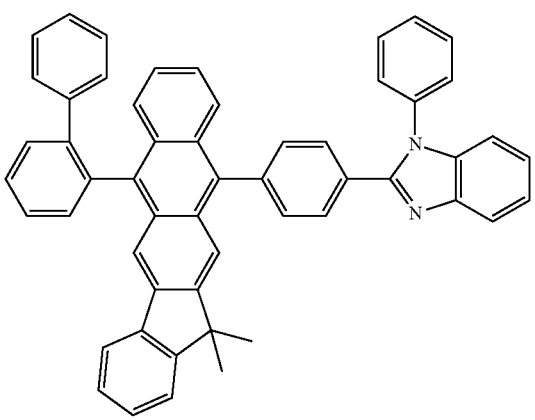

Inv-148
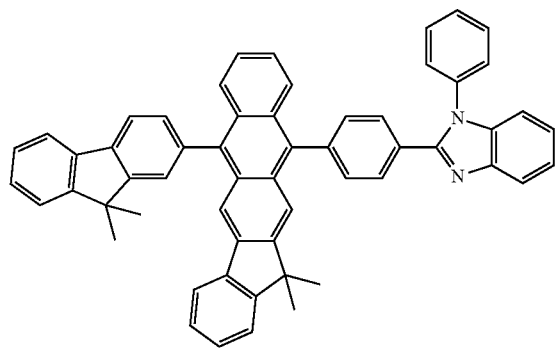
Inv-149
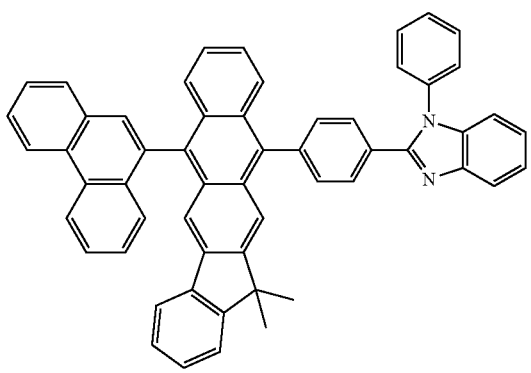
Inv-150
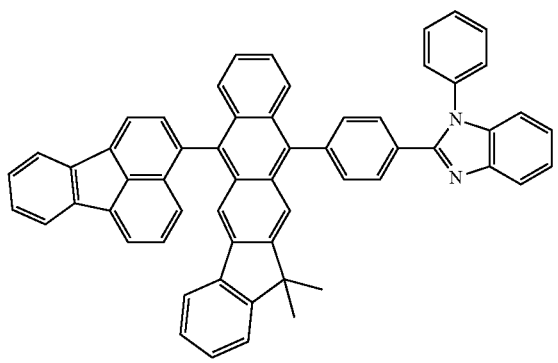
Inv-151
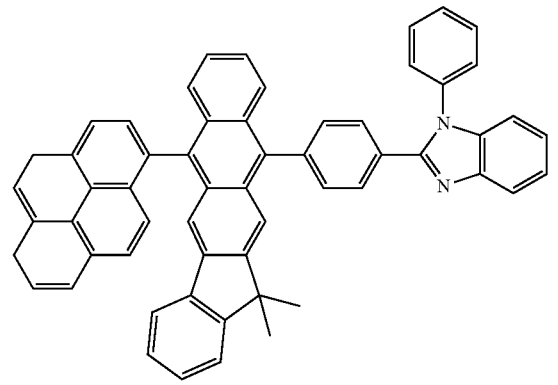
Inv-152
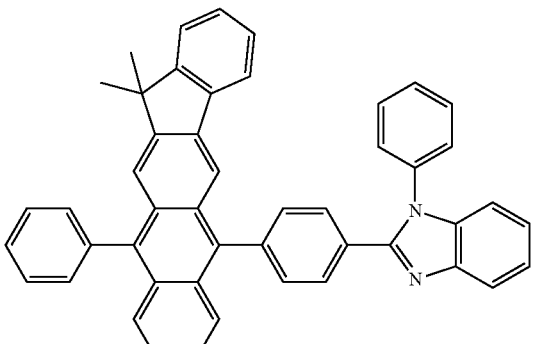
Inv-153
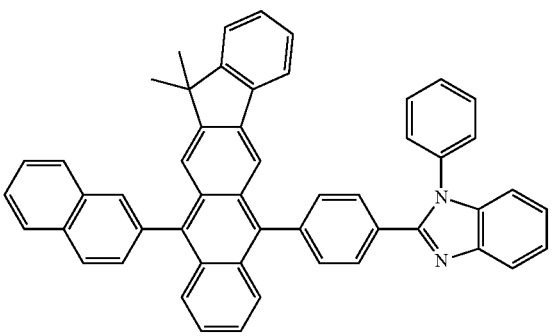
Inv-154
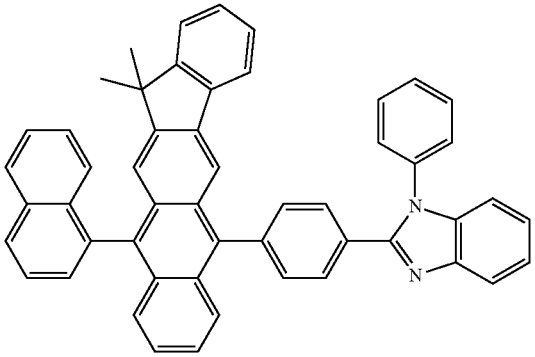
Inv-155
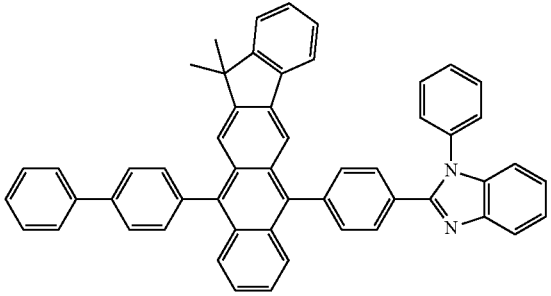

Inv-156
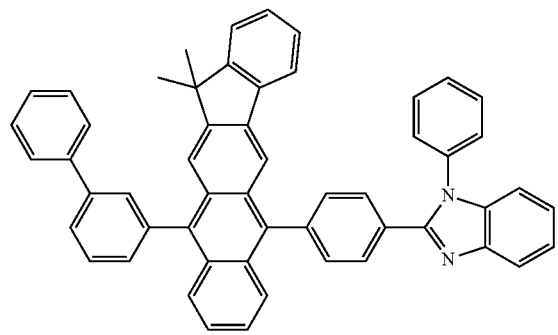
Inv-160
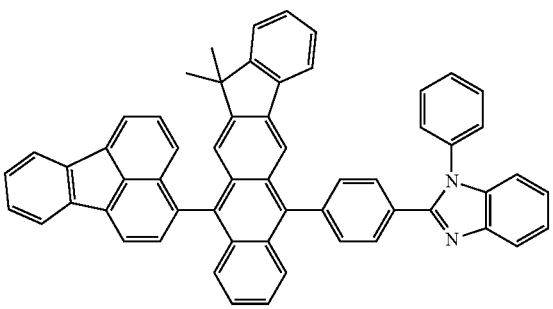
Inv-157
Inv-161
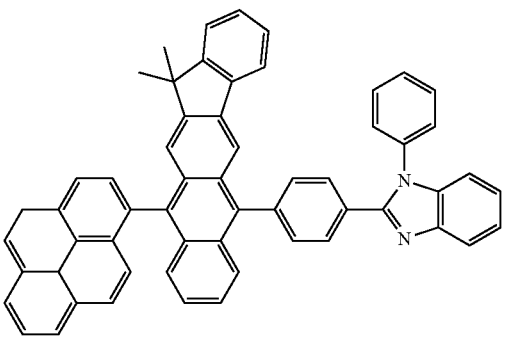
Inv-158
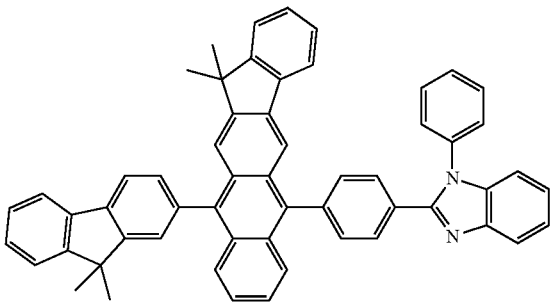
Inv-162
Inv-159
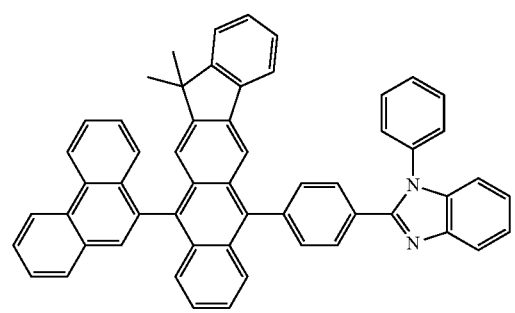
Inv-163
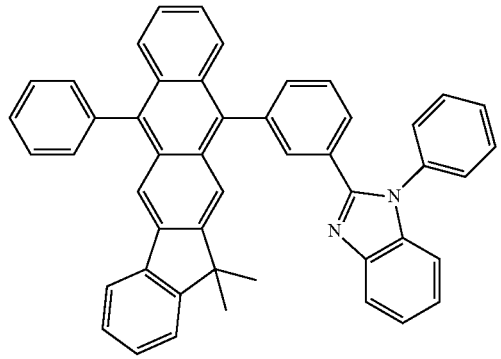

-continued
Inv-164
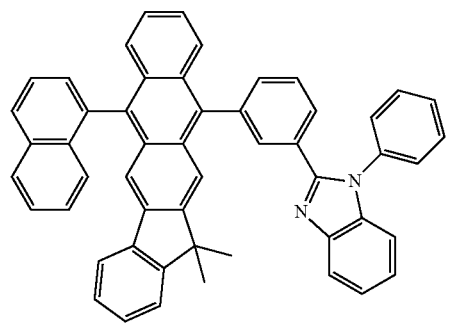
Inv-165
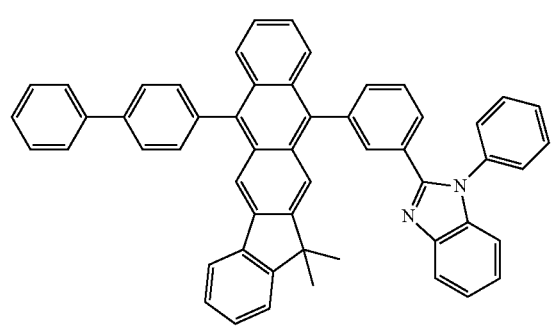
Inv-166
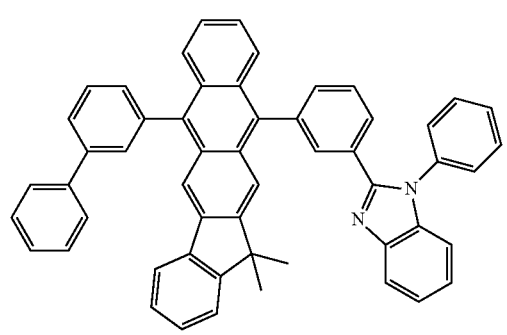
Inv-167
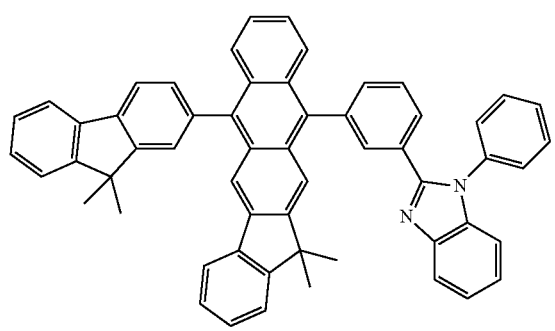
-continued
Inv-168
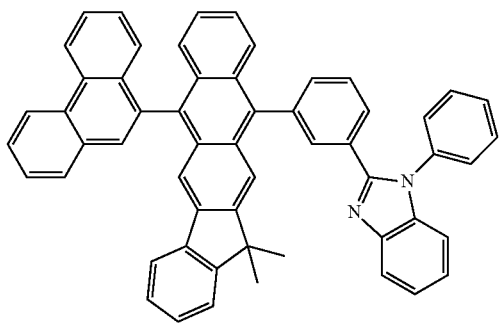
Inv-169
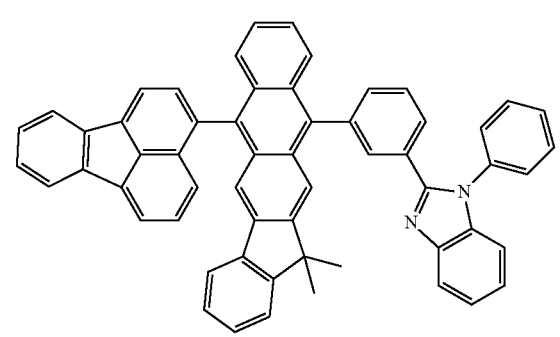
Inv-170
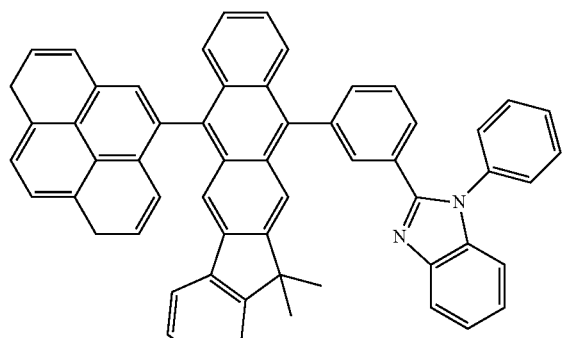
Inv-171
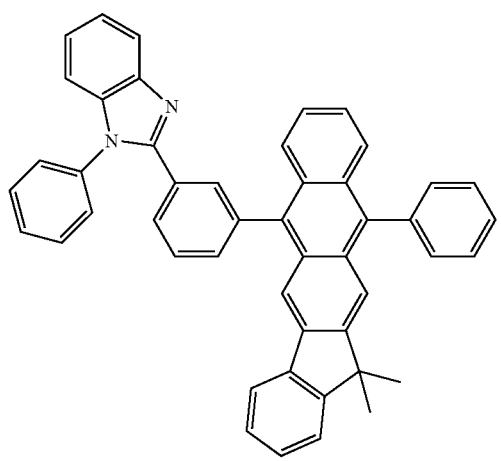

-continued
Inv-172
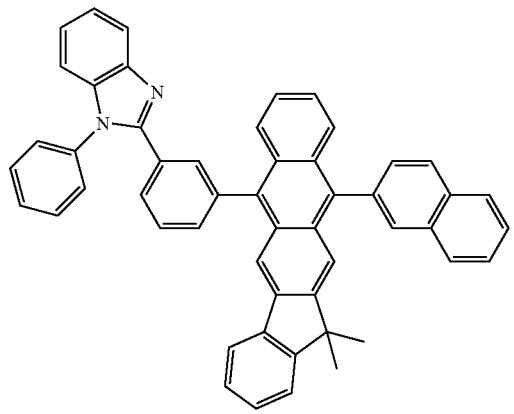
Inv-173
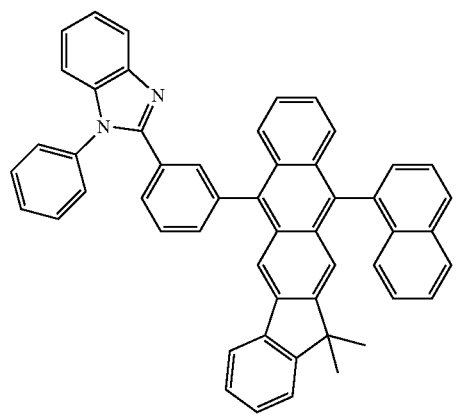
Inv-174
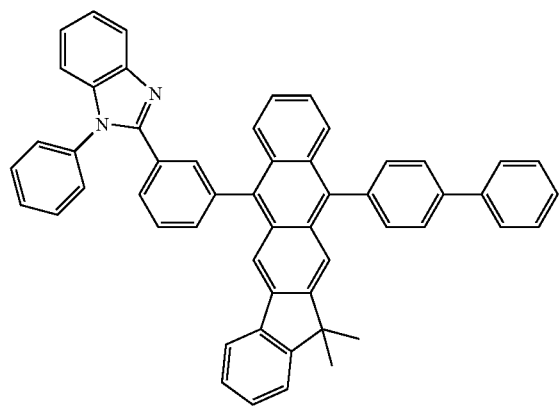
-continued
Inv-175
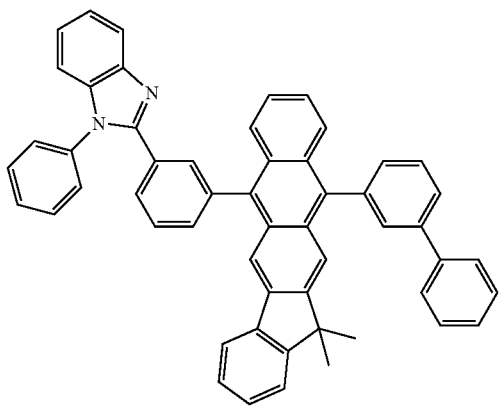
Inv-176
Inv-177
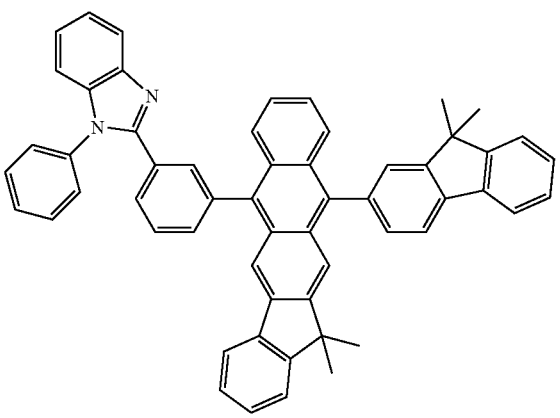

Inv-178
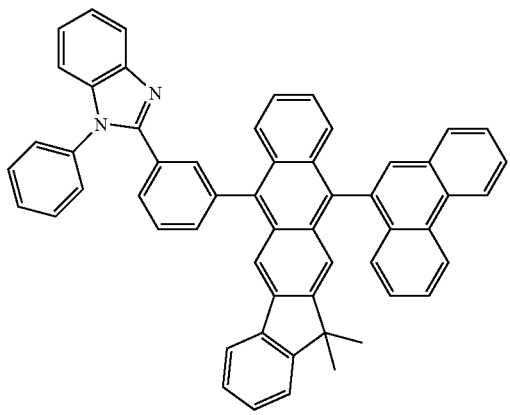
Inv-179
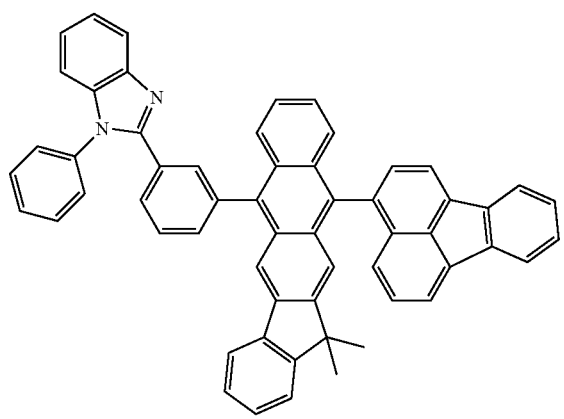
Inv-180
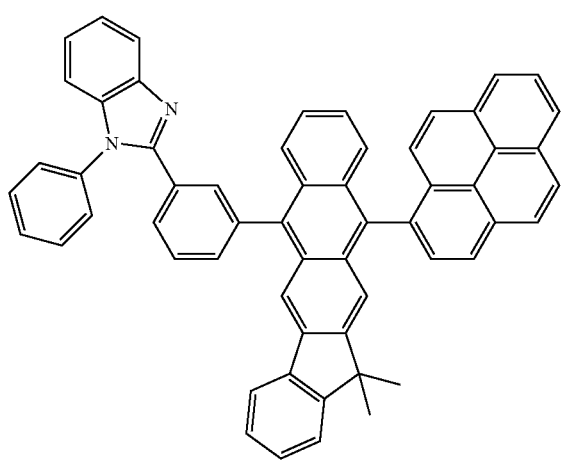
Inv-181
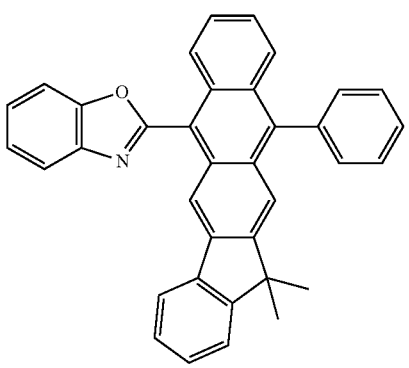
Inv-182
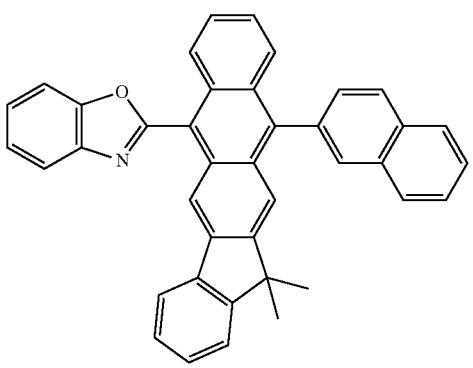
Inv-183
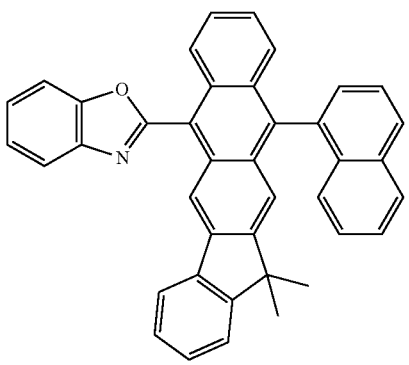
Inv-184
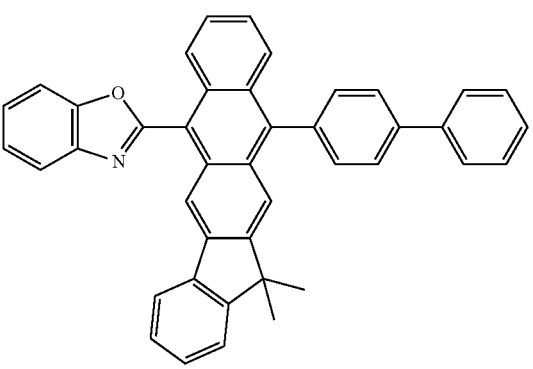

-continued
Inv-185
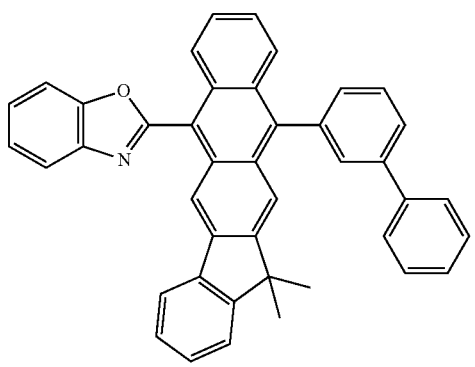
Inv-186
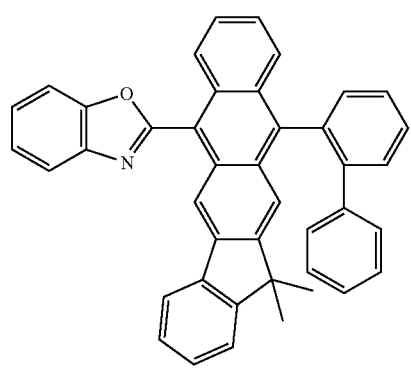
Inv-187
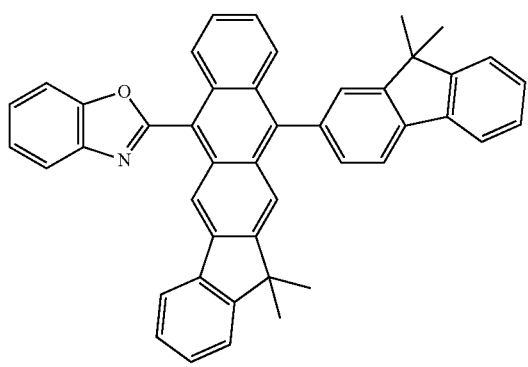
Inv-188
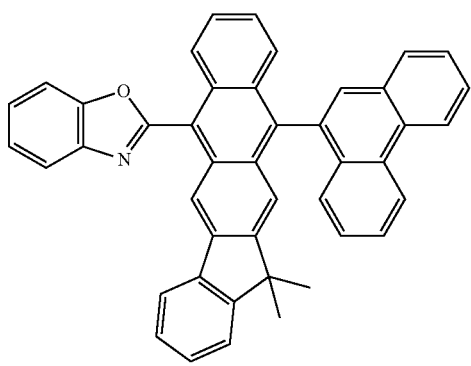
-continued
Inv-189
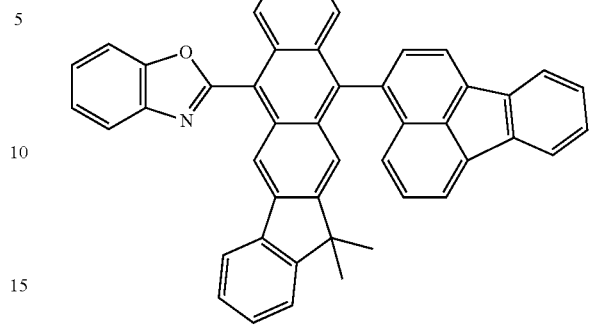
Inv-190
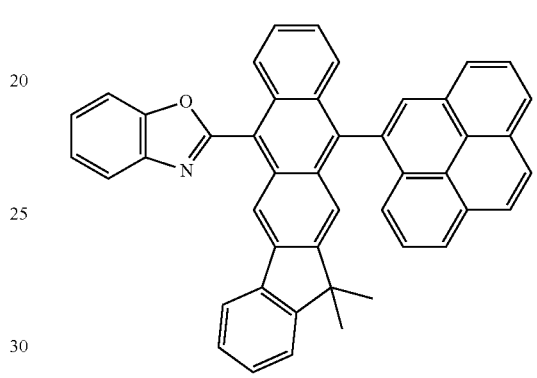
Inv-191
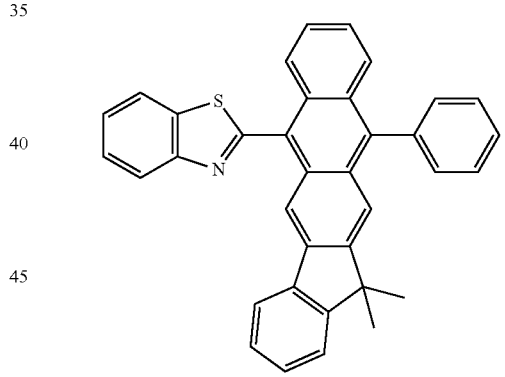
Inv-192
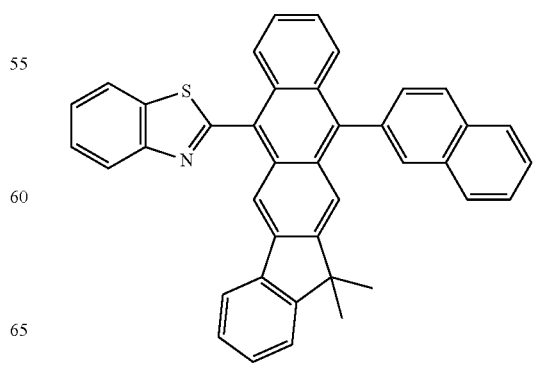

Inv-193
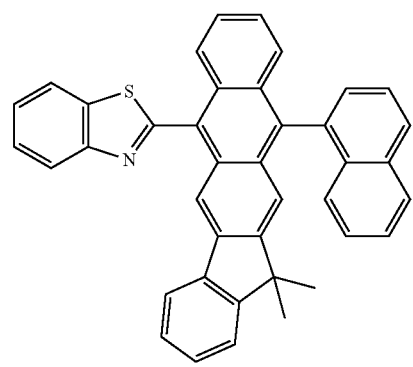
Inv-194
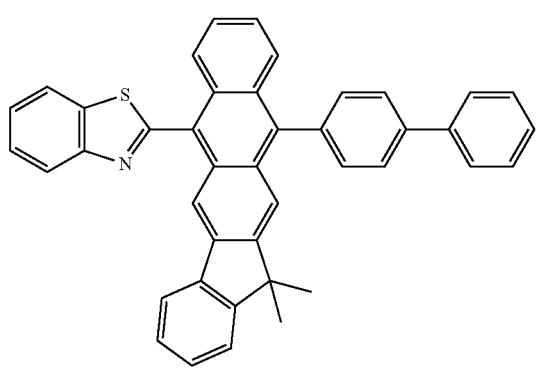
Inv-195
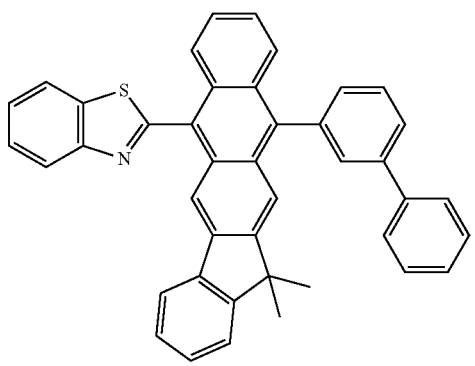
Inv-196
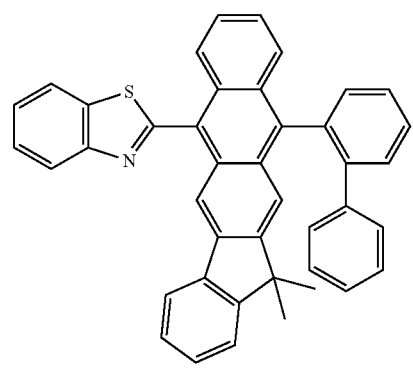
Inv-197
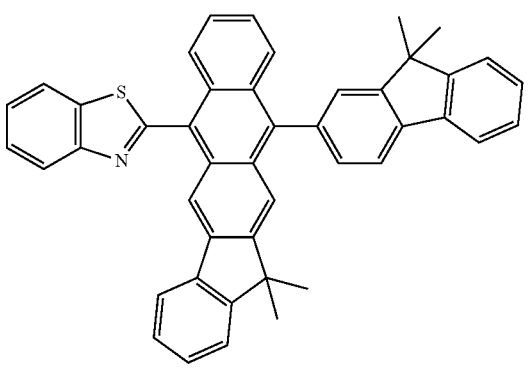
Inv-198
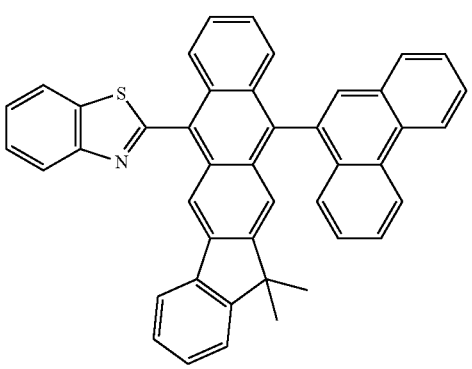
Inv-199
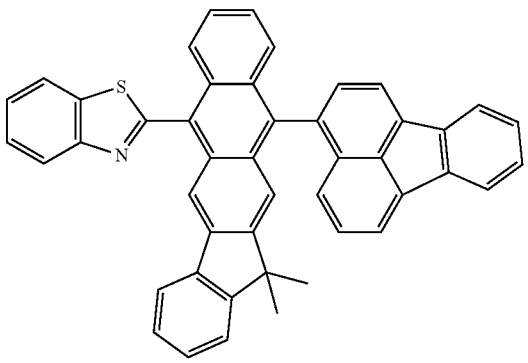
Inv-200
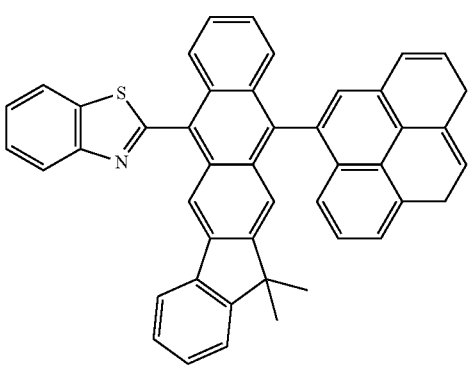

-continued
Inv-201
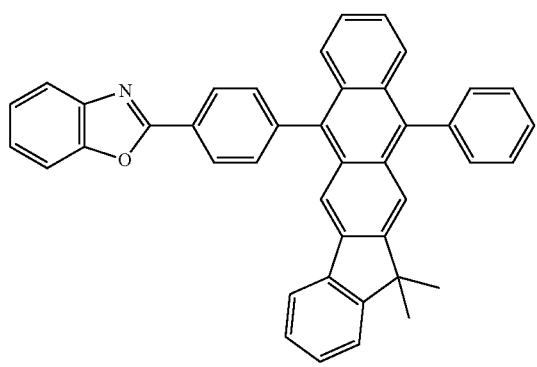
Inv-202
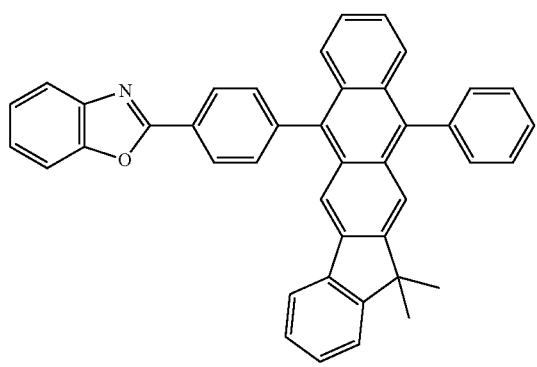
Inv-203
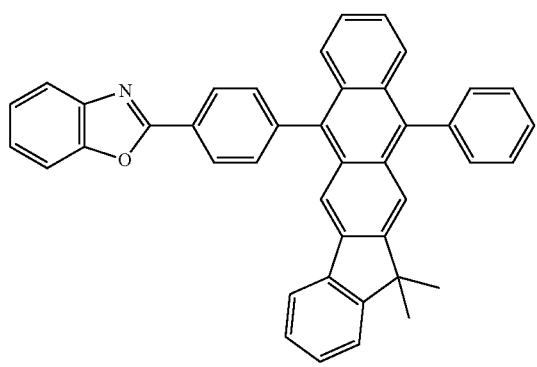
Inv-204
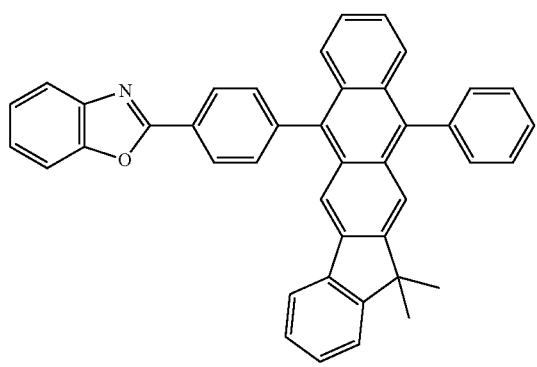
-continued
Inv-205
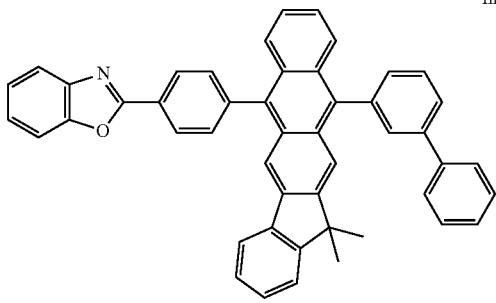
Inv-206
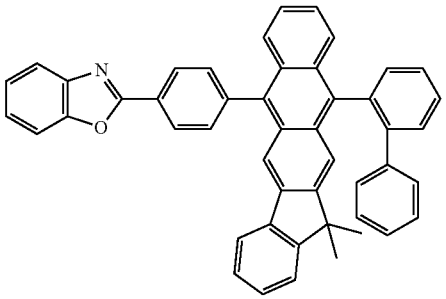
Inv-207
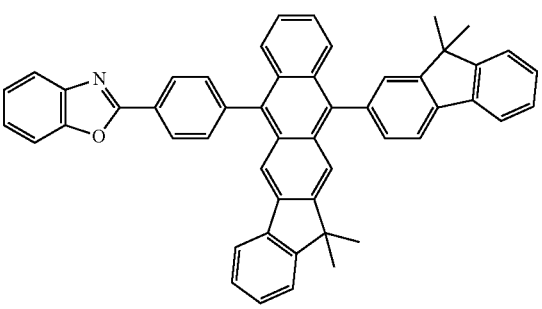
Inv-208
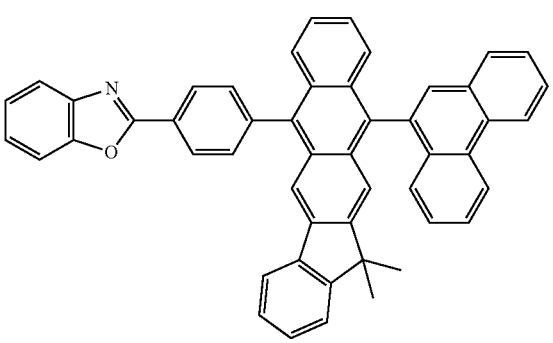
Inv-209
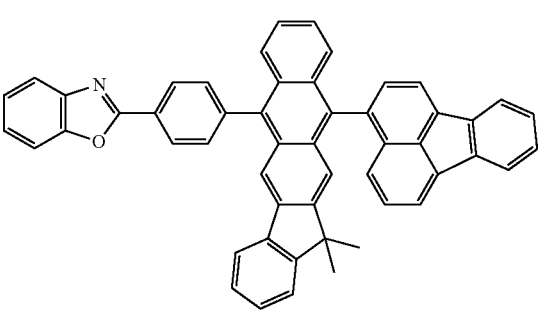

-continued
Inv-210
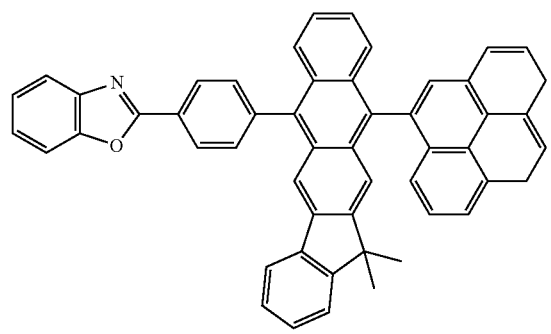
Inv-211
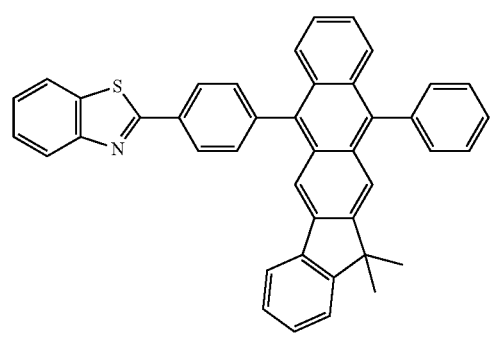
Inv-212
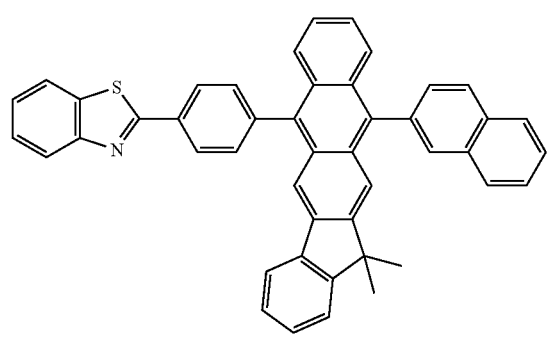
Inv-213
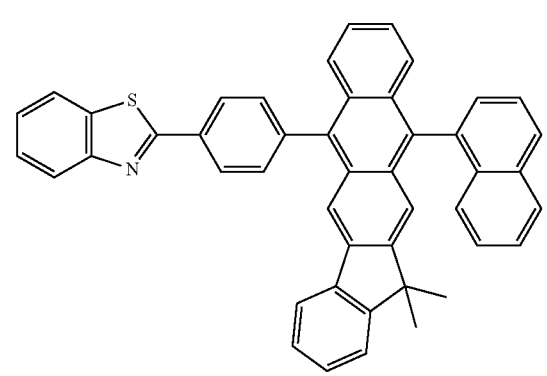
-continued
Inv-214
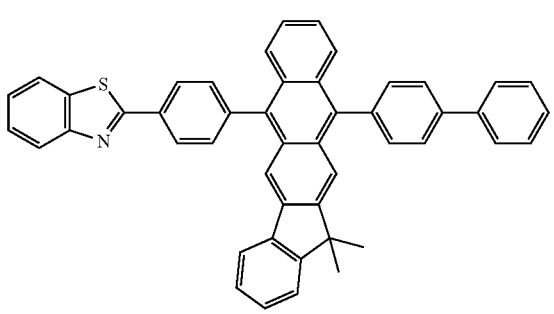
Inv-215
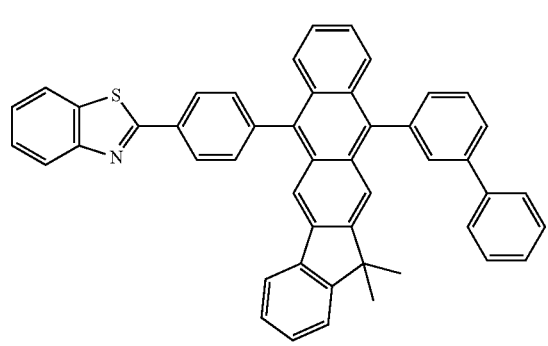
Inv-216
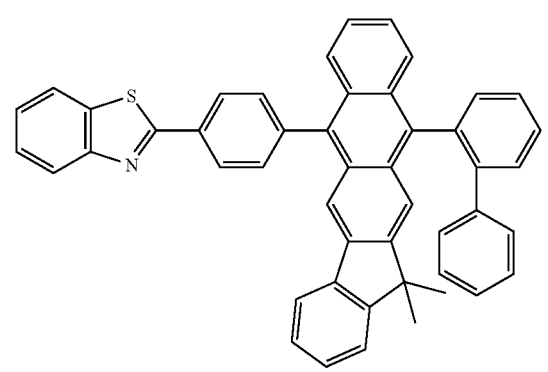
Inv-217
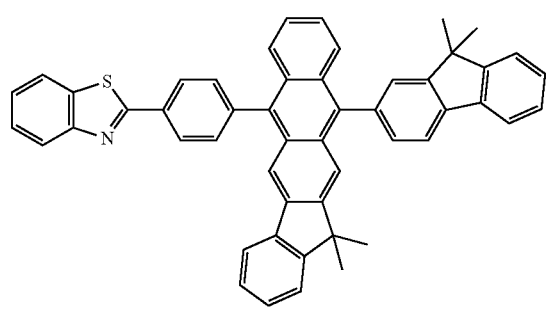

Inv-218
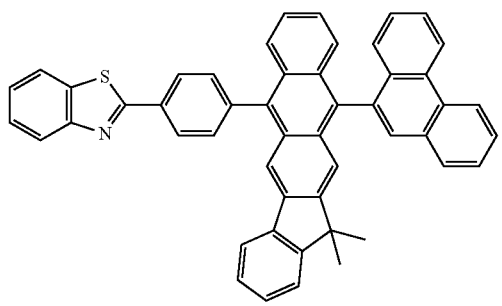
Inv-219
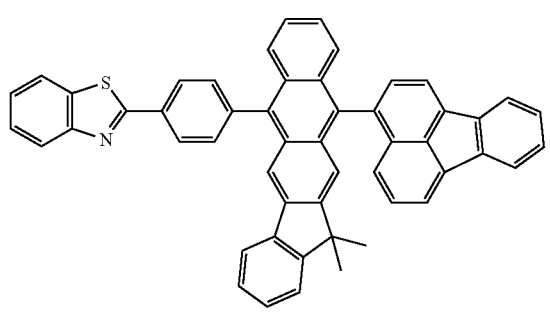
Inv-220
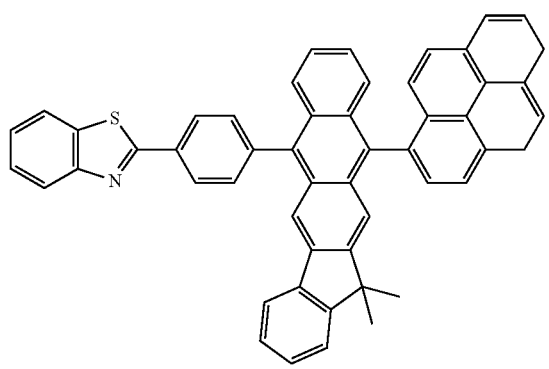
Inv-221
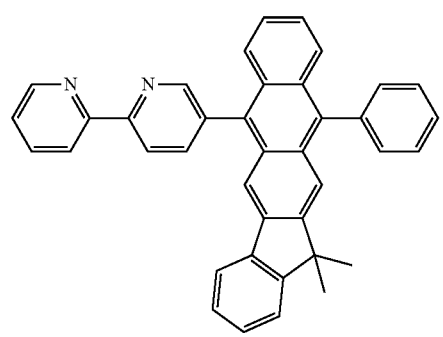
Inv-222
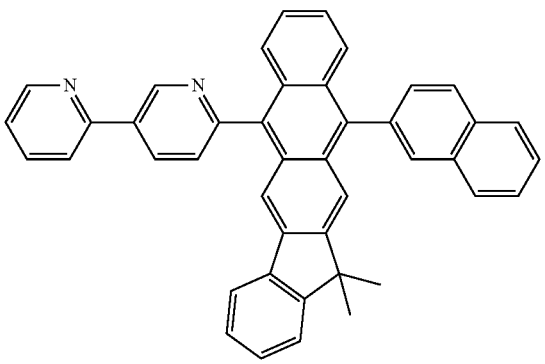
Inv-223
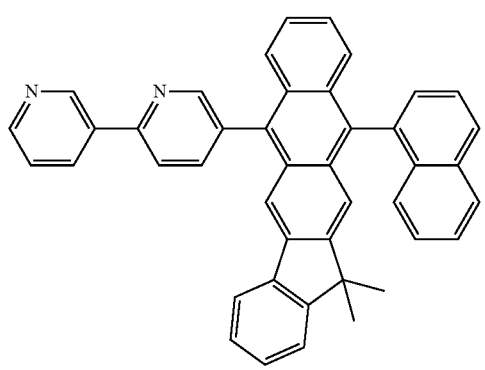
Inv-224
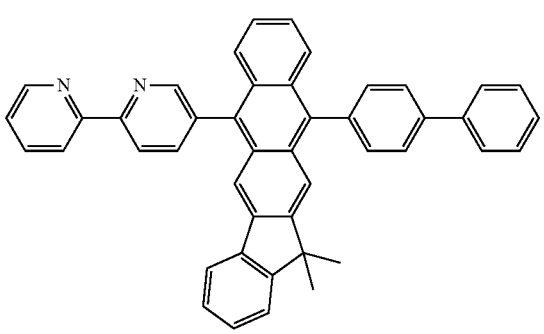
Inv-225
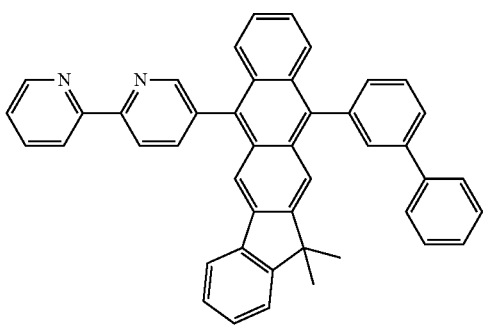

-continued
Inv-226
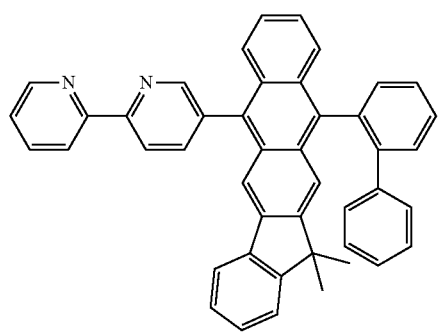
Inv-227
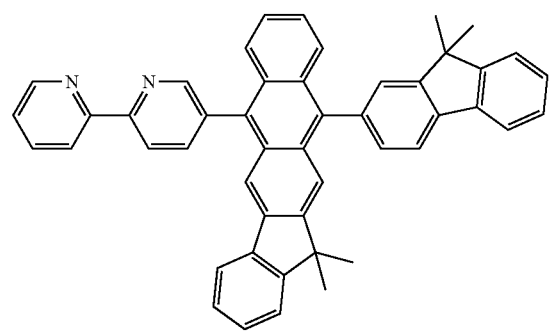
Inv-228
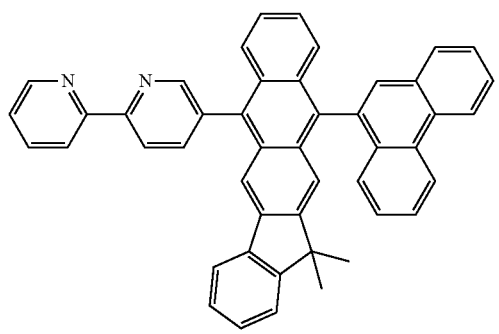
Inv-229
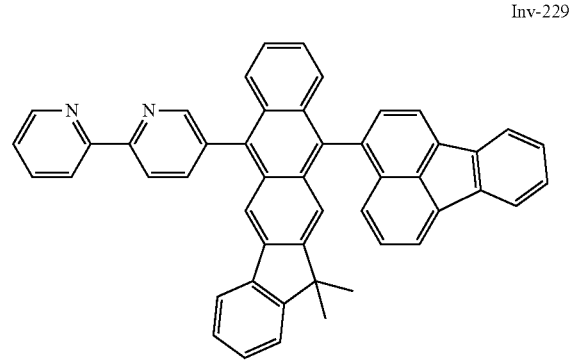
-continued
Inv-230
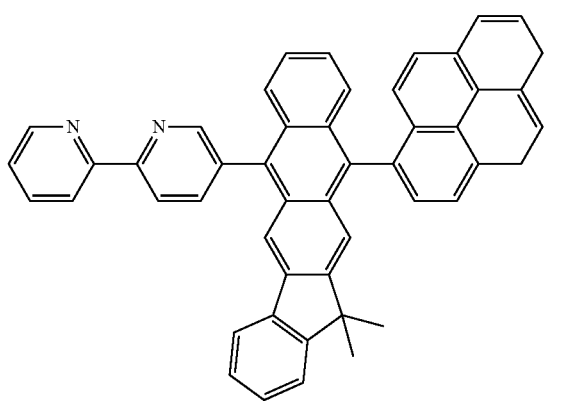
Inv-231
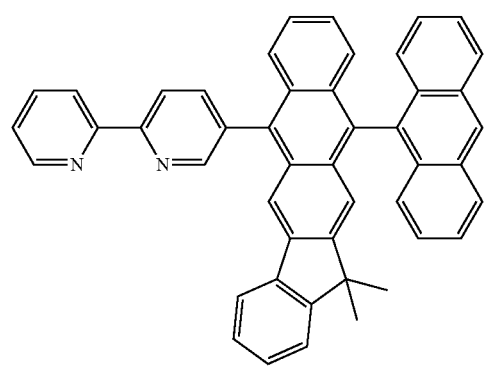
Inv-232
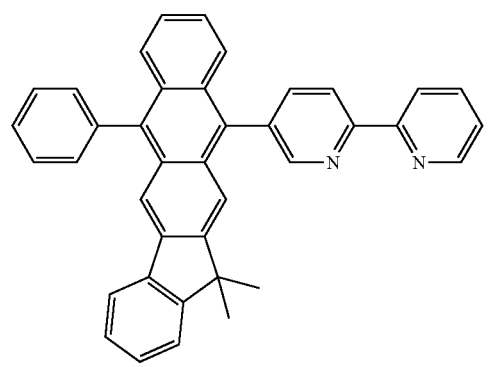
Inv-233
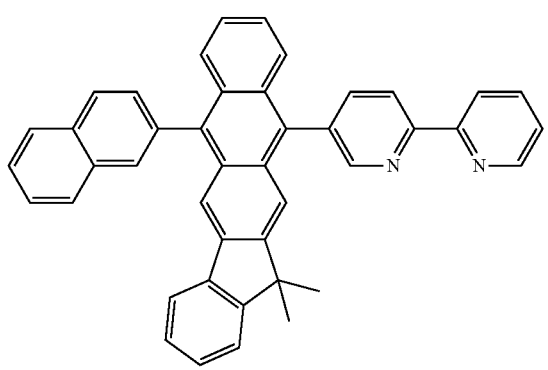

-continued
Inv-234
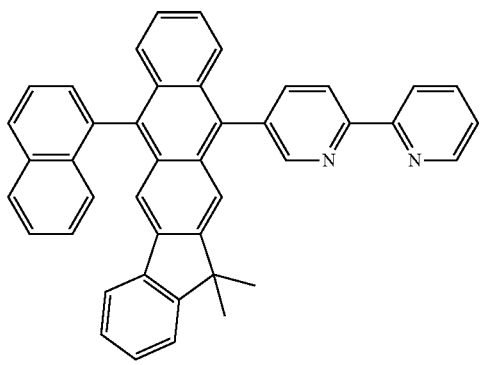
Inv-235
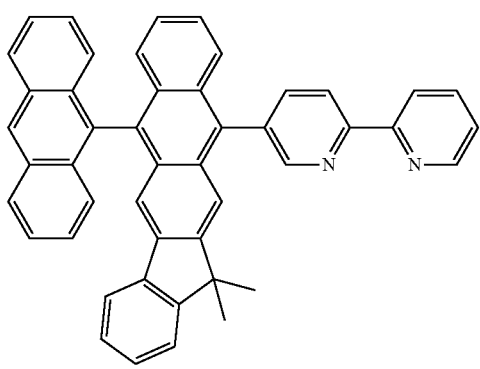
Inv-236
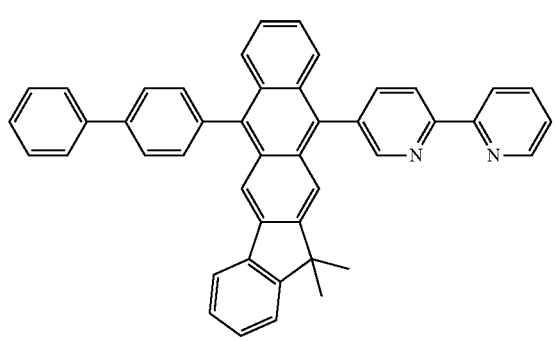
Inv-237
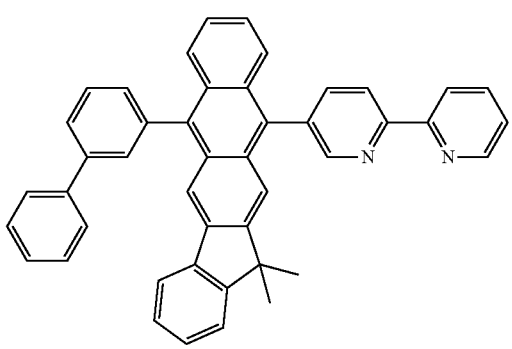
-continued
Inv-238
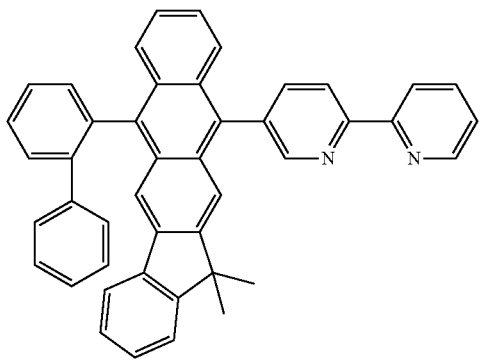
Inv-239
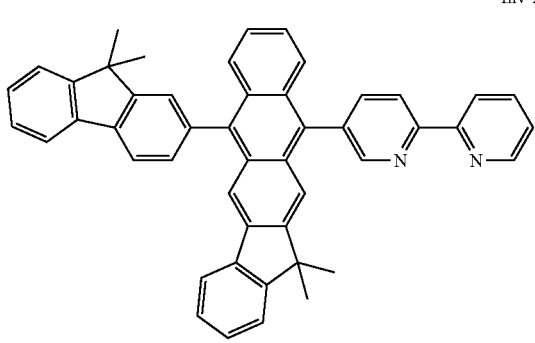
Inv-240
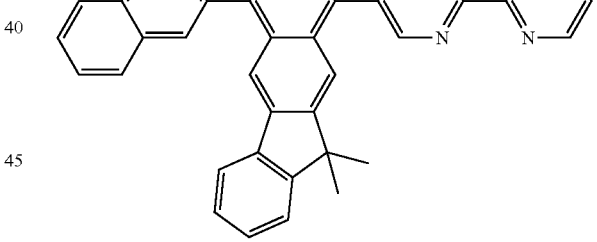
Inv-241
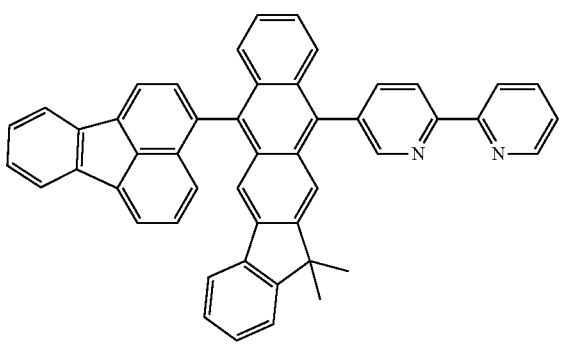

[Compound D]
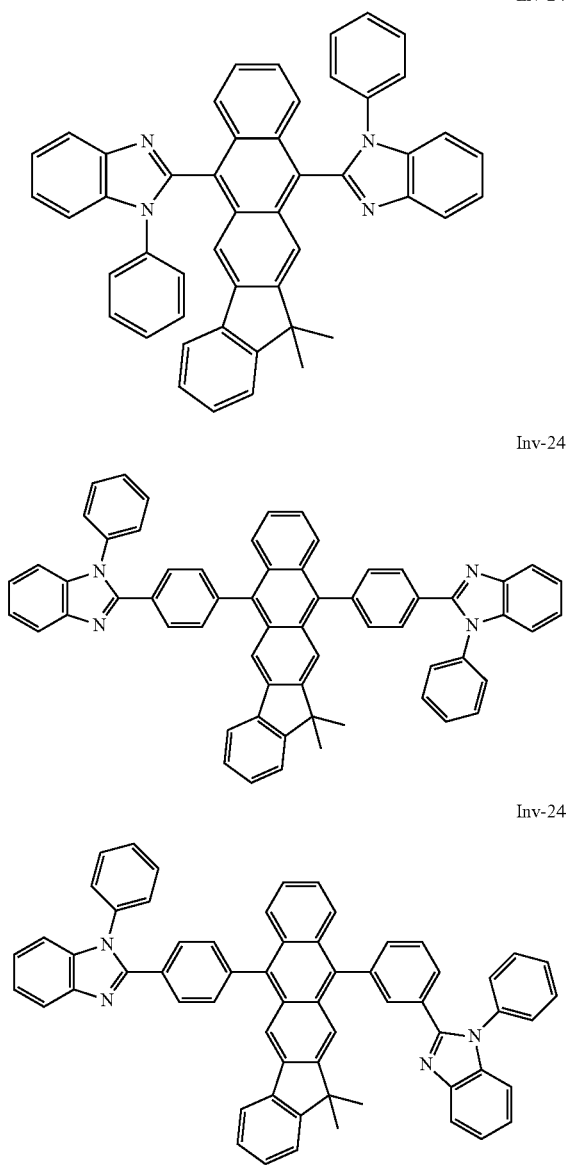
Inv-242
Inv-243
Inv-244
Inv-245
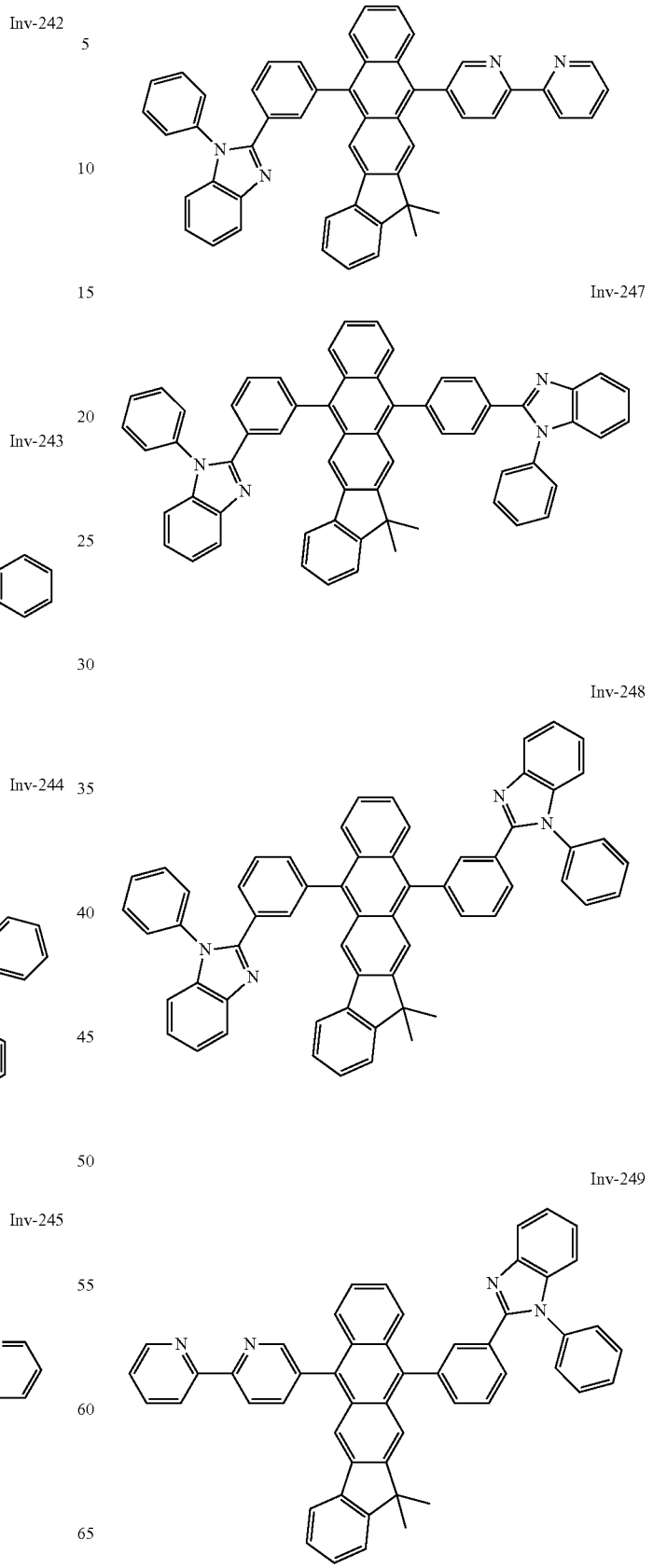
Inv-246
Inv-247
Inv-248
Inv-249

Inv-250
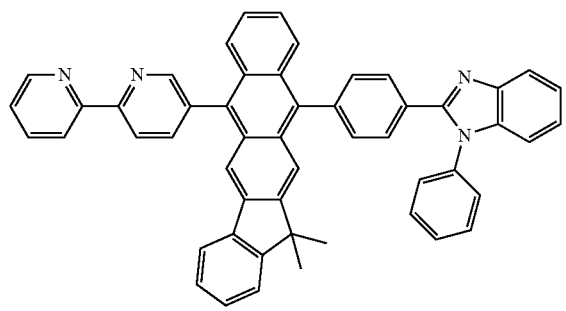
Inv-254
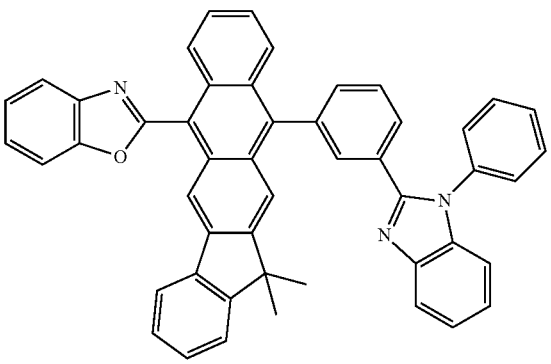
Inv-251
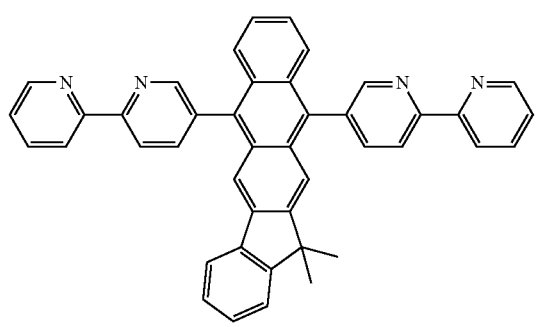
Inv-255
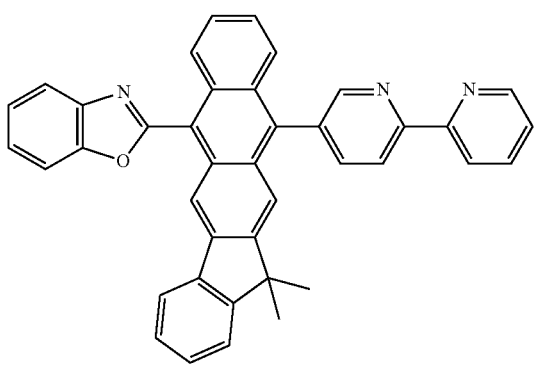
Inv-252
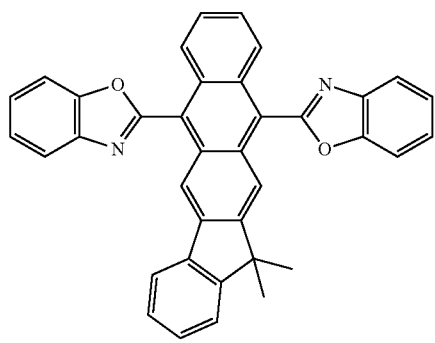
Inv-256
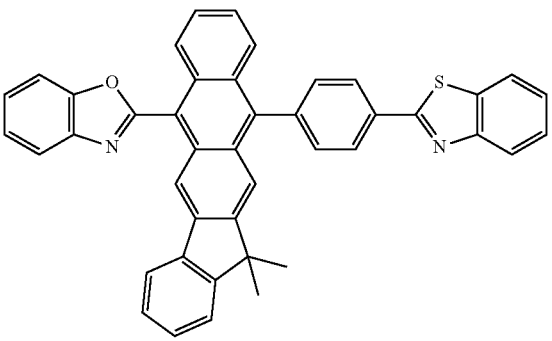
Inv-253
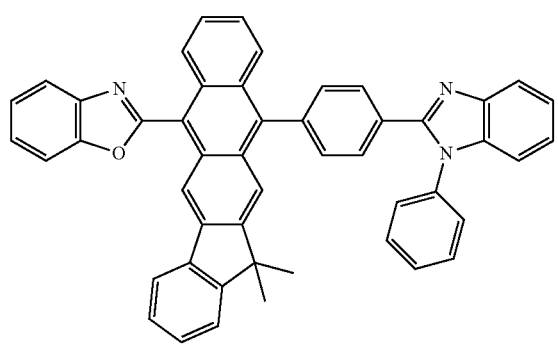
Inv-257
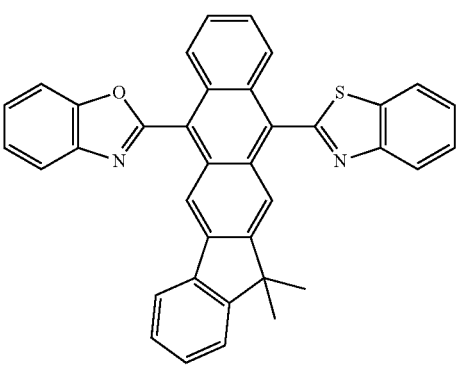

Inv-258
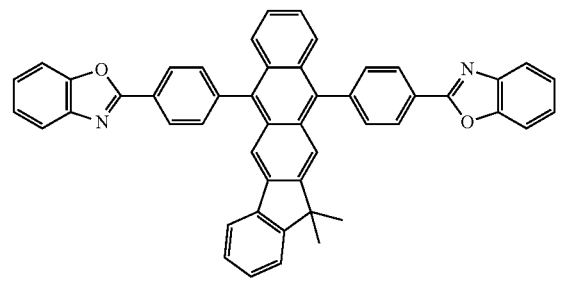
Inv-259
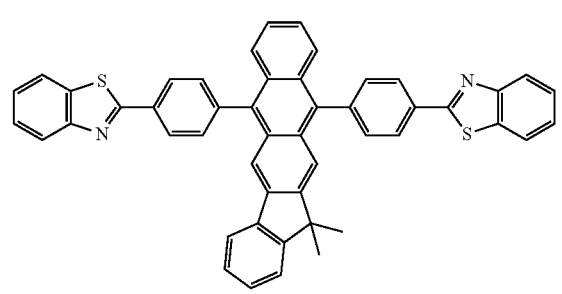
Inv-260
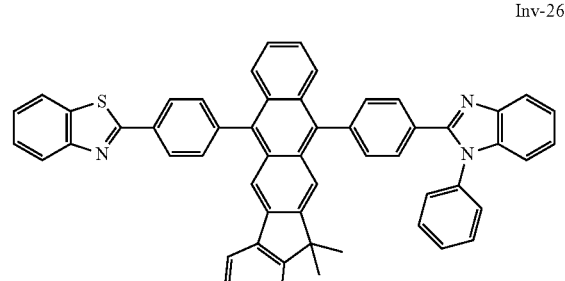
Inv-261
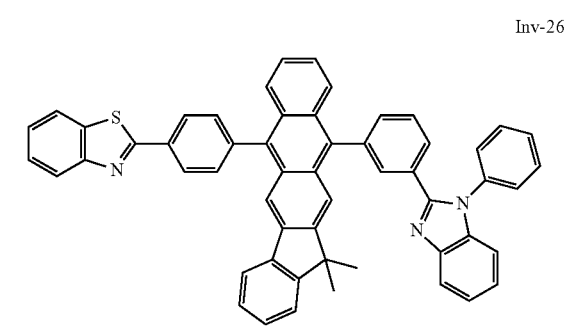
Inv-262
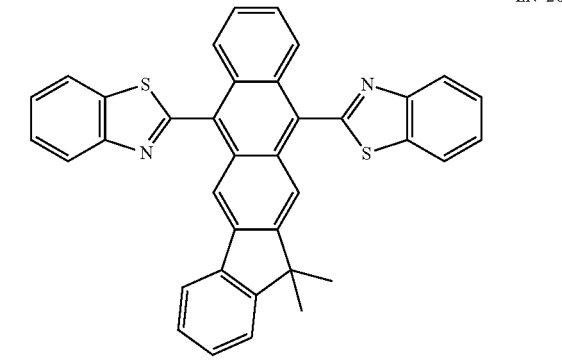
Inv-263
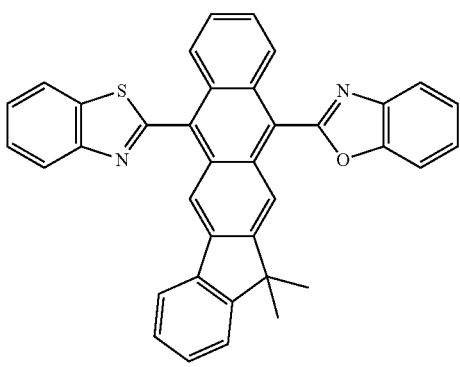
Inv-264
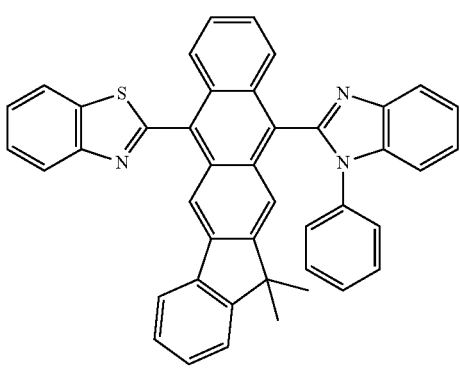
Inv-265
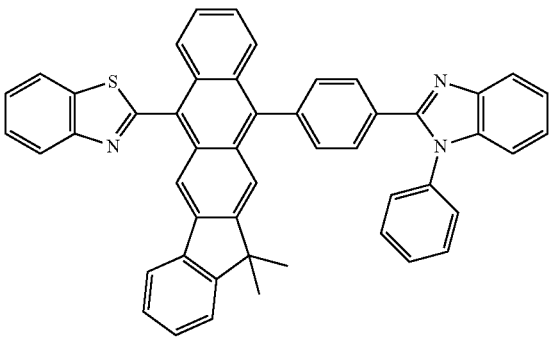
Inv-266
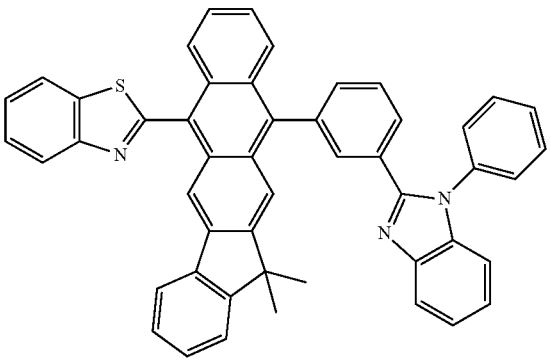

Inv-267
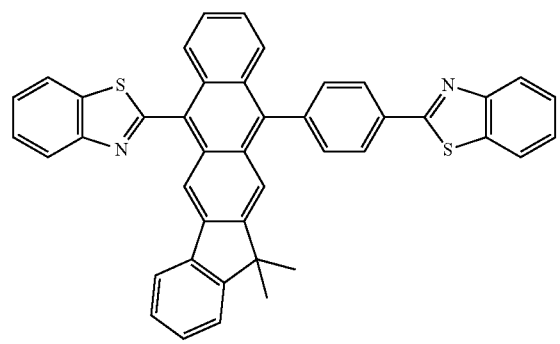
Inv-268
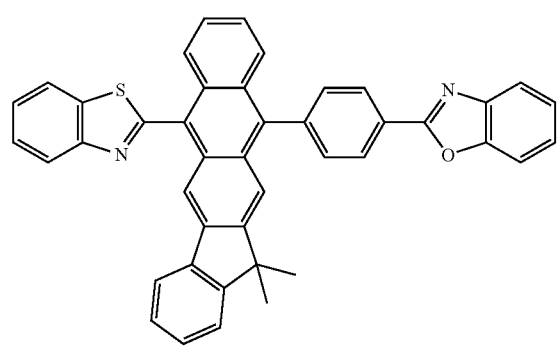
Inv-269
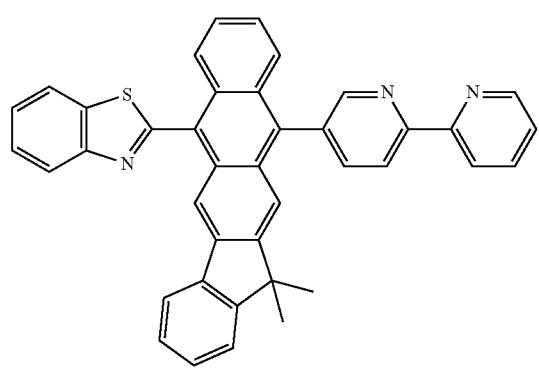
Inv-270
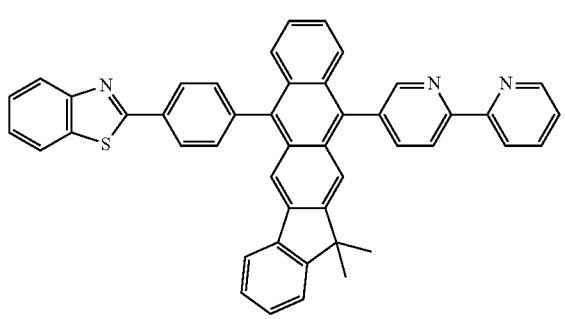
[Compound E]
Inv-271
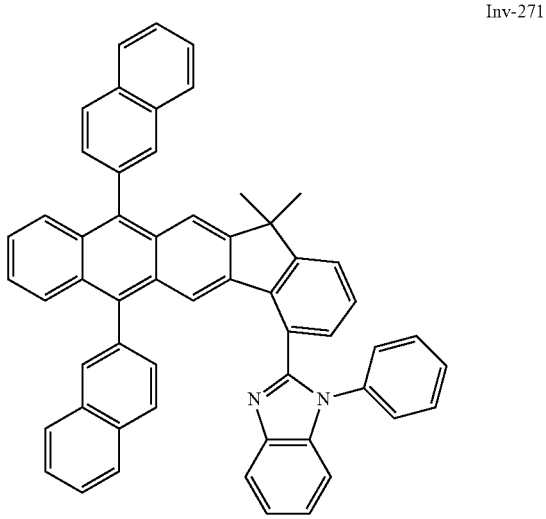
Inv-272
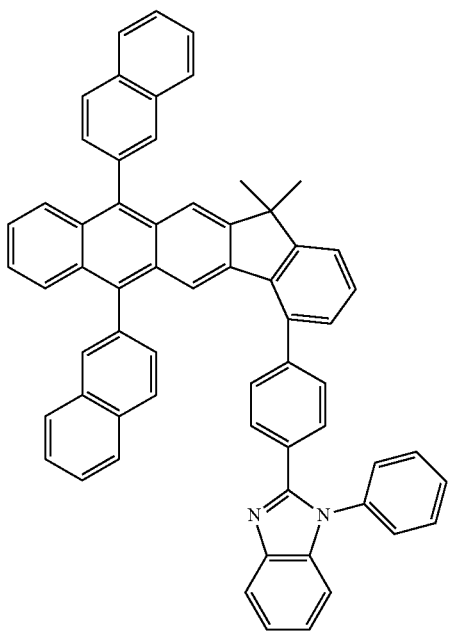

Inv-273
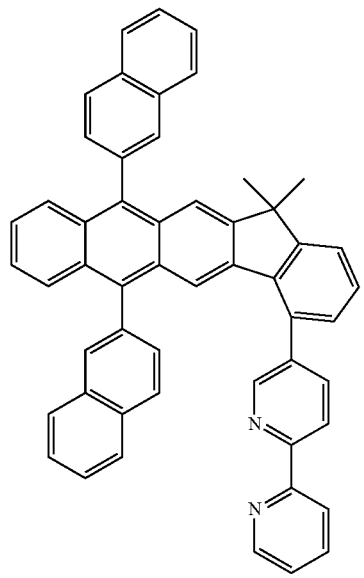
Inv-274
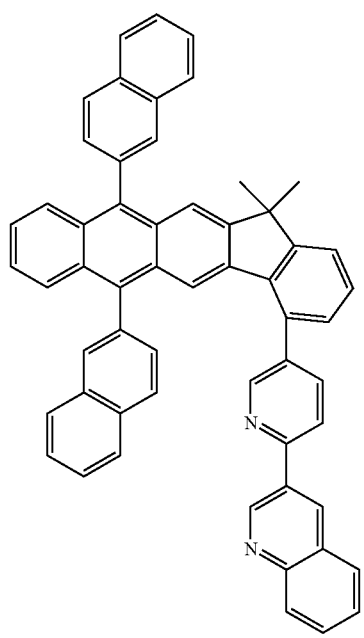
Inv-275
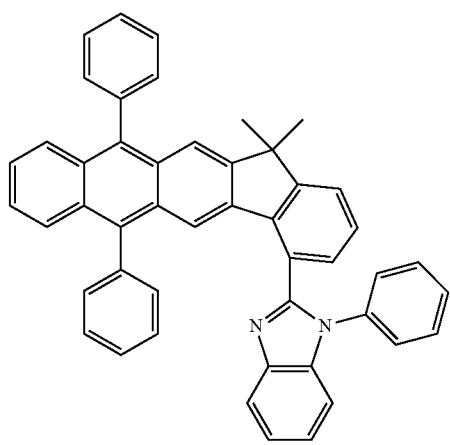
Inv-276
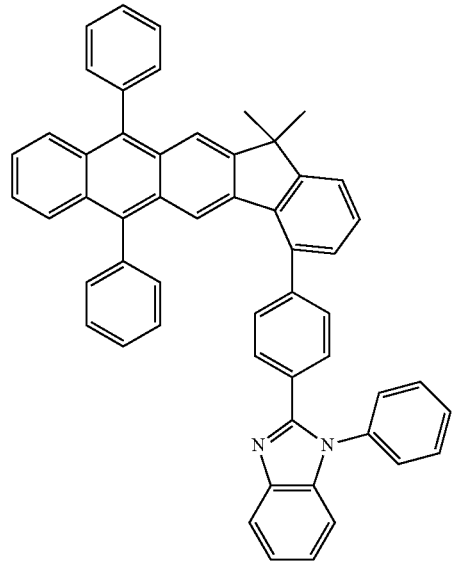
Inv-277
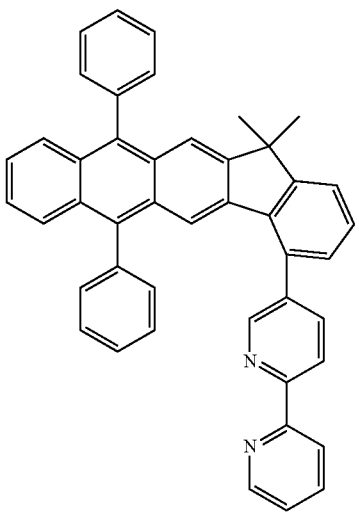
Inv-278
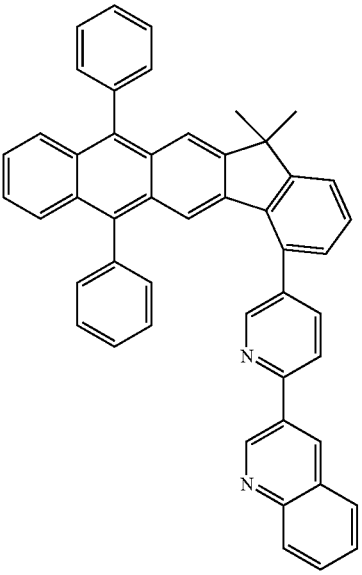

Inv-279
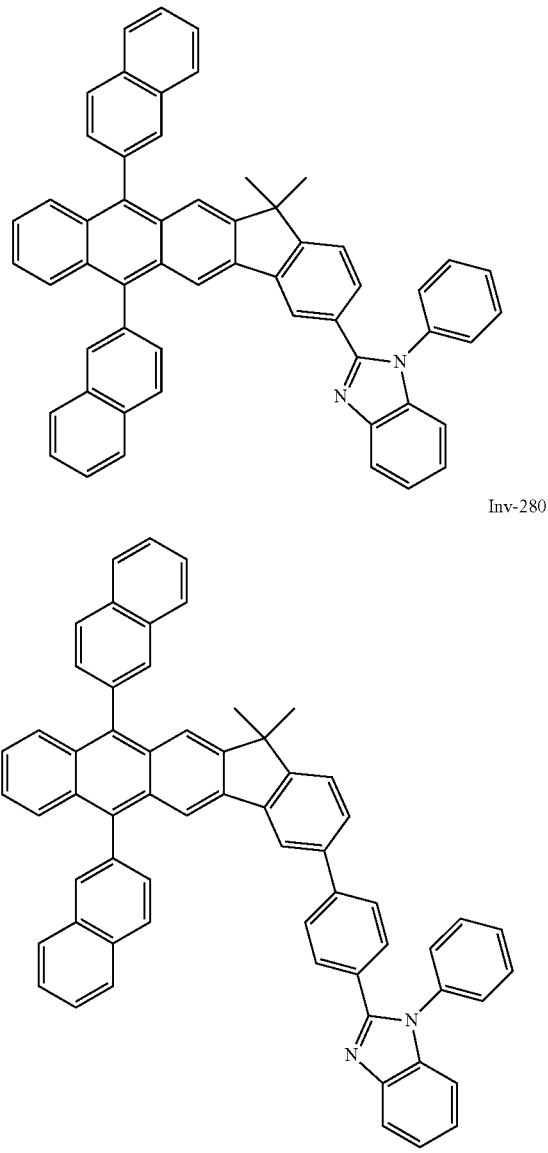
Inv-280
Inv-281
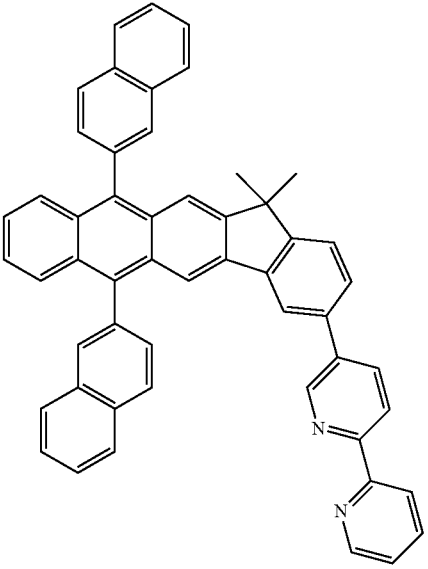
The reaction scheme 1 below is one example for preparing the above exemplified compounds according to the present invention, but the present invention is not limited thereto. The present invention may appropriately employ reactions and reagents, known in the art.
[Reaction Scheme 1]

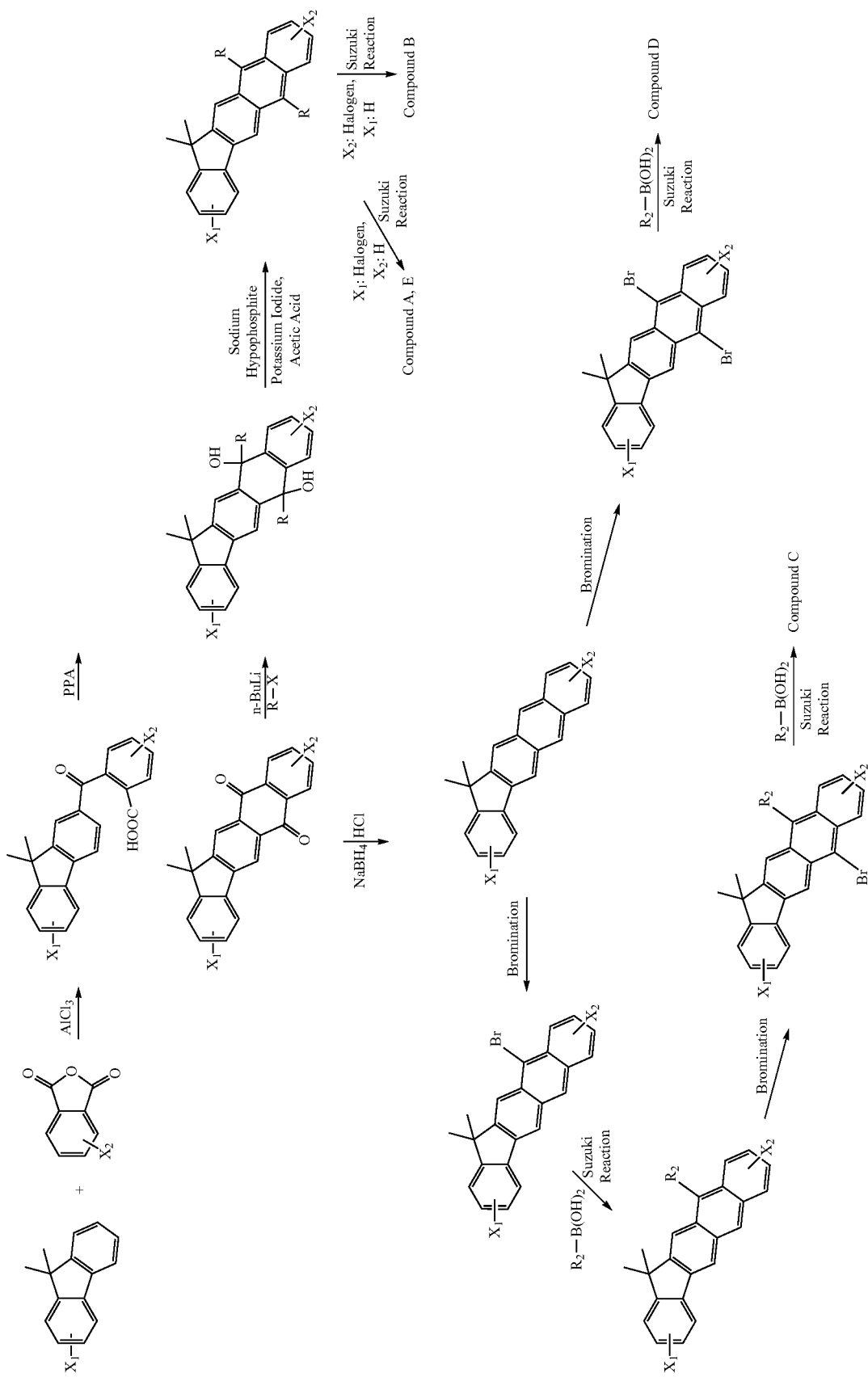

In Reaction Scheme 1, $R^1$ and $R^2$ are each independently selected from the group consisting of deuterium, an alkyl group of $C_1$~$C_{40}$, an alkenyl group of $C_2$~$C_{40}$, an alkynyl group of $C_2$~$C_{40}$, a cycloalkyl group of $C_3$~$C_{40}$, a heterocycloalkyl group of $C_3$~$C_{40}$, an arylalkyl group of $C_6$~$C_{40}$, an alkyloxy group of $C_1$~$C_{40}$, an aryloxy group of $C_5$~$C_{40}$, an aryl group of $C_5$~$C_{40}$, a heteroaryl group of $C_5$~$C_{40}$, a substituent represented by Formula 2, and a substituent represented by Formula 3.

The present invention provides an organic electroluminescent device which includes an anode; a cathode; and one or more organic material layers intervened between the anode and the cathode, wherein at least one layer of the organic material layers includes the compound represented by Formula 1 according to the present invention. Herein, one kind or two or more kinds of the compound represented by Formula 1 may be included in the organic material layer.

The organic material layer including the compound represented by Formula 1 of the present invention may include one or more of a hole injection layer, a hole transport layer, a light emitting layer, an electron transport layer, and an electron injection layer. Preferably, the compound represented by Formula 1 may be included, as an electron transport material or an electron injection/transport material, in the organic electroluminescent device. In this case, the organic electroluminescent device requires a low driving voltage, and is enhanced in luminous efficiency, luminance, thermal stability, and lifetime, etc. Accordingly, preferably, the organic material layer including the compound represented by Formula 1 is an electron transport layer.

Besides the organic material layer including the compound represented by Formula 1 of the present invention, the organic electroluminescent device according to the present invention also may include, a hole injection layer, a hole transport layer, a light emitting layer, an electron transport layer and/or an electron injection layer.

As a non-limiting example, the inventive organic electroluminescent device may be structured such that a substrate, an anode, a hole injection layer, a hole transport layer, a light-emitting layer, an electron transport layer and a cathode are sequentially stacked one onto another. Herein, the electron transport layer includes the compound represented by Formula 1. On the electron transport layer, an electron injection layer may also be disposed.

The inventive organic electroluminescent device may also be structured such that an anode, one or more organic material layers and a cathode are sequentially stacked, as described above, and an insulating layer or an adhesive layer is interposed between an electrode and an organic material layer.

In the inventive organic electroluminescent device, the organic material layer including the compound represented by Formula 1 may be formed by vacuum deposition or solution coating. Examples of the solution coating include spin coating, dip coating, doctor blading, inkjet printing, thermal transfer, etc., but are not limited thereto.

In the inventive organic electroluminescent device, organic material layers and electrodes may be formed of materials known in the art using a method known in the art except that at least one layer of the organic material layers includes the compound represented by Formula 1 of the present invention.

For example, a substrate may be a silicon wafer, quartz, a glass plate, a metal plate, a plastic film or sheet, etc.

An anode material may be a metal such as vanadium, chromium, copper, zinc, or gold, or an alloy thereof; metal oxide such as zinc oxide, indium oxide, indium tin oxide (ITO), indium zinc oxide (IZO); a metal-oxide complex such as $ZnO:Al$ or $SnO_2:Sb$; a conductive polymer such as polythiophene, poly(3-methylthiophene), poly[3,4-(ethylene-1,2-dioxy)thiophene] (PEDT), polypyrrole and polyaniline; carbon black, etc., but is not limited thereto.

A cathode material may be a metal such as magnesium, calcium, sodium, potassium, titanium, indium, yttrium, lithium, gadolinium, aluminum, silver, tin or lead, or an alloy thereof; a multi-layered material such as $LiF/Al$ or $LiO_2/Al$, but is not limited thereto.

Materials for a hole injection layer, a hole transport layer and a light emitting layer are not particularly limited, and may be materials commonly known in the art.

Hereinafter, the present invention will be described more specifically with reference to the following examples. The following examples are only for illustrative purposes and are not intended to limit the scope of the invention.

Synthesis Example 1

Preparation of 2-bromo-9,9-dimethyl-9H-fluorene 2-bromo-9H-fluorene (44.1 g, 0.18 mol) was placed in a flask (1 L), and dimethylsulfoxide (500 ml) was added thereto. Then, KOH (94.25 g, 1.443 mol) dissolved in distilled water (20 ml) was added. At 0° C., Iodomethane (76.85 g, 0.541 mol) was gradually dropped, and the reaction mixture was stirred at room temperature. After the reaction was terminated, the reaction solution was added to distilled water (1 L). After stirring for 30 mins, the resultant solid was filtered, and purified by column chromatography to provide 2-bromo-9,9-dimethyl-9H-fluorene (34 g, yield=96.9%).

GC-Mass (theoretical value: 272.02 g/mol, measured value: 272 g/mol)

Synthesis Example 2

Preparation of 2-(7-bromo-9,9-dimethyl-9H-fluorene-2-carbonyl)benzoic acid 2-bromo-9,9-dimethyl-9H-fluorene (40 g, 0.146 mol) and phthalic anhydride (23.8 g, 0.161 mol) were placed in a reaction vessel and dichloromethane (1 l) was added thereto. Then, aluminum chloride (29.2 g, 0.219 mol) was gradually added at 0° C., and the reaction mixture was stirred at room temperature for 12 hours. After the reaction was terminated, distilled water was gradually added, and the reaction solution was extracted with dichloromethane and 3 times washed with distilled water. After solvent removal, the resultant solid was placed in a hexane(2 l)-containing vessel, washed, filtered and dried to give 2-(7-bromo-9,9-dimethyl-9H-fluorene-2-carbonyl)benzoic acid (50.4 g, yield 82%).

$^1$H-NMR (500 MHz, THF-d8): 8.44 (t, 1H), 8.23 (d, 1H), 7.96 (m, 6H), 7.72 (m, 5H), 7.55 (t, 1H), 1.67 (s, 6H).

Synthesis Example 3

Preparation of 2-bromo-13,13-dimethyl-6H-indeno[1,2-b]anthracene-6,11(13H)-dione 2-(7-bromo-9,9-dimethyl-9H-fluorene-2-carbonyl)benzoic acid (20 g, 0.061 mol) was placed in a flask, and polyphosphoric acid (50 ml) was added thereto. The mixture was heated at 130° C. for 2 hours and cooled to less than 50□, and distilled water was gradually added thereto. The resultant solid was filtered, washed with a small amount of methanol, and dried to give 2-bromo-13,13-dimethyl-6H-indeno[1,2-b]anthracene-6,11(13H)-dione (16.6 g, yield=81%).

$^1$H-NMR (500 MHz, THF-d8): 8.29 (t, 2H), 8.09 (s, 2H), 7.85 (d, 2H), 7.72 (m, 3H), 1.67 (s, 6H).

Synthesis Example 4

Preparation of 2-bromo-13,13-dimethyl-6,11-diphenyl-11,13-dihydro-6H-indeno[1,2-b]anthracene-6,11-diol Bromobenzene (8.5 g, 0.054 mol) was placed in a flask, and THF (200 ml) was added thereto. After dissolution, n-BuLi (38.4 ml, 0.06 mol) was gradually added at −78☐, and the reaction mixture was stirred for one hour at a maintained temperature. Then, 2-bromo-13,13-dimethyl-6H-indeno[1,2-b]anthracene-6,11(13H)-dione (10 g, 0.024 mol) was added and the reaction mixture was stirred at room temperature for 17 hours. After the reaction was terminated, the reaction solution was washed with distilled water, extracted with ethyl acetate, and purified by column chromatography to give 2-bromo-13,13-dimethyl-6,11-diphenyl-11,13-dihydro-6H-indeno[1,2-b]anthracene-6,11-diol (11 g, yield=82%).

$^1$H-NMR (500 MHz, THF-d8): 7.96 (d, 1H), 7.78 (s, 1H), 7.45 (m, 2H), 7.37 (t, 2H), 7.31 (d, 2H), 7.19 (m, 9H), 7.10 (t, 2H), 1.69 (s, 6H).

Synthesis Example 5

Preparation of 2-bromo-13,13-dimethyl-6,11-diphenyl-13H-indeno[1,2-b]anthracene 2-bromo-13,13-dimethyl-6,11-diphenyl-11,13-dihydro-6H-indeno[1,2-b]anthracene-6,11-diol (4.19 g, 0.0075 mol), Potassium iodide (12.45 g, 0.075 mol), and Sodium hypophosphite (6 g, 0.037 mol) were placed in a flask, and were suspended in acetic acid (200 ml). The reaction mixture was stirred for five hours while heating. After the reaction was terminated, the reaction solution was added to an excess of distilled water. The resultant solid was washed with distilled water, filtered, and purified by column chromatography to give 2-bromo-13,13-dimethyl-6,11-diphenyl-13H-indeno[1,2-b]anthracene (2.9 g, yield=74%).

$^1$H-NMR (500 MHz, THF-d8): 8.11 (s, 1H), 7.96 (d, 1H), 7.91 (d, 2H), 7.72 (s, 2H), 7.65 (m, 5H), 7.48 (t, 2H), 7.34 (m, 4H), 7.26 (t, 2H), 1.67 (s, 6H).

Example 1

Preparation of Inv-1

2-bromo-13,13-dimethyl-6,11-diphenyl-13H-indeno[1,2-b]anthracene (2.9 g, 0056 mol), 1-phenyl-1H-benzo[d]imidazol-2-yl boronic acid (1.3 g, 0.0056 mol), and Pd(PPh$_3$)$_4$ (0.19 g, 0.0017 mol) were placed in a flask, and were dissolved in toluene (100 ml) under nitrogen. An aqueous solution (30 ml) including sodium carbonate (1.78 g, 0.0168 mol) dissolved therein was added thereto, and the reaction mixture was stirred under reflux for 5 hours. After the reaction was terminated, the reaction solution was extracted with dichloromethane, and purified by column chromatography (Hexane:MC=9:1 v/v) to give Inv-1 (2.5 g, yield=70%).

GC-Mass (theoretical value: 638.80 g/mol, measured value: 638 g/mol)

Example 2

Preparation of Inv-10

2-bromo-13,13-dimethyl-6,11-diphenyl-13H-indeno[1,2-b]anthracene (2.9 g, 0.0056 mol), and 4-(1-phenyl-1H-benzo[d]imidazol-2-yl)phenylboronic acid (1.8 g, 0.0056 mol) were placed in a flask and were dissolved in toluene (100 ml). Then, synthesis was carried out in the same manner as in Example 1 to give Inv-10 (3 g, yield=75%).

GC-Mass (theoretical value: 714.89 g/mol, measured value: 714 g/mol)

Example 3

Preparation of Inv-19

2-bromo-13,13-dimethyl-6,11-diphenyl-13H-indeno[1,2-b]anthracene (2.9 g, 0.0056 mol) and 3-(1-phenyl-1H-benzo[d]imidazol-2-yl)phenylboronic acid (1.8 g, 0.0056 mol) were placed in a flask and were dissolved in toluene (100 ml). Then, synthesis was carried out in the same manner as in Example 1 to give Inv-19 (2.8 g, yield=70%).

GC-Mass (theoretical value: 714.89 g/mol, measured value: 714 g/mol)

Example 4

Preparation of Inv-28

2-bromo-13,13-dimethyl-6,11-diphenyl-13H-indeno[1,2-b]anthracene (2.9 g, 0.0056 mol) and benzo[d]oxazol-2-ylboronic acid (0.91 g, 0.0056 mol) were placed in a flask and were dissolved in toluene (100 ml). Then, synthesis was carried out in the same manner as in Example 1 to give Inv-28 (2.5 g, yield=79%).

GC-Mass (theoretical value: 563.69 g/mol, measured value: 563 g/mol)

Example 5

Preparation of Inv-45

2-bromo-13,13-dimethyl-6,11-diphenyl-13H-indeno[1,2-b]anthracene (2.9 g, 0.0056 mol) and benzo[d]thiazol-2-ylboronic acid (1 g, 0.0056 mol) were placed in a flask and were dissolved in toluene (100 ml). Then, synthesis was carried out in the same manner as in Example 1 to give Inv-45 (2.6 g, yield=80%).

GC-Mass (theoretical value: 579.75 g/mol, measured value: 579 g/mol)

Example 6

Preparation of Inv-54

2-bromo-13,13-dimethyl-6,11-diphenyl-13H-indeno[1,2-b]anthracene (2.9 g, 0.0056 mol) and 4-(benzo[d]thiazol-2-yl)phenylboronic acid (1.42 g, 0.0056 mol) were placed in a flask and were dissolved in toluene (100 ml). Then, synthesis was carried out in the same manner as in Example 1 to give Inv-54 (2.4 g, yield=65%).

GC-Mass (theoretical value: 655.85 g/mol, measured value: 655 g/mol)

Example 7

Preparation of Inv-62

2-bromo-13,13-dimethyl-6,11-diphenyl-13H-indeno[1,2-b]anthracene (2.9 g, 0.0056 mol) and 5-(4,4,5,5-tetramethyl-1,3,2-dioxaborolan-2-yl)-2,2'-bipyridine (1.58 g, 0.0056 mol) were placed in a flask and were dissolved in toluene (100 ml). Then, synthesis was carried out in the same manner as in Example 1 to give Inv-62 (2.7 g, yield=80%).

GC-Mass (theoretical value: 600.75 g/mol, measured value: 600 g/mol)

Synthesis Example 6

Preparation of 2-bromo-13,13-dimethyl-6,11-di (naphthalen-2-yl)-11,13-dihydro-6H-indeno[1,2-b] anthracene-6,11-diol 2-Bromonaphthalene (11.18 g, 0.054 mol) was placed in a flask and THF (200 ml) was added thereto. After dissolution, n-BuLi (38.4 ml, 0.06 mol) was gradually added at −780, and the reaction mixture was stirred for one hour at a maintained temperature. Then, 2-bromo-13,13-dimethyl-6H-indeno[1, 2-b]anthracene-6,11(13H)-dione (10 g, 0.024 mol) was added and the reaction mixture was stirred at room temperature for 12 hours. After the reaction was terminated, the reaction solution was washed with distilled water, extracted with ethyl acetate, and purified by column chromatography to give 2-bromo-13,13-dimethyl-6,11-di(naphthalen-2-yl)-11, 13-dihydro-6H-indeno[1,2-b]anthracene-6,11-diol (11.38 g, yield=72%).

$^1$H-NMR (500 MHz, THF-d8): 7.95 (d, 1H), 7.78 (s, 1H), 7.70 (d, 2H), 7.64 (m, 8H), 7.61 (d, 2H), 7.45 (m, 4H), 7.24 (s, 1H), 7.18 (m, 4H), 1.68 (s, 6H).

Synthesis Example 7

Preparation of 2-bromo-13,13-dimethyl-6,11-di (naphthalen-2-yl)-13H-indeno[1,2-b]anthracene 2-bromo-13,13-dimethyl-6,11-di(naphthalen-2-yl)-11, 13-dihydro-6H-indeno[1,2-b]anthracene-6,11-diol (5 g, 0.0075 mol), KI (12.45 g, 0.075 mol), and Sodium hypophosphite (6 g, 0.037 mol) were placed in a flask, and acetic acid (200 ml) was added thereto. The reaction mixture was stirred for five hours while heating. After the reaction was terminated, the reaction solution was added to an excess of distilled water. The resultant solid was washed with distilled water, filtered, and purified by column chromatography to give 2-bromo-13,13-dimethyl-6,11-di(naphthalen-2-yl)-13H-indeno[1,2-b]anthracene (3.56 g, yield=76%).

$^1$H-NMR (500 MHz, THF-d8): 8.02 (d, 1H), 7.82 (s, 1H), 7.73 (d, 2H), 7.65 (m, 8H), 7.61 (d, 2H), 7.55 (m, 4H), 7.34 (s, 1H), 7.21 (m, 4H), 1.71 (s, 6H)

Example 8

Preparation of Inv-2

2-bromo-13,13-dimethyl-6,11-di(naphthalen-2-yl)-13H-indeno[1,2-b]anthracene (5 g, 0.008 mol) and 1-phenyl-1H-benzo[d]imidazol-2-yl boronic acid (1.9 g, 0.008 mol) were dissolved in toluene (150 ml). Then, synthesis was carried out in the same manner as in Example 1 to give Inv-2 (4.5 g, yield=76%).

GC-Mass (theoretical value: 738.91 g/mol, measured value: 738 g/mol)

Example 9

Preparation of Inv-11

2-bromo-13,13-dimethyl-6,1'-di(naphthalen-2-yl)-13H-indeno[1,2-b]anthracene (5 g, 0.008 mol) and 4-(1-phenyl-1H-benzo[d]imidazol-2-yl)phenylboronic acid (2.51 g, 0.008 mol) were dissolved in toluene (150 ml). Then, synthesis was carried out in the same manner as in Example 1 to give Inv-11 (5.2 g, yield=81%).

GC-Mass (theoretical value: 815.01 g/mol, measured value: 815 g/mol)

Example 10

Preparation of Inv-20

2-bromo-13,13-dimethyl-6,11-di(naphthalen-2-yl)-13H-indeno[1,2-b]anthracene (5 g, 0.008 mol) and 3-(1-phenyl-1H-benzo[d]imidazol-2-yl)phenylboronic acid (2.51 g, 0.008 mol) were dissolved in toluene (150 ml). Then, synthesis was carried out in the same manner as in Example 1 to give Inv-20 (5.0 g, yield=78%).

GC-Mass (theoretical value: 815.01 g/mol, measured value: 815 g/mol)

Example 11

Preparation of Inv-29

2-bromo-13,13-dimethyl-6,11-di(naphthalen-2-yl)-13H-indeno[1,2-b]anthracene (5 g, 0.008 mol) and benzo[d]oxazol-2-ylboronic acid (1.3 g, 0.008 mol) were dissolved in toluene (150 ml). Then, synthesis was carried out in the same manner as in Example 1 to give Inv-29 (3.6 g, yield=71%).

GC-Mass (theoretical value: 663.80 g/mol, measured value: 663 g/mol)

Example 12

Preparation of Inv-38

2-bromo-13,13-dimethyl-6,11-di(naphthalen-2-yl)-13H-indeno[1,2-b]anthracene (5 g, 0.008 mol) and 4-(benzo[d] oxazol-2-yl)phenylboronic acid (1.9 g, 0.008 mol) were dissolved in toluene (150 ml). Then, synthesis was carried out in the same manner as in Example 1 to give Inv-38 (4.3 g, yield=73%).

GC-Mass (theoretical value: 739.90 g/mol, measured value: 739 g/mol)

Example 13

Preparation of Inv-46

2-bromo-13,13-dimethyl-6,11-di(naphthalen-2-yl)-13H-indeno[1,2-b]anthracene (5 g, 0.008 mol) and benzo[d]thiazol-2-ylboronic acid (1.43 g, 0.008 mol) were dissolved in toluene (150 ml). Then, synthesis was carried out in the same manner as in Example 1 to give Inv-46 (3.8 g, yield=70%).

GC-Mass (theoretical value: 679.87 g/mol, measured value: 679 g/mol)

Example 14

Preparation of Inv-55

2-bromo-13,13-dimethyl-6,11-di(naphthalen-2-yl)-13H-indeno[1,2-b]anthracene (5 g, 0.008 mol) and 4-(benzo[d] thiazol-2-yl)phenylboronic acid (2.04 g, 0.008 mol) were dissolved in toluene (150 ml). Then, synthesis was carried out in the same manner as in Example 1 to give Inv-55 (4.2 g, yield=70%).

GC-Mass (theoretical value: 755.96 g/mol, measured value: 755 g/mol)

Example 15

Preparation of Inv-63

2-bromo-13,13-dimethyl-6,11-di(naphthalen-2-yl)-13H-indeno[1,2-b]anthracene (5 g, 0.008 mol) and 5-(4,4,5,5-tetramethyl-1,3,2-dioxaborolan-2-yl)-2,2'-bipyridine (2.26 g, 0.008 mol) were dissolved in toluene (150 ml). Then, synthesis was carried out in the same manner as in Example 1 to give Inv-63 (3 g, yield=53%).

GC-Mass (theoretical value: 700.87 g/mol, measured value: 700 g/mol)

Synthesis Example 8

Preparation of 2-bromo-13,13-dimethyl-6,11-di(naphthalen-1-yl)-11,13-dihydro-6H-indeno[1,2-b]anthracene-6,11-diol 2-bromo-13,13-dimethyl-6,11-di(naphthalen-1-yl)-11,13-dihydro-6H-indeno[1,2-b]anthracene-6,11-diol (9.8 g, yield=62%) was obtained in the same manner as in Synthesis Example 6 except that instead of 2-bromonaphthalene, 1-Bromonaphthalene (11.18 g, 0.054 mol) was added.

GC-Mass (theoretical value: 659.61 g/mol, measured value: 659 g/mol)

Synthesis Example 9

Preparation of 2-bromo-13,13-dimethyl-6,11-di(naphthalen-1-yl)-13H-indeno[1,2-b]anthracene 2-bromo-13,13-dimethyl-6,11-di(naphthalen-1-yl)-13H-indeno[1,2-b]anthracene (3 g, yield=63%) was obtained in the same manner as in Synthesis Example 7 except that 2-bromo-13,13-dimethyl-6,11-di(naphthalen-1-yl)-11,13-dihydro-6H-indeno[1,2-b]anthracene-6,11-diol (5 g, 0.0075 mol) was added.

GC-Mass (theoretical value: 625.59 g/mol, measured value: 625 g/mol)

Example 16

Preparation of Inv-3

2-bromo-13,13-dimethyl-6,11-di(naphthalen-1-yl)-13H-indeno[1,2-b]anthracene (5 g, 0.008 mol) and 1-phenyl-1H-benzo[d]imidazol-2-yl boronic acid (1.9 g, 0.008 mol) were dissolved in toluene (150 ml). Then, synthesis was carried out in the same manner as in Example 1 to give Inv-3 (4.0 g, yield=67%).

Example 17

Preparation of Inv-12

2-bromo-13,13-dimethyl-6,11-di(naphthalen-1-yl)-13H-indeno[1,2-b]anthracene (5 g, 0.008 mol) and 4-(1-phenyl-1H-benzo[d]imidazol-2-yl)phenylboronic acid (2.51 g, 0.008 mol) were dissolved in toluene (150 ml). Then, synthesis was carried out in the same manner as in Example 1 to give Inv-12 (5.1 g, yield=78%).

GC-Mass (theoretical value: 738.91 g/mol, measured value: 738 g/mol)

Example 18

Preparation of Inv-21

2-bromo-13,13-dimethyl-6,11-di(naphthalen-1-yl)-13H-indeno[1,2-b]anthracene (5 g, 0.008 mol) and 3-(1-phenyl-1H-benzo[d]imidazol-2-yl)phenylboronic acid (2.51 g, 0.008 mol) were dissolved in toluene (150 ml). Then, synthesis was carried out in the same manner as in Example 1 to give Inv-21 (3.5 g, yield=54%).

GC-Mass (theoretical value: 815.01 g/mol, measured value: 815 g/mol)

Example 19

Preparation of Inv-30

2-bromo-13,13-dimethyl-6,11-di(naphthalen-1-yl)-13H-indeno[1,2-b]anthracene (5 g, 0.008 mol) and benzo[d]oxazol-2-ylboronic acid (1.3 g, 0.008 mol) were dissolved in toluene (150 ml). Then, synthesis was carried out in the same manner as in Example 1 to give Inv-30 (3.2 g, yield=60%).

GC-Mass (theoretical value: 663.80 g/mol, measured value: 663 g/mol)

Example 20

Preparation of Inv-39

2-bromo-13,13-dimethyl-6,11-di(naphthalen-1-yl)-13H-indeno[1,2-b]anthracene (5 g, 0.008 mol) and 4-(benzo[d]oxazol-2-yl)phenylboronic acid (1.9 g, 0.008 mol) were dissolved in toluene (150 ml). Then, synthesis was carried out in the same manner as in Example 1 to give Inv-39 (3.5 g, yield=59%).

GC-Mass (theoretical value: 739.90 g/mol, measured value: 739 g/mol)

Example 21

Preparation of Inv-47

2-bromo-13,13-dimethyl-6,11-di(naphthalen-1-yl)-13H-indeno[1,2-b]anthracene (5 g, 0.008 mol) and benzo[d]thiazol-2-ylboronic acid (1.43 g, 0.008 mol) were dissolved in toluene (150 ml). Then, synthesis was carried out in the same manner as in Example 1 to give Inv-47 (3.1 g, yield=57%).

GC-Mass (theoretical value: 679.87 g/mol, measured value: 679 g/mol)

Example 22

Preparation of Inv-64

2-bromo-13,13-dimethyl-6,11-di(naphthalen-1-yl)-13H-indeno[1,2-b]anthracene (5 g, 0.008 mol) and 5-(4,4,5,5-tetramethyl-1,3,2-dioxaborolan-2-yl)-2,2'-bipyridine (2.26 g, 0.008 mol) were dissolved in toluene (150 ml). Then, synthesis was carried out in the same manner as in Example 1 to give Inv-64 (3.2 g, yield=57%).

GC-Mass (theoretical value: 700.87 g/mol, measured value: 700 g/mol)

Synthesis Example 10

Preparation of 6,11-di(biphenyl-4-yl)-2-bromo-13,13-dimethyl-11,13-dihydro-6H-indeno[1,2-b]anthracene-6,11-diol 4-bromobiphenyl (12.58 g, 0.054 mol) was placed in a flask, and THF (200 ml) was added thereto. After dissolution, n-BuLi (38.4 ml, 0.06 mol) was gradually added at −78□, and the reaction mixture was stirred for one hour at a maintained temperature. Then, 2-bromo-13,13-dimethyl-6H-indeno[1,2-b]anthracene-6,11(13H)-dione (10 g, 0.024 mol) was added, and the reaction mixture was stirred at room temperature for 12 hours. After the reaction was terminated, the reaction solution was washed with distilled water, extracted with ethyl acetate, and purified by column chromatography to give 6,11-di(biphenyl-4-yl)-2-bromo-13,13-dimethyl-11,13-dihydro-6H-indeno[1,2-b]anthracene-6,11-diol (10.8 g, yield=63%).

GC-Mass(FAB): (theoretical value: 711.68 g/mol, measured value: 711 g/mol)

Synthesis Example 11

Preparation of 6,11-di(biphenyl-4-yl)-2-bromo-13,13-dimethyl-13H-indeno[1,2-b]anthracene 6,11-di(biphenyl-4-yl)-2-bromo-13,13-dimethyl-13H-indeno[1,2-b]anthracene (2.9 g, yield=57%) was obtained in the same manner as in Synthesis Example 7 except that 6,11-di(biphenyl-4-yl)-2-bromo-13,13-dimethyl-11,13-dihydro-6H-indeno[1,2-b]anthracene-6,11-diol (5.33 g, 0.0075 mol) was added.

GC-Mass(FAB): (theoretical value: 677.67 g/mol, measured value: 677 g/mol)

Example 23

Preparation of Inv-4

6,11-di(biphenyl-4-yl)-2-bromo-13,13-dimethyl-13H-indeno[1,2-b]anthracene (5 g, 0.0074 mol) and 1-phenyl-1H-benzo[d]imidazol-2-yl boronic acid (1.76 g, 0.0074 mol) were dissolved in toluene (150 ml). Then, synthesis was carried out in the same manner as in Example 1 to give Inv-4 (3.8 g, yield=66%).

GC-Mass(FAB): (theoretical value: 790.99 g/mol, measured value: 790 g/mol)

Example 24

Preparation of Inv-13

6,11-di(biphenyl-4-yl)-2-bromo-13,13-dimethyl-13H-indeno[1,2-b]anthracene (5 g, 0.0074 mol) and 4-(1-phenyl-1H-benzo[d]imidazol-2-yl)phenylboronic acid (2.32 g, 0.0074 mol) were dissolved in toluene (150 ml). Then, synthesis was carried out in the same manner as in Example 1 to give Inv-13 (5.5 g, yield=85%).

GC-Mass(FAB): (theoretical value: 867.08 g/mol, measured value: 867 g/mol)

Example 25

Preparation of Inv-22

6,11-di(biphenyl-4-yl)-2-bromo-13,13-dimethyl-13H-indeno[1,2-b]anthracene (5 g, 0.0074 mol) and 3-(1-phenyl-1H-benzo[d]imidazol-2-yl)phenylboronic acid (2.32 g, 0.0074 mol) were dissolved in toluene (150 ml). Then, synthesis was carried out in the same manner as in Example 1 to give Inv-22 (4.3 g, yield=67%).

GC-Mass(FAB): (theoretical value: 867.08 g/mol, measured value: 867 g/mol)

Example 26

Preparation of Inv-31

6,11-di(biphenyl-4-yl)-2-bromo-13,13-dimethyl-13H-indeno[1,2-b]anthracene (5 g, 0.0074 mol) and benzo[d]oxazol-2-ylboronic acid (1.2 g, 0.0074 mol) were dissolved in toluene (150 ml). Then, synthesis was carried out in the same manner as in Example 1 to give Inv-31 (3.0 g, yield=56%).

GC-Mass(FAB): (theoretical value: 715.88 g/mol, measured value: 715 g/mol)

Example 27

Preparation of Inv-40

6,11-di(biphenyl-4-yl)-2-bromo-13,13-dimethyl-13H-indeno[1,2-b]anthracene (5 g, 0.0074 mol) and 4-(benzo[d]oxazol-2-yl)phenylboronic acid (1.76 g, 0.0074 mol) were dissolved in toluene (150 ml). Then, synthesis was carried out in the same manner as in Example 1 to give Inv-40 (3.2 g, yield=55%).

GC-Mass(FAB): (theoretical value: 791.97 g/mol, measured value: 791 g/mol)

Example 28

Preparation of Inv-48

6,11-di(biphenyl-4-yl)-2-bromo-13,13-dimethyl-13H-indeno[1,2-b]anthracene (5 g, 0.0074 mol) and benzo[d]thiazol-2-ylboronic acid (1.32 g, 0.0074 mol) were dissolved in toluene (150 ml). Then, synthesis was carried out in the same manner as in Example 1 to give Inv-48 (3.3 g, yield=61%).

GC-Mass(FAB): (theoretical value: 731.94 g/mol, measured value: 731 g/mol)

Example 29

Preparation of Inv-56

6,11-di(biphenyl-4-yl)-2-bromo-13,13-dimethyl-13H-indeno[1,2-b]anthracene (5 g, 0.0074 mol) and 4-(benzo[d]thiazol-2-yl)phenylboronic acid (1.88 g, 0.0074 mol) were dissolved in toluene (150 ml). Then, synthesis was carried out in the same manner as in Example 1 to give Inv-56 (3.8 g, yield=64%).

GC-Mass(FAB): (theoretical value: 808.04 g/mol, measured value: 807 g/mol)

Example 30

Preparation of Inv-65

6,11-di(biphenyl-4-yl)-2-bromo-13,13-dimethyl-13H-indeno[1,2-b]anthracene (5 g, 0.0074 mol) and 5-(4,4,5,5-tetramethyl-1,3,2-dioxaborolan-2-yl)-2,2'-bipyridine (2.08 g, 0.0074 mol) were dissolved in toluene (150 ml). Then, synthesis was carried out in the same manner as in Example 1 to give Inv-65 (3.2 g, yield=57%).

GC-Mass(FAB): (theoretical value: 752.94 g/mol, measured value: 752 g/mol)

Synthesis Example 12

Preparation of 2-bromo-6,11-bis(9,9-dimethyl-9H-fluoren-2-yl)-13,13-dimethyl-11,13-dihydro-6H-indeno[1,2-b]anthracene-6,11-diol 2-bromo-9,9-dimethyl-9H-fluorene (14.75 g, 0.054 mol) was placed in a flask, and THF (200 ml) was added thereto. After dissolution, n-BuLi (38.4 ml, 0.06 mol) was gradually added at −780, and the reaction mixture was stirred for one hour at a maintained temperature. Then, 2-bromo-13,13-dimethyl-6H-indeno[1,2-b]anthracene-6,11(13H)-dione (10 g, 0.024 mol) was added and the reaction mixture was stirred at room temperature for 12 hours. After the reaction was terminated, the reaction solution was washed with distilled water, extracted with ethyl acetate, and purified by column chromatography to give 2-bromo-6,11-bis(9,9-dimethyl-9H-fluoren-2-yl)-13,13-dimethyl-11,13-dihydro-6H-indeno[1,2-b]anthracene-6,11-diol (12.2 g, yield=64%).

GC-Mass(FAB): (theoretical value: 791.81 g/mol, measured value: 791 g/mol)

Synthesis Example 13

Preparation of 2-bromo-6,11-bis(9,9-dimethyl-9H-fluoren-2-yl)-13,13-dimethyl-13H-indeno[1,2-b]anthracene 6,11-di(biphenyl-4-yl)-2-bromo-13,13-dimethyl-13H-indeno[1,2-b]anthracene (3.1 g, yield=54%) was obtained in the same manner as in Synthesis Example 7 except that 2-bromo-6-(9,9-dimethyl-9H-fluoren-2-yl)-11-(9,9-dimethyl-9H-fluoren-3-yl)-13,13-dimethyl-11,13-dihydro-6H-indeno[1,2-b]anthracene-6,11-diol (5.95 g, 0.0075 mol) was added.

GC-Mass(FAB): (theoretical value: 757.80 g/mol, measured value: 757 g/mol)

Example 31

Preparation of Inv-7

2-bromo-6,11-bis(9,9-dimethyl-9H-fluoren-2-yl)-13,13-dimethyl-13H-indeno[1,2-b]anthracene (5 g, 0.0066 mol) and 1-phenyl-1H-benzo[d]imidazol-2-yl boronic acid (1.57 g, 0.0066 mol) were dissolved in toluene (150 ml). Then, synthesis was carried out in the same manner as in Example 1 to give Inv-7 (3.5 g, yield=61%).

GC-Mass(FAB): (theoretical value: 871.12 g/mol, measured value: 871 g/mol)

Example 32

Preparation of Inv-16

2-bromo-6,11-bis(9,9-dimethyl-9H-fluoren-2-yl)-13,13-dimethyl-13H-indeno[1,2-b]anthracene (5 g, 0.0066 mol) and 4-(1-phenyl-1H-benzo[d]imidazol-2-yl)phenylboronic acid (2.07 g, 0.0066 mol) were dissolved in toluene (150 ml). Then, synthesis was carried out in the same manner as in Example 1 to give Inv-16 (4.8 g, yield=77%).

GC-Mass(FAB): (theoretical value: 947.21 g/mol, measured value: 947 g/mol)

Example 33

Preparation of Inv-25

2-bromo-6,11-bis(9,9-dimethyl-9H-fluoren-2-yl)-13,13-dimethyl-13H-indeno[1,2-b]anthracene (5 g, 0.0066 mol) and 3-(1-phenyl-1H-benzo[d]imidazol-2-yl)phenylboronic acid (2.07 g, 0.0066 mol) were dissolved in toluene (150 ml). Then, synthesis was carried out in the same manner as in Example 1 to give Inv-25 (4.5 g yield=72%).

GC-Mass(FAB): (theoretical value: 947.21 g/mol, measured value: 947 g/mol)

Example 34

Preparation of Inv-34

2-bromo-6,11-bis(9,9-dimethyl-9H-fluoren-2-yl)-13,13-dimethyl-13H-indeno[1,2-b]anthracene (5 g, 0.0066 mol) and benzo[d]oxazol-2-ylboronic acid (1.07 g, 0.0066 mol) were dissolved in toluene (150 ml). Then, synthesis was carried out in the same manner as in Example 1 to give Inv-34 (2.9 g, yield=55%).

GC-Mass(FAB): (theoretical value: 796.01 g/mol, measured value: 795 g/mol)

Example 35

Preparation of Inv-43

2-bromo-6,11-bis(9,9-dimethyl-9H-fluoren-2-yl)-13,13-dimethyl-13H-indeno[1,2-b]anthracene (5 g, 0.0066 mol) and 4-(benzo[d]oxazol-2-yl)phenylboronic acid (1.57 g, 0.0066 mol) were dissolved in toluene (150 ml). Then, synthesis was carried out in the same manner as in Example 1 to give Inv-43 (3.3 g, yield=57%).

GC-Mass(FAB): (theoretical value: 872.10 g/mol, measured value: 872 g/mol)

Example 36

Preparation of Inv-51

2-bromo-6,11-bis(9,9-dimethyl-9H-fluoren-2-yl)-13,13-dimethyl-13H-indeno[1,2-b]anthracene (5 g, 0.0066 mol) and benzo[d]thiazol-2-ylboronic acid (1.18 g, 0.0066 mol) were dissolved in toluene (150 ml). Then, synthesis was carried out in the same manner as in Example 1 to give Inv-51 (2.8 g, yield=53%).

GC-Mass(FAB): (theoretical value: 812.07 g/mol, measured value: 811 g/mol)

Example 37

Preparation of Inv-59

2-bromo-6,11-bis(9,9-dimethyl-9H-fluoren-2-yl)-13,13-dimethyl-13H-indeno[1,2-b]anthracene (5 g, 0.0066 mol) and 4-(benzo[d]thiazol-2-yl)phenylboronic acid (1.68 g, 0.0066 mol) were dissolved in toluene (150 ml). Then, synthesis was carried out in the same manner as in Example 1 to give Inv-59 (3.5 g, yield=60%).

GC-Mass(FAB): (theoretical value: 888.17 g/mol, measured value: 887 g/mol)

Example 38

Preparation of Inv-68

2-bromo-6,11-bis(9,9-dimethyl-9H-fluoren-2-yl)-13,13-dimethyl-13H-indeno[1,2-b]anthracene (5 g, 0.0066 mol) and 5-(4,4,5,5-tetramethyl-1,3,2-dioxaborolan-2-yl)-2,2-y-bipyridine (1.86 g, 0.0066 mol) were dissolved in toluene (150 ml). Then, synthesis was carried out in the same manner as in Example 1 to give Inv-68 (3.0 g, yield=55%).

GC-Mass(FAB): (theoretical value: 833.07 g/mol, measured value: 832 g/mol)

Synthesis Example 14

Preparation of 2-bromo-13,13-dimethyl-6,11-di(phenanthren-9-yl)-11,13-dihydro-6H-indeno[1,2-b]anthracene-6,11-diol 9-bromophenanthrene (13.88 g, 0.054 mol) was placed in a flask, and THF (200 ml) was added thereto. After dissolution, n-BuLi (38.4 ml, 0.06 mol) was gradually added at −780, and the reaction mixture was stirred for one hour at a maintained temperature. Then, 2-bromo-13,13-dimethyl-6H-indeno[1,2-b]anthracene-6,11(13H)-dione (10 g, 0.024 mol) was added and the reaction mixture was stirred at room temperature for 12 hours. After the reaction was terminated, the reaction solution was washed with distilled water, extracted with ethyl acetate, and purified by column chromatography to give, 2-bromo-13,13-dimethyl-6,11-di(phenanthren-9-yl)-11,13-dihydro-6H-indeno[1,2-b]anthracene-6,11-diol (13.1 g, yield=72%).

GC-Mass(FAB): (theoretical value: 759.73 g/mol, measured value:759 g/mol)

Synthesis Example 15

Preparation of 2-bromo-13,13-dimethyl-6,11-di(phenanthren-9-yl)-13H-indeno[1,2-b]anthracene 2-bromo-13,13-dimethyl-6,11-di(phenanthren-9-yl)-13H-indeno[1,2-b]anthracene (3.5 g, yield=64%) was obtained in the same manner as in Synthesis Example 7 except that 2-bromo-13,13-dimethyl-6,11-di(phenanthren-9-Y1)-11,13-dihydro-6H-indeno[1,2-b]anthracene-6,11-diol (5.69 g, 0.0075 mol) was added.

GC-Mass(FAB): (theoretical value: 725.71 g/mol, measured value: 725 g/mol)

Example 39

Preparation of Inv-8

2-bromo-13,13-dimethyl-6,11-di(phenanthren-9-yl)-13H-indeno[1,2-b]anthracene (5 g, 0.0068 mol) and 1-phenyl-1H-benzo[d]imidazol-2-yl boronic acid (1.61 g, 0.0068 mol) were dissolved in toluene (150 ml). Then, synthesis was carried out in the same manner as in Example 1 to give Inv-8 (3.6 g, yield=63%).

GC-Mass(FAB): (theoretical value: 839.03 g/mol, measured value: 838 g/mol)

Example 40

Preparation of Inv-17

2-bromo-13,13-dimethyl-6,11-di(phenanthren-9-yl)-13H-indeno[1,2-b]anthracene (5 g, 0.0068 mol) and 4-(1-phenyl-1H-benzo[d]imidazol-2-yl)phenylboronic acid (2.14 g, 0.0068 mol) were dissolved in toluene (150 ml). Then, synthesis was carried out in the same manner as in Example 1 to give Inv-17 (4.1 g, yield=66%).

GC-Mass(FAB): (theoretical value: 915.13 g/mol, measured value: 915 g/mol)

Example 41

Preparation of Inv-27

2-bromo-13,13-dimethyl-6,11-di(phenanthren-9-yl)-13H-indeno[1,2-b]anthracene (5 g, 0.0068 mol) and 3-(1-phenyl-1H-benzo[d]imidazol-2-yl)phenylboronic acid (2.14 g, 0.0068 mol) were dissolved in toluene (150 ml). Then, synthesis was carried out in the same manner as in Example 1 to give Inv-27 (4.3 g, yield=69%).

GC-Mass(FAB): (theoretical value: 915.13 g/mol, measured value: 915 g/mol)

Example 42

Preparation of Inv-35

2-bromo-13,13-dimethyl-6,11-di(phenanthren-9-yl)-13H-indeno[1,2-b]anthracene (5 g, 0.0068 mol) and benzo[d]oxazol-2-ylboronic acid (1.11 g, 0.0068 mol) were dissolved in toluene (150 ml). Then, synthesis was carried out in the same manner as in Example 1 to give Inv-35 (3.1 g, yield=59%).

GC-Mass(FAB): (theoretical value: 763.92 g/mol, measured value: 763 g/mol)

Example 43

Preparation of Inv-52

2-bromo-13,13-dimethyl-6,11-di(phenanthren-9-yl)-13H-indeno[1,2-b]anthracene (5 g, 0.0068 mol) and benzo[d]thiazol-2-ylboronic acid (1.22 g, 0.0068 mol) were dissolved in toluene (150 ml). Then, synthesis was carried out in the same manner as in Example 1 to give Inv-52 (3.0 g, yield=56%).

GC-Mass(FAB): (theoretical value: 779.99 g/mol, measured value: 779 g/mol)

Example 44

Preparation of Inv-60

2-bromo-13,13-dimethyl-6,11-di(phenanthren-9-yl)-13H-indeno[1,2-b]anthracene (5 g, 0.0068 mol) and 4-(benzo[d]thiazol-2-yl)phenylboronic acid (1.73 g, 0.0066 mol) were dissolved in toluene (150 ml). Then, synthesis was carried out in the same manner as in Example 1 to give Inv-60 (3.2 g, yield=55%).

GC-Mass(FAB): (theoretical value: 856.08 g/mol, measured value: 856 g/mol)

Example 45

Preparation of Inv-69

2-bromo-13,13-dimethyl-6,11-di(phenanthren-9-yl)-13H-indeno[1,2-b]anthracene (5 g, 0.0068 mol) and 5-(4,4,5,5-tetramethyl-1,3,2-dioxaborolan-2-yl)-2,2'-bipyridine (1.86 g, 0.0066 mol) were dissolved in toluene (150 ml).

Then, synthesis was carried out in the same manner as in Example 1 to give Inv-69 (3.2 g, yield=59%).

GC-Mass(FAB): (theoretical value: 800.98 g/mol, measured value: 800 g/mol)

Synthesis Example 16

Preparation of 4-bromo-2-(9,9-dimethyl-9H-fluorene-2-carbonyl)benzoic acid

Fluorene (27.78 g, 0.143 mol) and 4-Bromo Phthalic anhydride (48.69 g, 0.214 mol) were placed in a reaction vessel and was dissolved in dichloromethane (700 ml). Then, aluminum chloride (28.7 g, 0.214 mol) was gradually added at 0t, and the reaction mixture was stirred at room temperature for 12 hours. After the reaction was terminated, distilled water was gradually added, and the reaction solution was extracted with dichloromethane and washed three times with distilled water. After solvent removal, the resultant solid was placed in a hexane(2 l)-containing vessel, washed, filtered and dried to give 4-bromo-2-(9,9-dimethyl-9H-fluorene-2-carbonyl)benzoic acid (30 g, yield=50%).

$^1$H NMR (500 MHz, THF-d8): 8.12 (d, 1H), 8.08 (s, 1H), 7.99 (s, 1H), 7.92 (m, 3H), 7.84 (d, 1H), 7.55 (d, 1H), 7.30 (t, 2H), 1.63 (s, 6H)

Synthesis Example 17

Preparation of 9-bromo-13,13-dimethyl-6H-indeno[1,2-b]anthracene-6,11(13H)-dione 4-bromo-2-(9,9-dimethyl-9H-fluorene-2-carbonyl)benzoic acid (18.53 g, 0.044 mol) was placed in a flask, and polyphosphoric acid (50 ml) was added thereto. The mixture was heated at 140° C. for 2 hours and cooled to less than 50□, and distilled water was gradually added thereto. The resultant solid was filtered, washed with a small amount of methanol, and dried to give 9-bromo-13,13-dimethyl-6H-indeno[1,2-b]anthracene-6,11(13H)-dione (11 g, yield=62%).

$^1$H NMR (500 MHz, THF-d8): 8.2 (s, 1H), 8.09 (s, 1H), 7.97 (s, 1H), 7.84 (d, 1H), 7.70 (m, 2H), 7.55 (d, 1H), 7.28 (t, 1H), 7.08 (t, 1H), 1.68 (s, 6H)

Synthesis Example 18

Preparation of 9-bromo-13,13-dimethyl-6,11-diphenyl-11,13-dihydro-6H-indeno[1,2-b]anthracene-6,11-diol Bromobenzene (8.5 g, 0.054 mol) was placed in a flask, and THF (200 ml) was added thereto. After dissolution, n-BuLi (38.4 ml, 0.06 mol) was gradually added at −780, and the reaction mixture was stirred for one hour at a maintained temperature. Then, 9-bromo-13,13-dimethyl-6H-indeno[1,2-b]anthracene-6,11(13H)-dione (10 g, 0.024 mol) was added and the reaction mixture was stirred at room temperature for 12 hours. After the reaction was terminated, the reaction solution was washed with distilled water, extracted with ethyl acetate, and purified by column chromatography to give 9-bromo-13,13-dimethyl-6,11-diphenyl-11,13-dihydro-6H-indeno[1,2-b]anthracene-6,11-diol (8.5 g, yield=63%).

$^1$H-NMR (500 MHz, THF-d8): 7.93 (d, 1H), 7.81 (s, 1H), 7.48 (m, 2H), 7.34 (t, 2H), 7.31 (d, 2H), 7.21 (m, 9H), 7.15 (t, 2H), 1.67 (s, 6H).

Synthesis Example 19

Preparation of 9-bromo-13,13-dimethyl-6,11-diphenyl-13H-indeno[1,2-b]anthracene 9-bromo-13,13-dimethyl-6,11-diphenyl-11,13-dihydro-6H-indeno[1,2-b]anthracene-6,11-diol (4.19 g, 0.0075 mol), potassium iodide (12.45 g, 0.075 mol), and sodium hypophosphite (6 g, 0.037 mol) were placed in a flask, and were suspended in acetic acid (200 ml). The reaction mixture was stirred for five hours while heating. After the reaction was terminated, the reaction solution was added to an excess of distilled water. The resultant solid was washed with distilled water, filtered, and purified by column chromatography to give 9-bromo-13,13-dimethyl-6,11-diphenyl-13H-indeno[1,2-b]anthracene (2.9 g, yield=74%).

GC-Mass(FAB): (theoretical value: 525.48 g/mol, measured value: 525 g/mol)

Example 46

Preparation of Inv-71

9-bromo-13,13-dimethyl-6,11-diphenyl-13H-indeno[1,2-b]anthracene (5 g, 0.0095 mol) and 1-phenyl-1H-benzo[d]imidazol-2-yl boronic acid (2.26 g, 0.0095 mol) were dissolved in toluene (150 ml). Then, synthesis was carried out in the same manner as in Example 1 to give Inv-71 (4.2 g, yield=69%).

GC-Mass(FAB): (theoretical value: 638.80 g/mol, measured value: 638 g/mol)

Example 47

Preparation of Inv-80

9-bromo-13,13-dimethyl-6,11-diphenyl-13H-indeno[1,2-b]anthracene (5 g, 0.0095 mol) and 4-(1-phenyl-1H-benzo[d]imidazol-2-yl)phenylboronic acid (2.98 g, 0.0095 mol) were dissolved in toluene (150 ml). Then, synthesis was carried out in the same manner as in Example 1 to give Inv-80 (4.8 g, yield=72%).

GC-Mass(FAB): (theoretical value: 714.89 g/mol, measured value: 714 g/mol)

Example 48

Preparation of Inv-89

9-bromo-13,13-dimethyl-6,11-diphenyl-13H-indeno[1,2-b]anthracene (5 g, 0.0095 mol) and 3-(1-phenyl-1H-benzo[d]imidazol-2-yl)phenylboronic acid (2.14 g, 0.0095 mol) were dissolved in toluene (150 ml). Then, synthesis was carried out in the same manner as in Example 1 to give Inv-89 (4.6 g, yield=68%).

GC-Mass(FAB): (theoretical value: 714.89 g/mol, measured value: 714 g/mol)

Example 49

Preparation of Inv-98

9-bromo-13,13-dimethyl-6,11-diphenyl-13H-indeno[1,2-b]anthracene (5 g, 0.0095 mol) and benzo[d]oxazol-2-ylboronic acid (1.11 g, 0.0095 mol) were dissolved in toluene (150 ml). Then, synthesis was carried out in the same manner as in Example 1 to give Inv-98 (3.1 g, yield=58%).

GC-Mass(FAB): (theoretical value: 563.69 g/mol, measured value: 563 g/mol)

Example 50

Preparation of Inv-107

9-bromo-13,13-dimethyl-6,11-diphenyl-13H-indeno[1,2-b]anthracene (5 g, 0.0095 mol) and 4-(benzo[d]oxazol-2-yl)phenylboronic acid (2.27 g, 0.0095 mol) were dissolved in toluene (150 ml). Then, synthesis was carried out in the same manner as in Example 1 to give Inv-107 (4.7 g, yield=77%).

GC-Mass(FAB): (theoretical value: 639.78 g/mol, measured value: 639 g/mol)

Example 51

Preparation of Inv-117

9-bromo-13,13-dimethyl-6,11-diphenyl-13H-indeno[1,2-b]anthracene (5 g, 0.0095 mol) and benzo[d]thiazol-2-ylboronic acid (1.7 g, 0.0095 mol) were dissolved in toluene (150 ml). Then, synthesis was carried out in the same manner as in Example 1 to give Inv-117 (2.5 g, yield=45%).

GC-Mass(FAB): (theoretical value: 579.75 g/mol, measured value: 579 g/mol)

Example 52

Preparation of Inv-126

9-bromo-13,13-dimethyl-6,11-diphenyl-13H-indeno[1,2-b]anthracene (5 g, 0.0095 mol) and 4-(benzo[d]thiazol-2-yl)phenylboronic acid (2.42 g, 0.0095 mol) were dissolved in toluene (150 ml). Then, synthesis was carried out in the same manner as in Example 1 to give Inv-126 (5.0 g, yield=80%).

GC-Mass(FAB): (theoretical value: 655.85 g/mol, measured value: 655 g/mol)

Synthesis Example 20

Preparation of 9-bromo-13,13-dimethyl-6,11-di(naphthalen-2-yl)-11,13-dihydro-6H-indeno[1,2-b]anthracene-6,11-diol 2-Bromonaphthalene (16.77 g, 0.081 mol) was placed in a flask, and THF (300 ml) was added thereto. After dissolution, n-BuLi (5.18 ml, 0.081 mol) was gradually added at −78□, and the reaction mixture was stirred for one hour at a maintained temperature. Then, 9-bromo-13,13-dimethyl-6H-indeno[1,2-b]anthracene-6,11(13H)-dione (10.88 g, 0.027 mol) was added and the reaction mixture was stirred at room temperature for 12 hours. The reaction solution was washed with distilled water, extracted with ethyl acetate, and purified by column chromatography to give 9-bromo-13,13-dimethyl-6,11-di(naphthalen-2-yl)-11,13-dihydro-6H-indeno[1,2-b]anthracene-6,11-diol (12 g, yield=67%).

$^1$H-NMR (500 MHz, THF-d8): 8.06 (d, 1H), 8.02 (d, 2H), 7.64 (d, 2H), 7.61 (d, 3H), 7.58 (t, 2H), 7.55 (t, 2H), 7.45 (m, 5H), 7.36 (d, 1H), 7.24 (m, 3H), 7.18 (s, 2H), 1.59 (s, 6H)

Synthesis Example 21

Preparation of 9-bromo-13,13-dimethyl-6,11-di(naphthalen-2-yl)-13H-indeno[1,2-b]anthracene 9-bromo-13,13-dimethyl-6,11-di(naphthalen-2-yl)-11,13-dihydro-6H-indeno[1,2-b]anthracene-6,11-diol (11.87 g, 0.018 mol), Potassium iodide (29.88 g, 0.18 mol), and Sodium hypophosphite (35.63 g, 0.297 mol) were placed in a flask, and were suspended in acetic acid (300 ml). The reaction mixture was stirred for five hours while heating. After the reaction was terminated, the reaction solution was added to an excess of distilled water. The resultant solid was washed, filtered and purified by column chromatography to give 9-bromo-13,13-dimethyl-6,11-di(naphthalen-2-yl)-13H-indeno[1,2-b]anthracene (8 g, yield=71%).

$^1$H-NMR (500 MHz, THF-d8): 8.14 (s, 1H), 8.10 (d, 2H), 8.06 (m, 2H), 8.01 (d, 2H), 7.92 (d, 2H), 7.82 (d, 1H), 7.73 (m, 3H), 7.61 (d, 1H), 7.59 (m, 6H), 7.53 (d, 1H), 7.44 (t, 1H), 7.24 (t, 1H), 1.75 (s, 6H)

Example 53

Preparation of Inv-72

9-bromo-13,13-dimethyl-6,11-di(naphthalen-2-yl)-13H-indeno[1,2-b]anthracene (5 g, 0.0079 mol) and 1-phenyl-1H-benzo[d]imidazol-2-yl boronic acid (1.88 g, 0.0079 mol) were dissolved in toluene (150 ml). Then, synthesis was carried out in the same manner as in Example 1 to give Inv-72 (3.2 g, yield=55%).

GC-Mass(FAB): (theoretical value: 738.91 g/mol, measured value: 738 g/mol)

Example 54

Preparation of Inv-81

9-bromo-13,13-dimethyl-6,11-di(naphthalen-2-yl)-13H-indeno[1,2-b]anthracene (5 g, 0.0079 mol) and 4-(1-phenyl-1H-benzo[d]imidazol-2-yl)phenylboronic acid (2.48 g, 0.0079 mol) were dissolved in toluene (150 ml). Then, synthesis was carried out in the same manner as in Example 1 to give Inv-81 (4.1 g, yield=64%).

GC-Mass(FAB): (theoretical value: 815.01 g/mol, measured value: 815 g/mol)

Example 55

Preparation of Inv-90

9-bromo-13,13-dimethyl-6,11-di(naphthalen-2-yl)-13H-indeno[1,2-b]anthracene (5 g, 0.0079 mol) and 3-(1-phenyl-1H-benzo[d]imidazol-2-yl)phenylboronic acid (2.48 g, 0.0079 mol) were dissolved in toluene (150 ml). Then, synthesis was carried out in the same manner as in Example 1 to give Inv-90 (4.6 g, yield=68%).

GC-Mass(FAB): (theoretical value: 815.01 g/mol, measured value: 814 g/mol)

Example 56

Preparation of Inv-99

9-bromo-13,13-dimethyl-6,11-di(naphthalen-2-yl)-13H-indeno[1,2-b]anthracene (5 g, 0.0079 mol) and benzo[d]oxazol-2-ylboronic acid (1.29 g, 0.0079 mol) were dissolved in toluene (150 ml). Then, synthesis was carried out in the same manner as in Example 1 to give Inv-99 (2.8 g, yield=53%).

GC-Mass(FAB): (theoretical value: 663.80 g/mol, measured value: 663 g/mol)

Example 57

Preparation of Inv-108

9-bromo-13,13-dimethyl-6,11-di(naphthalen-2-yl)-13H-indeno[1,2-b]anthracene (5 g, 0.0079 mol) and 4-(benzo[d]

oxazol-2-yl)phenylboronic acid (1.88 g, 0.0079 mol) were dissolved in toluene (150 ml). Then, synthesis was carried out in the same manner as in Example 1 to give Inv-108 (3.9 g, yield=67%).

GC-Mass(FAB): (theoretical value: 739.90 g/mol, measured value: 739 g/mol)

Example 58

Preparation of Inv-118

9-bromo-13,13-dimethyl-6,11-di(naphthalen-2-yl)-13H-indeno[1,2-b]anthracene (5 g, 0.0079 mol) and benzo[d]thiazol-2-ylboronic acid (1.41 g, 0.0079 mol) were dissolved in toluene (150 ml). Then, synthesis was carried out in the same manner as in Example 1 to give Inv-118 (3.1 g, yield=57%).

GC-Mass(FAB): (theoretical value: 679.87 g/mol, measured value: 679 g/mol)

Example 59

Preparation of Inv-127

9-bromo-13,13-dimethyl-6,11-di(naphthalen-2-yl)-13H-indeno[1,2-b]anthracene (5 g, 0.0079 mol) and 4-(benzo[d]thiazol-2-yl)phenylboronic acid (2.01 g, 0.0079 mol) were dissolved in toluene (150 ml). Then, synthesis was carried out in the same manner as in Example 1 to give Inv-127 (4.4 g, yield=74%).

GC-Mass(FAB): (theoretical value: 755.96 g/mol, measured value: 755 g/mol)

Synthesis Example 22

Preparation of 9-bromo-13,13-dimethyl-6,11-di(naphthalen-1-yl)-11,13-dihydro-6H-indeno[1,2-b]anthracene-6,11-diol 9-bromo-13,13-dimethyl-6,11-di(naphthalen-1-yl)-11,13-dihydro-6H-indeno[1,2-b]anthracene-6,11-diol (9.85 g, yield=55%) was obtained in the same manner as in Synthesis Example 20 except that instead of 2-Bromonaphthalene, 1-Bromonaphthalene (16.77 g, 0.081 mol) was added.

GC-Mass(FAB): (theoretical value: 659.61 g/mol, measured value: 659 g/mol)

Synthesis Example 23

Preparation of 9-bromo-13,13-dimethyl-6,11-di(naphthalen-1-yl)-13H-indeno[1,2-b]anthracene 9-bromo-13,13-dimethyl-6,11-di(naphthalen-1-yl)-11,13-dihydro-6H-indeno[1,2-b]anthracene-6,11-diol (11.87 g, 0.018 mol), potassium iodide (29.88 g, 0.18 mol), and sodium hypophosphite (35.63 g, 0.297 mol) were placed in a flask, and were suspended in acetic acid (300 ml). The reaction mixture was stirred for five hours while heating. After the reaction was terminated, the reaction solution was added to an excess of distilled water. The resultant solid was washed with distilled water, filtered, and purified by column chromatography to give 9-bromo-13,13-dimethyl-6,11-di(naphthalen-1-yl)-13H-indeno[1,2-b]anthracene (6.5 g, yield=57%)

GC-Mass(FAB): (theoretical value: 625.59 g/mol, measured value: 625 g/mol)

Example 60

Preparation of Inv-73

9-bromo-13,13-dimethyl-6,11-di(naphthalen-1-yl)-13H-indeno[1,2-b]anthracene (5 g, 0.0079 mol) and 1-phenyl-1H-benzo[d]imidazol-2-yl boronic acid (1.88 g, 0.0079 mol) were dissolved in toluene (150 ml). Then, synthesis was carried out in the same manner as in Example 1 to give Inv-73 (3.0 g, yield=51%).

GC-Mass(FAB): (theoretical value: 738.91 g/mol, measured value: 738 g/mol)

Example 61

Preparation of Inv-82

9-bromo-13,13-dimethyl-6,11-di(naphthalen-1-yl)-13H-indeno[1,2-b]anthracene (5 g, 0.0079 mol) and 4-(1-phenyl-1H-benzo[d]imidazol-2-yl)phenylboronic acid (2.48 g, 0.0079 mol) were dissolved in toluene (150 ml). Then, synthesis was carried out in the same manner as in Example 1 to give Inv-82 (3.9 g, yield=61%).

GC-Mass(FAB): (theoretical value: 815.01 g/mol, measured value: 815 g/mol)

Example 62

Preparation of Inv-91

9-bromo-13,13-dimethyl-6,11-di(naphthalen-1-yl)-13H-indeno[1,2-b]anthracene (5 g, 0.0079 mol) and 3-(1-phenyl-1H-benzo[d]imidazol-2-yl)phenylboronic acid (2.48 g, 0.0079 mol) were dissolved in toluene (150 ml). Then, synthesis was carried out in the same manner as in Example 1 to give Inv-91 (4.2 g, yield=65%).

GC-Mass(FAB): (theoretical value: 815.01 g/mol, measured value: 814 g/mol)

Example 63

Preparation of Inv-100

9-bromo-13,13-dimethyl-6,11-di(naphthalen-1-yl)-13H-indeno[1,2-b]anthracene (5 g, 0.0079 mol) and benzo[d]oxazol-2-ylboronic acid (1.29 g, 0.0079 mol) were dissolved in toluene (150 ml). Then, synthesis was carried out in the same manner as in Example 1 to give Inv-100 (2.5 g, yield=48%).

GC-Mass(FAB): (theoretical value: 663.80 g/mol, measured value: 663 g/mol)

Example 64

Preparation of Inv-109

9-bromo-13,13-dimethyl-6,11-di(naphthalen-1-yl)-13H-indeno[1,2-b]anthracene (5 g, 0.0079 mol) and 4-(benzo[d]oxazol-2-yl)phenylboronic acid (1.88 g, 0.0079 mol) were dissolved in toluene (150 ml). Then, synthesis was carried out in the same manner as in Example 1 to give Inv-109 (4.1 g, yield=70%).

GC-Mass(FAB): (theoretical value: 739.90 g/mol, measured value: 739 g/mol)

Example 65

Preparation of Inv-119

9-bromo-13,13-dimethyl-6,11-di(naphthalen-1-yl)-13H-indeno[1,2-b]anthracene (5 g, 0.0079 mol) and benzo[d]thiazol-2-ylboronic acid (1.41 g, 0.0079 mol) were dissolved in toluene (150 ml). Then, synthesis was carried out in the same manner as in Example 1 to give Inv-119 (3.5 g, yield=65%).

GC-Mass(FAB): (theoretical value: 679.87 g/mol, measured value: 679 g/mol)

Example 66

Preparation of Inv-128

9-bromo-13,13-dimethyl-6,11-di(naphthalen-1-yl)-13H-indeno[1,2-b]anthracene (5 g, 0.0079 mol) and 4-(benzo[d]thiazol-2-yl)phenylboronic acid (2.01 g, 0.0079 mol) were dissolved in toluene (150 ml). Then, synthesis was carried out in the same manner as in Example 1 to give Inv-128 (4.1 g, yield=69%).

GC-Mass(FAB): (theoretical value: 755.96 g/mol, measured value: 755 g/mol)

Synthesis Example 24

Preparation of 6,11-di(biphenyl-4-yl)-9-bromo-13,13-dimethyl-11,13-dihydro-6H-indeno[1,2-b]anthracene-6,11-diol 4-bromobiphenyl (12.58 g, 0.054 mol) was placed in a flask and THF (200 ml) was added thereto. After dissolution, n-BuLi (38.4 ml, 0.06 mol) was gradually added at −780, and the reaction mixture was stirred for one hour at a maintained temperature. Then, 9-bromo-13,13-dimethyl-6H-indeno[1,2-b]anthracene-6,11(13H)-dione (10 g, 0.024 mol) was added, and the reaction mixture was stirred at room temperature for 15 hours. After the reaction was terminated, the reaction solution was washed with distilled water, extracted with ethyl acetate, and purified by column chromatography to give 6,11-di(biphenyl-4-yl)-9-bromo-13,13-dimethyl-11,13-dihydro-6H-indeno[1,2-b]anthracene-6,11-diol (9.2 g, yield=54%).

GC-Mass(FAB): (theoretical value: 711.68 g/mol, measured value: 711 g/mol)

Synthesis Example 25

Preparation of 6,11-di(biphenyl-4-yl)-9-bromo-13,13-dimethyl-13H-indeno[1,2-b]anthracene 6,11-di(biphenyl-4-yl)-9-bromo-13,13-dimethyl-13H-indeno[1,2-b]anthracene (3.1 g, yield=61%) was obtained in the same manner as in Synthesis Example 7 except that 6,11-di(biphenyl-4-yl)-9-bromo-13,13-dimethyl-11,13-dihydro-6H-indeno[1,2-b]anthracene-6,11-diol (5.33 g, 0.0075 mol) was added.

GC-Mass(FAB): (theoretical value: 677.67 g/mol, measured value: 677 g/mol)

Example 67

Preparation of Inv-74

6,11-di(biphenyl-4-yl)-9-bromo-13,13-dimethyl-13H-indeno[1,2-b]anthracene (5 g, 0.0074 mol) and 1-phenyl-1H-benzo[d]imidazol-2-yl boronic acid (1.76 g, 0.0074 mol) were dissolved in toluene (150 ml). Then, synthesis was carried out in the same manner as in Example 1 to give Inv-74 (2.9 g, yield=50%).

GC-Mass(FAB): (theoretical value: 790.99 g/mol, measured value: 790 g/mol)

Example 68

Preparation of Inv-83

6,11-di(biphenyl-4-yl)-9-bromo-13,13-dimethyl-13H-indeno[1,2-b]anthracene (5 g, 0.0074 mol) and 4-(1-phenyl-1H-benzo[d]imidazol-2-yl)phenylboronic acid (2.32 g, 0.0074 mol) were dissolved in toluene (150 ml). Then, synthesis was carried out in the same manner as in Example 1 to give Inv-83 (4.9 g, yield=76%).

GC-Mass(FAB): (theoretical value: 867.08 g/mol, measured value: 867 g/mol)

Example 69

Preparation of Inv-92

6,11-di(biphenyl-4-yl)-9-bromo-13,13-dimethyl-13H-indeno[1,2-b]anthracene (5 g, 0.0074 mol) and 3-(1-phenyl-1H-benzo[d]imidazol-2-yl)phenylboronic acid (2.32 g, 0.0074 mol) were dissolved in toluene (150 ml). Then, synthesis was carried out in the same manner as in Example 1 to give Inv-92 (4.1 g, yield=64%).

GC-Mass(FAB): (theoretical value: 867.08 g/mol, measured value: 867 g/mol)

Example 70

Preparation of Inv-101

6,11-di(biphenyl-4-yl)-9-bromo-13,13-dimethyl-13H-indeno[1,2-b]anthracene (5 g, 0.0074 mol) and benzo[d]oxazol-2-ylboronic acid (1.2 g, 0.0074 mol) were dissolved in toluene (150 ml). Then, synthesis was carried out in the same manner as in Example 1 to give Inv-101 (2.8 g, yield=53%).

GC-Mass(FAB): (theoretical value: 715.88 g/mol, measured value: 715 g/mol)

Example 71

Preparation of Inv-110

6,11-di(biphenyl-4-yl)-9-bromo-13,13-dimethyl-13H-indeno[1,2-b]anthracene (5 g, 0.0074 mol) and 4-(benzo[d]oxazol-2-yl)phenylboronic acid (1.76 g, 0.0074 mol) were dissolved in toluene (150 ml). Then, synthesis was carried out in the same manner as in Example 1 to give Inv-110 (3.4 g, yield=58%).

GC-Mass(FAB): (theoretical value: 791.97 g/mol, measured value: 791 g/mol)

Example 72

Preparation of Inv-120

6,11-di(biphenyl-4-yl)-9-bromo-13,13-dimethyl-13H-indeno[1,2-b]anthracene (5 g, 0.0074 mol) and benzo[d]thiazol-2-ylboronic acid (1.32 g, 0.0074 mol) were dissolved in toluene (150 ml). Then, synthesis was carried out in the same manner as in Example 1 to give Inv-120 (3.5 g, yield=65%).

GC-Mass(FAB): (theoretical value: 731.94 g/mol, measured value: 731 g/mol)

Example 73

Preparation of Inv-129

6,11-di(biphenyl-4-yl)-9-bromo-13,13-dimethyl-13H-indeno[1,2-b]anthracene (5 g, 0.0074 mol) and 4-(benzo[d]thiazol-2-yl)phenylboronic acid (1.88 g, 0.0074 mol) were dissolved in toluene (150 ml). Then, synthesis was carried out in the same manner as in Example 1 to give Inv-129 (4.1 g, yield=69%).

GC-Mass(FAB): (theoretical value: 808.04 g/mol, measured value: 807 g/mol)

Synthesis Example 26

Preparation of 9-bromo-6,11-bis(9,9-dimethyl-9H-fluoren-2-yl)-13,13-dimethyl-11,13-dihydro-6H-indeno[1,2-b]anthracene-6,11-diol 2-bromo-9,9-dimethyl-9H-fluorene (14.75 g, 0.054 mol) was placed in a flask, THF (200 ml) was added thereto. After dissolution, n-BuLi (38.4 ml, 0.06 mol) was gradually added at −780, and the reaction mixture was stirred for one hour at a maintained temperature. Then, 9-bromo-13,13-dimethyl-6H-indeno[1,2-b]anthracene-6,11(13H)-dione (9.67 g, 0.024 mol) was added and the reaction mixture was stirred at room temperature for 12 hours. After the reaction was terminated, the reaction solution was washed with distilled water, extracted with ethyl acetate, and purified by column chromatography to give 9-bromo-6,11-bis(9,9-dimethyl-9H-fluoren-2-yl)-13,13-dimethyl-11,13-dihydro-6H-indeno[1,2-b]anthracene-6,11-diol (11.2 g, yield=66%).

GC-Mass(FAB): (theoretical value: 791.81 g/mol, measured value: 791 g/mol)

Synthesis Example 27

Preparation of 9-bromo-6,11-bis(9,9-dimethyl-9H-fluoren-2-yl)-13,13-dimethyl-13H-indeno[1,2-b]anthracene 9-bromo-6,11-bis(9,9-dimethyl-9H-fluoren-2-yl)-13,13-dimethyl-13H-indeno[1,2-b]anthracene (3.2 g, yield=56%) was obtained in the same manner as in Synthesis Example 7 except that 9-bromo-6,11-bis(9,9-dimethyl-9H-fluoren-2-yl)-13,13$^{dimethyl}$-11,13-dihydro-6H-indeno[1,2-b]anthracene-6,11-diol (5.94 g, 0.0075 mol) was added.

GC-Mass(FAB): (theoretical value: 757.80 g/mol, measured value: 757 g/mol)

Example 74

Preparation of Inv-77

9-bromo-6,11-bis(9,9-dimethyl-9H-fluoren-2-yl)-13,13-dimethyl-13H-indeno[1,2-b]anthracene (5 g, 0.0066 mol) and 1-phenyl-1H-benzo[d]imidazol-2-yl boronic acid (1.57 g, 0.0066 mol) were dissolved in toluene (150 ml). Then, synthesis was carried out in the same manner as in Example 1 to give Inv-77 (3.3 g, yield=57%).

GC-Mass(FAB): (theoretical value: 871.12 g/mol, measured value: 871 g/mol)

Example 75

Preparation of Inv-86

9-bromo-6,11-bis(9,9-dimethyl-9H-fluoren-2-yl)-13,13-dimethyl-13H-indeno[1,2-b]anthracene (5 g, 0.0066 mol) and 4-(1-phenyl-1H-benzo[d]imidazol-2-yl)phenylboronic acid (2.07 g, 0.0066 mol) were dissolved in toluene (150 ml). Then, synthesis was carried out in the same manner as in Example 1 to give Inv-86 (5.0 g, yield=80%).

GC-Mass(FAB): (theoretical value: 947.21 g/mol, measured value: 947 g/mol)

Example 76

Preparation of Inv-95

9-bromo-6,11-bis(9,9-dimethyl-9H-fluoren-2-yl)-13,13-dimethyl-13H-indeno[1,2-b]anthracene (5 g, 0.0066 mol) and 3-(1-phenyl-1H-benzo[d]imidazol-2-yl)phenylboronic acid (2.07 g, 0.0066 mol) were dissolved in toluene (150 ml). Then, synthesis was carried out in the same manner as in Example 1 to give Inv-95 (4.7 g, yield=75%).

GC-Mass(FAB): (theoretical value: 947.21 g/mol, measured value: 947 g/mol)

Example 77

Preparation of Inv-104

9-bromo-6,11-bis(9,9-dimethyl-9H-fluoren-2-yl)-13,13-dimethyl-13H-indeno[1,2-b]anthracene (5 g, 0.0066 mol) and benzo[d]oxazol-2-ylboronic acid (1.07 g, 0.0066 mol) were dissolved in toluene (150 ml). Then, synthesis was carried out in the same manner as in Example 1 to give Inv-104 (3.0 g, yield=57%).

GC-Mass(FAB): (theoretical value: 796.01 g/mol, measured value: 795 g/mol)

Example 78

Preparation of Inv-114

9-bromo-6,11-bis(9,9-dimethyl-9H-fluoren-2-yl)-13,13-dimethyl-13H-indeno[1,2-b]anthracene (5 g, 0.0066 mol) and 4-(benzo[d]oxazol-2-yl)phenylboronic acid (1.57 g, 0.0066 mol) were dissolved in toluene (150 ml). Then, synthesis was carried out in the same manner as in Example 1 to give Inv-114 (3.1 g, yield=54%).

GC-Mass(FAB): (theoretical value: 872.10 g/mol, measured value: 872 g/mol)

Example 79

Preparation of Inv-123

9-bromo-6,11-bis(9,9-dimethyl-9H-fluoren-2-yl)-13,13-dimethyl-13H-indeno[1,2-b]anthracene (5 g, 0.0066 mol) and benzo[d]thiazol-2-ylboronic acid (1.18 g, 0.0066 mol) were dissolved in toluene (150 ml). Then, synthesis was carried out in the same manner as in Example 1 to give Inv-123 (3.0 g, yield=56%).

GC-Mass(FAB): (theoretical value: 812.07 g/mol, measured value: 811 g/mol)

Synthesis Example 28

Preparation of 9-bromo-13,13-dimethyl-6,11-di(phenanthren-9-yl)-11,13-dihydro-6H-indeno[1,2-b]anthracene-6,11-diol 9-bromophenanthrene (13.88 g, 0.054 mol) was placed in a flask, and THF (200 ml) was added thereto. After dissolution, n-BuLi (38.4 ml, 0.06 mol) was gradually added at −780, and the reaction mixture was stirred for one hour at a maintained temperature. Then, 9-bromo-13,13-dimethyl-6H-indeno[1,2-b]anthracene-6,11(13H)-dione (9.67 g, 0.024 mol) was added and the reaction mixture was stirred at room temperature for 12 hours. After the reaction was terminated, the reaction solution was washed with distilled water, extracted with ethyl acetate, and purified by column chromatography to give 9-bromo-13,13-dimethyl-6,11-di(phenanthren-9-yl)-11,13-dihydro6H-indeno[1,2-b]anthracene-6,11-diol (11.7 g, yield=64%).

GC-Mass(FAB): (theoretical value: 759.73 g/mol, measured value:759 g/mol)

Synthesis Example 29

Preparation of 9-bromo-13,13-dimethyl-6,11-di(phenanthren-9-yl)-13H-indeno[1,2-b]anthracene 9-bromo-13,13-dimethyl-6,11-di(phenanthren-9-yl)-13H-indeno[1,2-b]anthracene (3.1 g, yield=67%) was obtained in the same manner as in Synthesis Example 7 except that 9-bromo-13,13-dimethyl-6,11-di(phenanthren-9-yl)-11,13-dihydro-6H-indeno[1,2-b]anthracene-6,11-diol (5.69 g, 0.0075 mol) was added.

GC-Mass(FAB): (theoretical value: 725.71 g/mol, measured value: 725 g/mol)

Example 80

Preparation of Inv-78

9-bromo-13,13-dimethyl-6,11-di(phenanthren-9-yl)-13H-indeno[1,2-b]anthracene (5 g, 0.0068 mol) and 1-phenyl-1H-benzo[d]imidazol-2-yl boronic acid (1.61 g, 0.0068 mol) were dissolved in toluene (150 ml). Then, synthesis was carried out in the same manner as in Example 1 to give Inv-78 (3.9 g, yield=68%).

GC-Mass(FAB): (theoretical value: 839.03 g/mol, measured value: 838 g/mol)

Example 81

Preparation of Inv-87

9-bromo-13,13-dimethyl-6,11-di(phenanthren-9-yl)-13H-indeno[1,2-b]anthracene (5 g, 0.0068 mol) and 4-(1-phenyl-1H-benzo[d]imidazol-2-yl)phenylboronic acid (2.14 g, 0.0068 mol) were dissolved in toluene (150 ml). Then, synthesis was carried out in the same manner as in Example 1 to give Inv-87 (4.5 g, yield=72%).

GC-Mass(FAB): (theoretical value: 915.13 g/mol, measured value: 915 g/mol)

Example 82

Preparation of Inv-96

9-bromo-13,13-dimethyl-6,11-di(phenanthren-9-yl)-13H-indeno[1,2-b]anthracene (5 g, 0.0068 mol) and 3-(1-phenyl-1H-benzo[d]imidazol-2-yl)phenylboronic acid (2.14 g, 0.0068 mol) were dissolved in toluene (150 ml). Then, synthesis was carried out in the same manner as in Example 1 to give Inv-96 (3.9 g, yield=63%).

GC-Mass(FAB): (theoretical value: 915.13 g/mol, measured value: 915 g/mol)

Example 83

Preparation of Inv-105

9-bromo-13,13-dimethyl-6,11-di(phenanthren-9-yl)-13H-indeno[1,2-b]anthracene (5 g, 0.0068 mol) and benzo[d]oxazol-2-ylboronic acid (1.11 g, 0.0068 mol) were dissolved in toluene (150 ml). Then, synthesis was carried out in the same manner as in Example 1 to give Inv-105 (3.4 g, yield=65%).

GC-Mass(FAB): (theoretical value: 763.92 g/mol, measured value: 763 g/mol)

Example 84

Preparation of Inv-115

9-bromo-13,13-dimethyl-6,11-di(phenanthren-9-yl)-13H-indeno[1,2-b]anthracene (5 g, 0.0068 mol) and 4-(benzo[d]oxazol-2-yl)phenylboronic acid (1.63 g, 0.0068 mol) were dissolved in toluene (150 ml). Then, synthesis was carried out in the same manner as in Example 1 to give Inv-115 (2.9 g, yield=50%).

GC-Mass(FAB): (theoretical value: 840.02 g/mol, measured value: 839 g/mol)

Synthesis Example 30

Preparation of 2-(9,9-dimethyl-9H-fluorene-2-carbonyl)benzoic acid

Fluorene (20 g, 0.102 mol) and phthalic anhydride (22.87 g, 0.154 mol) were placed in a reaction vessel and dichloromethane (400 ml) was added thereto. Then, aluminum chloride (20.53 g, 0.154 mol) was gradually added at 012, and the reaction mixture was stirred at room temperature for 12 hours. After the reaction was terminated, distilled water was gradually added, and the reaction solution was extracted with an excess of dichloromethane and washed three times with distilled water. After solvent removal, the resultant solid was placed in a hexane(1)-containing vessel, washed, filtered and dried to give 2-(9,9-dimethyl-9H-fluorene-2-carbonyl)benzoic acid (27 g, yield=76%).

$^1$H-NMR (500 MHz, THF-d8): 8.32 (t, 1H), 8.23 (d, 1H), 7.94 (d, 1H), 7.90 (m, 2H), 7.84 (d, 1H), 7.82 (d, 1H), 7.66 (t, 1H), 7.55 (d, 1H), 7.30 (m, 2H), 1.64 (s, 6H).

Synthesis Example 31

Preparation of 13,13-dimethyl-6H-indeno[1,2-b]anthracene-6,11(13H)-dione 2-(9,9-dimethyl-9H-fluorene-2-carbonyl)benzoic acid (27 g, 0.079 mol) was placed in a flask, polyphosphoric acid (300 ml) was added thereto. The mixture was heated at 140° C. for 2 hours and cooled to less than 50□, and distilled water was gradually added thereto. The resultant solid was filtered, washed with a small amount of methanol, and dried to give a required compound, 13,13-dimethyl-6H-indeno[1,2-b]anthracene-6,11(13H)-dione (19 g, yield=74%).

$^1$H NMR (500 MHz, THF-d8): 8.38 (s, 1H), 8.30 (t, 2H), 8.09 (s, 1H), 7.85 (d, 2H), 7.70 (d, 1H), 7.55 (d, 1H), 7.30 (t, 2H), 1.57 (s, 6H)

Synthesis Example 32

Preparation of 13,13-dimethyl-13H-indeno[1,2-b]anthracene 13,13-dimethyl-6H-indeno[1,2-b]anthracene-6,11(13H)-dione (19 g, 0.058 mol) was dissolved in acetic acid (200 ml) and 57% HI (50 ml) was added thereto. The reaction mixture was stirred under reflux for 48 hours. After the reaction was terminated, the reaction solution was added with distilled water (500 ml). Then, the resultant solid was filtered and dissolved in toluene (200 ml), and iodine (4.56 g, 0.018 mol) was added thereto. The reaction mixture was stirred under reflux for 3 hours. After the reaction was terminated, the reaction solution was extracted and purified by column chromatography to give 13,13-dimethyl-13H-indeno[1,2-b]anthracene (10 g, yield=58%).

$^1$H NMR (500 MHz, THF-d8): 8.30 (s, 1H), 8.22 (s, 2H), 8.06 (d, 1H), 7.91 (d, 2H), 7.76 (s, 1H), 7.50 (m, 3H), 7.39 (t, 2H), 1.75 (s, 6H)

Synthesis Example 33

Preparation of 11-bromo-13,13-dimethyl-13H-indeno[1,2-b]anthracene 13,13-dimethyl-13H-indeno[1,2-b]anthracene (10 g, 0.034 mol) and N-bromosuccinimide (7.68 g, 0.034 mol) were dissolved in carbon tetrachloride (200 ml), and the reaction mixture was stirred for 8 hours at 60° C. After the reaction was terminated, the reaction solution was extracted with distilled water, and purified by column chromatography to give 11-bromo-13,13-dimethyl-13H-indeno[1,2-b]anthracene (9 g, yield=71%).

$^1$H NMR (500 MHz, THF-d8): 8.30 (s, 1H), 8.25 (d, 1H), 8.06 (m, 3H), 7.76 (s, 1H), 7.61 (d, 1H), 7.55 (m, 3H), 7.24 (t, 1H), 1.72 (s, 6H),

Synthesis Example 34

Preparation of 13,13-dimethyl-11-phenyl-13H-indeno[1,2-b]anthracene 11-bromo-13,13-dimethyl-13H-indeno[1,2-b]anthracene (9 g, 0.0241 mol), bromobenzene (5.65 g, 0.036 mol), Pd(PPh$_3$)$_4$ (0.83 g, 0.00072 mol), and Na$_2$CO$_3$ (7.6 g, 0.072 mol) were placed in a flask and dissolved in toluene (150 ml) and distilled water (40 ml). The reaction mixture was stirred under reflux for 4 hours. After the reaction was terminated, the reaction solution was extracted with methylene chloride, and purified by column chromatography to give 13,13-dimethyl-11-phenyl-13H-indeno[1,2-b]anthracene (6.5 g, yield=73%).

GC-Mass(FAB): (theoretical value: 370.48 g/mol, measured value: 370 g/mol)

Synthesis Example 35

Preparation of 6-bromo-13,13-dimethyl-11-phenyl-13H-indeno[1,2-b]anthracene 13,13-dimethyl-11-phenyl-13H-indeno[1,2-b]anthracene (6.3 g, 0.017 mol) and N-bromosuccinimide (3.76 g, 0.017 mol) were dissolved in carbon tetrachloride (150 ml), and the reaction mixture was stirred under reflux for 4 hours at 60° C. After the reaction was terminated, the reaction solution was extracted with distilled water, and purified by column chromatography to give 6-bromo-13,13-dimethyl-11-phenyl-13H-indeno[1,2-b]anthracene (5.2 g, yield=68%).

GC-Mass(FAB): (theoretical value: 449.38 g/mol, measured value: 449 g/mol)

Example 85

Preparation of Inv-152

6-bromo-13,13-dimethyl-11-phenyl-13H-indeno[1,2-b]anthracene (5 g, 0.011 mol) and 4-(1-phenyl-1H-benzo[d]imidazol-2-yl)phenylboronic acid (3.5 g, 0.011 mol) were dissolved in toluene (200 ml). Then, synthesis was carried out in the same manner as in Example 1 to give Inv-152 (5.2 g, yield=74%).

GC-Mass(FAB): (theoretical value: 638.80 g/mol, measured value: 638 g/mol)

Example 86

Preparation of Inv-171

6-bromo-13,13-dimethyl-11-phenyl-13H-indeno[1,2-b]anthracene (5 g, 0.011 mol) and 3-(1-phenyl-1H-benzo[d]imidazol-2-yl)phenylboronic acid (3.5 g, 0.011 mol) were dissolved in toluene (200 ml). Then, synthesis was carried out in the same manner as in Example 1 to give Inv-171 (5.4 g, yield=77%).

GC-Mass(FAB): (theoretical value: 638.80 g/mol, measured value: 638 g/mol)

Example 87

Preparation of Inv-181

6-bromo-13,13-dimethyl-11-phenyl-13H-indeno[1,2-b]anthracene (5 g, 0.011 mol) and benzo[d]oxazol-2-ylboronic acid (1.79 g, 0.011 mol) were dissolved in toluene (200 ml). Then, synthesis was carried out in the same manner as in Example 1 to give Inv-181 (3.5 g, yield=65%).

GC-Mass(FAB): (theoretical value: 487.59 g/mol, measured value: 487 g/mol)

Example 88

Preparation of Inv-191

6-bromo-13,13-dimethyl-11-phenyl-13H-indeno[1,2-b]anthracene (5 g, 0.011 mol) and benzo[d]thiazol-2-ylboronic acid (1.97 g, 0.011 mol) were dissolved in toluene (200 ml). Then, synthesis was carried out in the same manner as in Example 1 to give Inv-191 (3.5 g, yield=63%).

GC-Mass(FAB): (theoretical value: 503.66 g/mol, measured value: 503 g/mol)

Example 89

Preparation of Inv-201

6-bromo-13,13-dimethyl-11-phenyl-13H-indeno[1,2-b]anthracene (5 g, 0.011 mol) and 4-(benzo[d]oxazol-2-yl)phenylboronic acid (2.63 g, 0.011 mol) were dissolved in toluene (200 ml). Then, synthesis was carried out in the same manner as in Example 1 to give Inv-201 (4.1 g, yield=66%).

GC-Mass(FAB): (theoretical value: 563.69 g/mol, measured value: 563 g/mol)

Example 90

Preparation of Inv-211

6-bromo-13,13-dimethyl-11-phenyl-13H-indeno[1,2-b]anthracene (5 g, 0.011 mol) and 4-(benzo[d]thiazol-2-yl)phenylboronic acid (2.80 g, 0.011 mol) were dissolved in toluene (200 ml). Then, synthesis was carried out in the same manner as in Example 1 to give Inv-211 (4.3 g, yield=67%).

GC-Mass(FAB): (theoretical value: 579.75 g/mol, measured value: 579 g/mol)

Example 91

Preparation of Inv-221

6-bromo-13,13-dimethyl-11-phenyl-13H-indeno[1,2-b]anthracene (5 g, 0.011 mol) and 5-(4,4,5,5-tetramethyl-1,3,2-dioxaborolan-2-yl)-2,2'-bipyridine (3.10 g, 0.011 mol) were dissolved in toluene (200 ml). Then, synthesis was carried out in the same manner as in Example 1 to give Inv-221 (3.8 g, yield=66%).

GC-Mass(FAB): (theoretical value: 524.65 g/mol, measured value: 524 g/mol)

Synthesis Example 36

Preparation of 13,13-dimethyl-11-(naphthalen-2-yl)-13H-indeno[1,2-b]anthracene 13,13-dimethyl-11-(naphthalen-2-yl)-13H-indeno[1,2-b]anthracene (7.2 g, yield=71%) was obtained in the same manner as in Synthesis Example 34 except that 11-bromo-13,13-dimethyl-13H-indeno[1,2-b]anthracene (9 g, 0.0241 mol) and Naphthalen-2-ylboronic acid (6.19 g, 0.036 mol) were added.

GC-Mass(FAB): (theoretical value: 420.54 g/mol, measured value: 420 g/mol)

Synthesis Example 37

Preparation of 6-bromo-13,13-dimethyl-11-(naphthalen-2-yl)-13H-indeno[1,2-b]anthracene 6-bromo-13,13-dimethyl-11-(naphthalen-2-yl)-13H-indeno[1,2-b]anthracene (6.3 g, yield=74%) was obtained in the same manner as in Synthesis Example 35 except that 13,13-dimethyl-11-(naphthalen-2-yl)-13H-indeno[1,2-b]anthracene (7.15 g, 0.017 mol) was added.

GC-Mass(FAB): (theoretical value: 499.44 g/mol, measured value: 499 g/mol)

Example 92

Preparation of Inv-153

6-bromo-13,13-dimethyl-11-(naphthalen-2-yl)-13H-indeno[1,2-b]anthracene (5.49 g, 0.011 mol) and 4-(1-phenyl-1H-benzo[d]imidazol-2-yl)phenylboronic acid (3.5 g, 0.011 mol) were dissolved in toluene (200 ml). Then, synthesis was carried out in the same manner as in Example 1 to give Inv-153 (5.8 g, yield=77%).

GC-Mass(FAB): (theoretical value: 688.86 g/mol, measured value: 688 g/mol)

Example 93

Preparation of Inv-172

6-bromo-13,13-dimethyl-11-(naphthalen-2-yl)-13H-indeno[1,2-b]anthracene (5.49 g, 0.011 mol) and 3-(1-phenyl-1H-benzo[d]imidazol-2-yl)phenylboronic acid (3.5 g, 0.011 mol) were dissolved in toluene (200 ml). Then, synthesis was carried out in the same manner as in Example 1 to give Inv-172 (5.4 g, yield=71%).

GC-Mass(FAB): (theoretical value: 688.86 g/mol, measured value: 688 g/mol)

Example 94

Preparation of Inv-182

6-bromo-13,13-dimethyl-11-(naphthalen-2-yl)-13H-indeno[1,2-b]anthracene (5.49 g, 0.011 mol) and benzo[d]oxazol-2-ylboronic acid (1.79 g, 0.011 mol) were dissolved in toluene (200 ml). Then, synthesis was carried out in the same manner as in Example 1 to give Inv-182 (4.1 g, yield=69%).

GC-Mass(FAB): (theoretical value: 537.67 g/mol, measured value: 537 g/mol)

Example 95

Preparation of Inv-192

6-bromo-13,13-dimethyl-11-(naphthalen-2-yl)-13H-indeno[1,2-b]anthracene (5.49 g, 0.011 mol) and benzo[d]thiazol-2-ylboronic acid (1.97 g, 0.011 mol) were dissolved in toluene (200 ml). Then, synthesis was carried out in the same manner as in Example 1 to give Inv-192 (3.8 g, yield=62%).

GC-Mass(FAB): (theoretical value: 553.71 g/mol, measured value: 553 g/mol)

Example 96

Preparation of Inv-202

6-bromo-13,13-dimethyl-11-(naphthalen-2-yl)-13H-indeno[1,2-b]anthracene (5.49 g, 0.011 mol) and 4-(benzo[d]oxazol-2-yl)phenylboronic acid (2.63 g, 0.011 mol) were dissolved in toluene (200 ml). Then, synthesis was carried out in the same manner as in Example 1 to give Inv-202 (4.3 g, yield=63%).

GC-Mass(FAB): (theoretical value: 613.74 g/mol, measured value: 613 g/mol)

Example 97

Preparation of Inv-212

6-bromo-13,13-dimethyl-11-(naphthalen-2-yl)-13H-indeno[1,2-b]anthracene (5.49 g, 0.011 mol) and 4-(benzo[d]thiazol-2-yl)phenylboronic acid (2.80 g, 0.011 mol) were dissolved in toluene (200 ml). Then, synthesis was carried out in the same manner as in Example 1 to give Inv-212 (3.9 g, yield=56%).

GC-Mass(FAB): (theoretical value: 629.81 g/mol, measured value: 629 g/mol)

Example 98

Preparation of Inv-222

6-bromo-13,13-dimethyl-11-(naphthalen-2-yl)-13H-indeno[1,2-b]anthracene (5.49 g, 0.011 mol) and 5-(4,4,5,5-tetramethyl-1,3,2-dioxaborolan-2-yl)-2,2'-bipyridine (3.10 g, 0.011 mol) were dissolved in toluene (200 ml). Then, synthesis was carried out in the same manner as in Example 1 to give Inv-222 (4.2 g, yield=66%).

GC-Mass(FAB): (theoretical value: 574.74 g/mol, measured value: 574 g/mol)

Synthesis Example 38

Preparation of 13,13-dimethyl-11-(naphthalen-1-yl)-13H-indeno[1,2-b]anthracene 13,13-dimethyl-11-(naphthalen-1-yl)-13H-indeno[1,2-b]anthracene (7.8 g, yield=76%) was obtained in the same manner as in Synthesis Example 34 except that 11-bromo-13,13-dimethyl-13H-indeno[1,2-b]anthracene (9 g, 0.0241 mol) and Naphthalen-1-ylboronic acid (6.19 g, 0.036 mol) were added.

GC-Mass(FAB): (theoretical value: 420.54 g/mol, measured value: 420 g/mol)

Synthesis Example 39

Preparation of 6-bromo-13,13-dimethyl-11-(naphthalen-1-yl)-13H-indeno[1,2-b]anthracene 6-bromo-13,13-dimethyl-11-(naphthalen-1-yl)-13H-indeno[1,2-b]anthracene (5.8 g, yield=68%) was obtained in the same manner as in Synthesis Example 35 except that 13,13-dimethyl-11-(naphthalen-1-yl)-13H-indeno[1,2-b]anthracene (7.15 g, 0.017 mol) was added.

GC-Mass(FAB): (theoretical value: 499.44 g/mol, measured value: 499 g/mol)

Example 99

Preparation of Inv-154

6-bromo-13,13-dimethyl-11-(naphthalen-1-yl)-13H-indeno[1,2-b]anthracene (5.49 g, 0.011 mol) and 4-(1-phenyl-1H-benzo[d]imidazol-2-yl)phenylboronic acid (3.5 g, 0.011 mol) were dissolved in toluene (200 ml). Then, synthesis was carried out in the same manner as in Example 1 to give Inv-154 (5.2 g, yield=69%).

GC-Mass(FAB): (theoretical value: 688.86 g/mol, measured value: 688 g/mol)

Example 100

Preparation of Inv-173

6-bromo-13,13-dimethyl-11-(naphthalen-1-yl)-13H-indeno[1,2-b]anthracene (5.49 g, 0.011 mol) and 3-(1-phenyl-1H-benzo[d]imidazol-2-yl)phenylboronic acid (3.5 g, 0.011 mol) were dissolved in toluene (200 ml). Then, synthesis was carried out in the same manner as in Example 1 to give Inv-173 (5.8 g, yield=76%).

GC-Mass(FAB): (theoretical value: 688.86 g/mol, measured value: 688 g/mol)

Example 101

Preparation of Inv-183

6-bromo-13,13-dimethyl-11-(naphthalen-1-yl)-13H-indeno[1,2-b]anthracene (5.49 g, 0.011 mol) and benzo[d]oxazol-2-ylboronic acid (1.79 g, 0.011 mol) were dissolved in toluene (200 ml). Then, synthesis was carried out in the same manner as in Example 1 to give Inv-183 (4.5 g, yield=76%).

GC-Mass(FAB): (theoretical value: 537.67 g/mol, measured value: 537 g/mol)

Example 102

Preparation of Inv-193

6-bromo-13,13-dimethyl-11-(naphthalen-1-yl)-13H-indeno[1,2-b]anthracene (5.49 g, 0.011 mol) and benzo[d]thiazol-2-ylboronic acid (1.97 g, 0.011 mol) were dissolved in toluene (200 ml). Then, synthesis was carried out in the same manner as in Example 1 to give Inv-193 (4.0 g, yield=66%).

GC-Mass(FAB): (theoretical value: 553.71 g/mol, measured value: 553 g/mol)

Example 103

Preparation of Inv-203

6-bromo-13,13-dimethyl-11-(naphthalen-1-yl)-13H-indeno[1,2-b]anthracene (5.49 g, 0.011 mol) and 4-(benzo[d]oxazol-2-yl)phenylboronic acid (2.63 g, 0.011 mol) were dissolved in toluene (200 ml). Then, synthesis was carried out in the same manner as in Example 1 to give Inv-203 (4.9 g, yield=73%).

GC-Mass(FAB): (theoretical value: 613.74 g/mol, measured value: 613 g/mol)

Example 104

Preparation of Inv-213

6-bromo-13,13-dimethyl-11-(naphthalen-1-yl)-13H-indeno[1,2-b]anthracene (5.49 g, 0.011 mol) and 4-(benzo[d]thiazol-2-yl)phenylboronic acid (2.80 g, 0.011 mol) were dissolved in toluene (200 ml). Then, synthesis was carried out in the same manner as in Example 1 to give Inv-213 (3.7 g, yield=53%).

GC-Mass(FAB): (theoretical value: 629.81 g/mol, measured value: 629 g/mol)

Example 105

Preparation of Inv-223

6-bromo-13,13-dimethyl-11-(naphthalen-1-yl)-13H-indeno[1,2-b]anthracene (5.49 g, 0.011 mol) and 5-(4,4,5,5-tetramethyl-1,3,2-dioxaborolan-2-yl)-2,2'-bipyridine (3.10 g, 0.011 mol) were dissolved in toluene (200 ml). Then, synthesis was carried out in the same manner as in Example 1 to give Inv-223 (5.3 g, yield=84%).

GC-Mass(FAB): (theoretical value: 574.74 g/mol, measured value: 574 g/mol)

Synthesis Example 40

Preparation of 11-(biphenyl-4-yl)-13,13-dimethyl-13H-indeno[1,2-b]anthracene 11-(biphenyl-4-yl)-13,13-dimethyl-13H-indeno[1,2-b]anthracene (8.1 g, yield=75%) was obtained in the same manner as in Synthesis Example 34 except that 11-bromo-13,13-dimethyl-13H-indeno[1,2-b]anthracene (9 g, 0.0241 mol) and biphenyl-4-ylboronic acid (7.12 g, 0.036 mol) were added.

GC-Mass(FAB): (theoretical value: 446.58 g/mol, measured value: 446 g/mol)

Synthesis Example 41

Preparation of 11-(biphenyl-4-yl)-6-bromo-13,13-dimethyl-13H-indeno[1,2-b]anthracene 11-(biphenyl-4-yl)-6-bromo-13,13-dimethyl-13H-indeno[1,2-b]anthracene (6.3 g, yield=71%) was obtained in the same manner as in Synthesis Example 35 except that 11-(biphenyl-4-yl)-13,13-dimethyl-13H-indeno[1,2-b]anthracene (7.59 g, 0.017 mol) was added.

GC-Mass(FAB): (theoretical value: 525.48 g/mol, measured value: 525 g/mol)

Example 106

Preparation of Inv-155

11-(biphenyl-4-yl)-6-bromo-13,13-dimethyl-13H-indeno[1,2-b]anthracene (5.78 g, 0.011 mol) and 4-(1-phenyl-1H-benzo[d]imidazol-2-yl)phenylboronic acid (3.5 g, 0.011 mol) were dissolved in toluene (200 ml). Then, synthesis was carried out in the same manner as in Example 1 to give Inv-155 (5.7 g, yield=73%).

GC-Mass(FAB): (theoretical value: 714.89 g/mol, measured value: 714 g/mol)

Example 107

Preparation of Inv-174

11-(biphenyl-4-yl)-6-bromo-13,13-dimethyl-13H-indeno[1,2-b]anthracene (5.47 g, 0.011 mol) and 3-(1-phenyl-1H-benzo[d]imidazol-2-yl)phenylboronic acid (3.5 g, 0.011 mol) were dissolved in toluene (200 ml). Then, synthesis was carried out in the same manner as in Example 1 to give Inv-174 (5.5 g, yield=70%).

GC-Mass(FAB): (theoretical value: 714.89 g/mol, measured value: 714 g/mol)

Example 108

Preparation of Inv-184

11-(biphenyl-4-yl)-6-bromo-13,13-dimethyl-13H-indeno[1,2-b]anthracene (5.47 g, 0.011 mol) and benzo[d]oxazol-2-ylboronic acid (1.79 g, 0.011 mol) were dissolved in toluene (200 ml). Then, synthesis was carried out in the same manner as in Example 1 to give Inv-184 (3.9 g, yield=63%).

GC-Mass(FAB): (theoretical value: 563.69 g/mol, measured value: 563 g/mol)

Example 109

Preparation of Inv-194

11-(biphenyl-4-yl)-6-bromo-13,13-dimethyl-13H-indeno[1,2-b]anthracene (5.47 g, 0.011 mol) and benzo[d]thiazol-2-ylboronic acid (1.97 g, 0.011 mol) were dissolved in toluene (200 ml). Then, synthesis was carried out in the same manner as in Example 1 to give Inv-194 (4.2 g, yield=66%).

GC-Mass(FAB): (theoretical value: 579.75 g/mol, measured value: 579 g/mol)

Example 110

Preparation of Inv-204

11-(biphenyl-4-yl)-6-bromo-13,13-dimethyl-13H-indeno[1,2-b]anthracene (5.47 g, 0.011 mol) and 4-(benzo[d]oxazol-2-yl)phenylboronic acid (2.63 g, 0.011 mol) were dissolved in toluene (200 ml). Then, synthesis was carried out in the same manner as in Example 1 to give Inv-204 (5.8 g, yield=83%).

GC-Mass(FAB): (theoretical value: 639.78 g/mol, measured value: 639 g/mol)

Example 111

Preparation of Inv-214

11-(biphenyl-4-yl)-6-bromo-13,13-dimethyl-13H-indeno[1,2-b]anthracene (5.47 g, 0.011 mol) and 4-(benzo[d]thiazol-2-yl)phenylboronic acid (2.80 g, 0.011 mol) were dissolved in toluene (200 ml). Then, synthesis was carried out in the same manner as in Example 1 to give Inv-214 (4.4 g, yield=61%).

GC-Mass(FAB): (theoretical value: 655.85 g/mol, measured value: 655 g/mol)

Example 112

Preparation of Inv-224

11-(biphenyl-4-yl)-6-bromo-13,13-dimethyl-13H-indeno[1,2-b]anthracene (5.47 g, 0.011 mol) and 5-(4,4,5,5-tetramethyl-1,3,2-dioxaborolan-2-yl)-2,2'-bipyridine (3.10 g, 0.011 mol) were dissolved in toluene (200 ml). Then, synthesis was carried out in the same manner as in Example 1 to give Inv-224 (4.1 g, yield=62%).

GC-Mass(FAB): (theoretical value: 600.75 g/mol, measured value: 600 g/mol)

Synthesis Example 42

Preparation of 11-(biphenyl-3-yl)-13,13-dimethyl-13H-indeno[1,2-b]anthracene 11-(biphenyl-3-yl)-13,13-dimethyl-13H-indeno[1,2-b]anthracene (7.0 g, yield=65%) was obtained in the same manner as in Synthesis Example 34 except that 11-bromo-13,13-dimethyl-13H-indeno[1,2-b]anthracene (9 g, 0.0241 mol) and biphenyl-3-ylboronic acid (7.12 g, 0.036 mol) were added.

GC-Mass(FAB): (theoretical value: 446.58 g/mol, measured value: 446 g/mol)

Synthesis Example 43

Preparation of 11-(biphenyl-3-yl)-6-bromo-13,13-dimethyl-13H-indeno[1,2-b]anthracene 11-(biphenyl-3-yl)-6-bromo-13,13-dimethyl-13H-indeno[1,2-b]anthracene (5.4 g, yield=60%) was obtained in the same manner as in Synthesis Example 35 except that 11-(biphenyl-3-yl)-13,13-dimethyl-13H-indeno[1,2-b]anthracene (7.59 g, 0.017 mol) was added.

GC-Mass(FAB): (theoretical value: 525.48 g/mol, measured value: 525 g/mol)

Example 113

Preparation of Inv-156

11-(biphenyl-3-yl)-6-bromo-13,13-dimethyl-13H-indeno[1,2-b]anthracene (5.78 g, 0.011 mol) and 4-(1-phenyl-1H-benzo[d]imidazol-2-yl)phenylboronic acid (3.5 g, 0.011 mol) were dissolved in toluene (200 ml). Then, synthesis was carried out in the same manner as in Example 1 to give Inv-156 (5.4 g, yield=69%).

GC-Mass(FAB): (theoretical value: 714.89 g/mol, measured value: 714 g/mol)

Example 114

Preparation of Inv-175

11-(biphenyl-3-yl)-6-bromo-13,13-dimethyl-13H-indeno[1,2-b]anthracene (5.47 g, 0.011 mol) and 3-(1-phenyl-1H-benzo[d]imidazol-2-yl)phenylboronic acid (3.5 g, 0.011 mol) were dissolved in toluene (200 ml). Then, synthesis was carried out in the same manner as in Example 1 to give Inv-175 (5.8 g, yield=74%).

GC-Mass(FAB): (theoretical value: 714.89 g/mol, measured value: 714 g/mol)

Example 115

Preparation of Inv-185

11-(biphenyl-3-yl)-6-bromo-13,13-dimethyl-13H-indeno[1,2-b]anthracene (5.47 g, 0.011 mol) and benzo[d]oxazol-2-ylboronic acid (1.79 g, 0.011 mol) were dissolved in toluene (200 ml). Then, synthesis was carried out in the same manner as in Example 1 to give Inv-185 (3.7 g, yield=60%).

GC-Mass(FAB): (theoretical value: 563.69 g/mol, measured value: 563 g/mol)

Example 116

Preparation of Inv-195

11-(biphenyl-3-yl)-6-bromo-13,13-dimethyl-13H-indeno[1,2-b]anthracene (5.47 g, 0.011 mol) and benzo[d]thiazol-2-ylboronic acid (1.97 g, 0.011 mol) were dissolved in toluene (200 ml). Then, synthesis was carried out in the same manner as in Example 1 to give Inv-195 (4.6 g, yield=72%).

GC-Mass(FAB): (theoretical value: 579.75 g/mol, measured value: 579 g/mol)

Example 117

Preparation of Inv-205

11-(biphenyl-3-yl)-6-bromo-13,13-dimethyl-13H-indeno[1,2-b]anthracene (5.47 g, 0.011 mol) and 4-(benzo[d]oxazol-2-yl)phenylboronic acid (2.63 g, 0.011 mol) were dissolved in toluene (200 ml). Then, synthesis was carried out in the same manner as in Example 1 to give Inv-205 (5.7 g, yield=80%).

GC-Mass(FAB): (theoretical value: 639.78 g/mol, measured value: 639 g/mol)

Example 118

Preparation of Inv-215

11-(biphenyl-3-yl)-6-bromo-13,13-dimethyl-13H-indeno[1,2-b]anthracene (5.47 g, 0.011 mol) and 4-(benzo[d]thiazol-2-yl)phenylboronic acid (2.80 g, 0.011 mol) were dissolved in toluene (200 ml). Then, synthesis was carried out in the same manner as in Example 1 to give Inv-215 (5.1 g, yield=70%).

GC-Mass(FAB): (theoretical value: 655.85 g/mol, measured value: 655 g/mol)

Example 119

Preparation of Inv-225

11-(biphenyl-3-yl)-6-bromo-13,13-dimethyl-13H-indeno[1,2-b]anthracene (5.47 g, 0.011 mol) and 5-(4,4,5,5-tetramethyl-1,3,2-dioxaborolan-2-yl)-2,2'-bipyridine (3.10 g, 0.011 mol) were dissolved in toluene (200 ml). Then, synthesis was carried out in the same manner as in Example 1 to give Inv-225 (5.1 g, yield=77%).

GC-Mass(FAB): (theoretical value: 600.75 g/mol, measured value: 600 g/mol)

Synthesis Example 44

Preparation of 11-(9,9-dimethyl-9H-fluoren-2-yl)-13,13-dimethyl-13H-indeno[1,2-b]anthracene 11-(9,9-dimethyl-9H-fluoren-2-yl)-13,13-dimethyl-13H-indeno[1,2-b]anthracene (8.2 g, yield=69%) was obtained in the same manner as in Synthesis Example 34 except that 11-bromo-13,13-dimethyl-13H-indeno[1,2-b]anthracene (9 g, 0.0241 mol) and 9,9-dimethyl-9H-fluoren-2-ylboronic acid (8.57 g, 0.036 mol) were added.

GC-Mass(FAB): (theoretical value: 486.64 g/mol, measured value: 486 g/mol)

Synthesis Example 45

Preparation of 6-bromo-11-(9,9-dimethyl-9H-fluoren-2-yl)-13,13-dimethyl-13H-indeno[1,2-b]anthracene 6-bromo-11-(9,9-dimethyl-9H-fluoren-2-yl)-13,13-dimethyl-13H-indeno[1,2-b]anthracene (7.2 g, yield=75%) was obtained in the same manner as in Synthesis Example 35 except that 11-(9,9-dimethyl-9H-fluoren-2-yl)-13,13-dimethyl-13H-indeno[1,2-b]anthracene (8.27 g, 0.017 mol) was added.

GC-Mass(FAB): (theoretical value: 565.54 g/mol, measured value: 565 g/mol)

Example 120

Preparation of Inv-158

6-bromo-11-(9,9-dimethyl-9H-fluoren-2-yl)-13,13-dimethyl-13H-indeno[1,2-b]anthracene (6.22 g, 0.011 mol) and 4-(1-phenyl-1H-benzo[d]imidazol-2-yl)phenylboronic acid (3.5 g, 0.011 mol) were dissolved in toluene (200 ml). Then, synthesis was carried out in the same manner as in Example 1 to give Inv-158 (6.2 g, yield=75%).

GC-Mass(FAB): (theoretical value: 754.96 g/mol, measured value: 754 g/mol)

Example 121

Preparation of Inv-177

6-bromo-11-(9,9-dimethyl-9H-fluoren-2-yl)-13,13-dimethyl-13H-indeno[1,2-b]anthracene (6.22 g, 0.011 mol) and 3-(1-phenyl-1H-benzo[d]imidazol-2-yl)phenylboronic acid (3.5 g, 0.011 mol) were dissolved in toluene (200 ml). Then, synthesis was carried out in the same manner as in Example 1 to give Inv-177 (6.4 g, yield=77%).

GC-Mass(FAB): (theoretical value: 754.96 g/mol, measured value: 754 g/mol)

Example 122

Preparation of Inv-187

6-bromo-11-(9,9-dimethyl-9H-fluoren-2-yl)-13,13-dimethyl-13H-indeno[1,2-b]anthracene (6.22 g, 0.011 mol) and benzo[d]oxazol-2-ylboronic acid (1.79 g, 0.011 mol) were dissolved in toluene (200 ml). Then, synthesis was carried out in the same manner as in Example 1 to give Inv-187 (4.5 g, yield=68%).

GC-Mass(FAB): (theoretical value: 603.73 g/mol, measured value: 603 g/mol)

Example 123

Preparation of Inv-197

6-bromo-11-(9,9-dimethyl-9H-fluoren-2-yl)-13,13-dimethyl-13H-indeno[1,2-b]anthracene (6.22 g, 0.011 mol) and benzo[d]thiazol-2-ylboronic acid (1.97 g, 0.011 mol) were dissolved in toluene (200 ml). Then, synthesis was carried out in the same manner as in Example 1 to give Inv-197 (4.3 g, yield=63%).

GC-Mass(FAB): (theoretical value: 619.82 g/mol, measured value: 619 g/mol)

Example 124

Preparation of Inv-207

6-bromo-11-(9,9-dimethyl-9H-fluoren-2-yl)-13,13-dimethyl-13H-indeno[1,2-b]anthracene (6.22 g, 0.011 mol) and 4-(benzo[d]oxazol-2-yl)phenylboronic acid (2.63 g, 0.011 mol) were dissolved in toluene (200 ml). Then, synthesis was carried out in the same manner as in Example 1 to give Inv-207 (5.3 g, yield=71%).

GC-Mass(FAB): (theoretical value: 679.85 g/mol, measured value: 679 g/mol)

Example 125

Preparation of Inv-217

6-bromo-11-(9,9-dimethyl-9H-fluoren-2-yl)-13,13-dimethyl-13H-indeno[1,2-b]anthracene (6.22 g, 0.011 mol) and 4-(benzo[d]thiazol-2-yl)phenylboronic acid (2.80 g, 0.011 mol) were dissolved in toluene (200 ml). Then, synthesis was carried out in the same manner as in Example 1 to give Inv-217 (5.8 g, yield=76%).

GC-Mass(FAB): (theoretical value: 695.91 g/mol, measured value: 695 g/mol)

Example 126

Preparation of Inv-227

6-bromo-11-(9,9-dimethyl-9H-fluoren-2-yl)-13,13-dimethyl-13H-indeno[1,2-b]anthracene (6.22 g, 0.011 mol) and 5-(4,4,5,5-tetramethyl-1,3,2-dioxaborolan-2-yl)-2,2'-bipyridine (3.10 g, 0.011 mol) were dissolved in toluene (200 ml). Then, synthesis was carried out in the same manner as in Example 1 to give Inv-227 (5.3 g, yield=75%).

GC-Mass(FAB): (theoretical value: 640.81 g/mol, measured value: 640 g/mol)

Synthesis Example 46

Preparation of 2-(4-(13,13-dimethyl-13H-indeno[1,2-b]anthracen-11-yl)phenyl)-1-phenyl-1H-benzo[d]imidazole 2-(4-(13,13-dimethyl-13H-indeno[1,2-b]anthracen-11-yl)phenyl)-1-phenyl-1H-benzo[d]imidazole (5.5 g, yield=75%) was obtained in the same manner as in Synthesis Example 34 except that 11-bromo-13,13-dimethyl-13H-indeno[1,2-b]anthracene (5 g, 0.013 mol) and 4-(1-phenyl-1H-benzo[d]imidazol-2-yl)phenylboronic acid (4.08 g, 0.013 mol) were added.

GC-Mass(FAB): (theoretical value: 562.70 g/mol, measured value: 562 g/mol)

Synthesis Example 47

Preparation of 2-(4-(6-bromo-13,13-dimethyl-13H-indeno[1,2-b]anthracen-11-yl)phenyl)-1-phenyl-1H-benzo[d]imidazole 2-(4-(6-bromo-13,13-dimethyl-13H-indeno[1,2-b]anthracen-11-yl)phenyl)-1-phenyl-1H-benzo[d]Imidazole (4.6 g, yield=82%) was obtained in the same manner as in Synthesis Example except that 2-(4-(13,13-dimethyl-13H-indeno[1,2-b]anthracen-11-yl)phenyl)-1-phenyl-1H-benzo[d]imidazole (5 g, 0.0088 mol) was added.

GC-Mass(FAB): (theoretical value: 641.60 g/mol, measured value: 641 g/mol)

Example 127

Preparation of Inv-142

2-(4-(6-bromo-13,13-dimethyl-13H-indeno[1,2-b]anthracen-11-yl)phenyl)-1-phenyl-1H-benzo[d]Imidazole (5 g, 0.0078 mol) and Phenylboronic acid (0.95 g, 0.0078 mol) were dissolved in toluene (150 ml). Then, synthesis was carried out in the same manner as in Example 1 to give Inv-142 (3.2 g, yield=64%).

GC-Mass(FAB): (theoretical value: 638.80 g/mol, measured value: 638 g/mol)

Example 128

Preparation of Inv-143

2-(4-(6-bromo-13,13-dimethyl-13H-indeno[1,2-b]anthracen-11-yl)phenyl)-1-phenyl-1H-benzo[d]Imidazole (5 g, 0.0078 mol) and naphthalen-2-ylboronic acid (1.34 g, 0.0078 mol) were dissolved in toluene (150 ml). Then, synthesis was carried out in the same manner as in Example 1 to give Inv-143 (3.2 g, yield=65%).

GC-Mass(FAB): (theoretical value: 688.86 g/mol, measured value: 688 g/mol)

Example 129

Preparation of Inv-144

2-(4-(6-bromo-13,13-dimethyl-13H-indeno[1,2-b]anthracen-11-yl)phenyl)-1-phenyl-1H-benzo[d]Imidazole (5 g, 0.0078 mol) and naphthalen-1-ylboronic acid (1.34 g, 0.0078 mol) were dissolved in toluene (150 ml). Then, synthesis was carried out in the same manner as in Example 1 to give Inv-144 (2.9 g, yield=54%).

GC-Mass(FAB): (theoretical value: 688.86 g/mol, measured value: 688 g/mol)

Example 130

Preparation of Inv-145

2-(4-(6-bromo-13,13-dimethyl-13H-indeno[1,2-b]anthracen-11-yl)phenyl)-1-phenyl-1H-benzo[d]Imidazole (5 g, 0.0078 mol) and biphenyl-4-ylboronic acid (1.54 g, 0.0078 mol) were dissolved in toluene (150 ml). Then, synthesis was carried out in the same manner as in Example 1 to give Inv-145 (3.0 g, yield=54%).

GC-Mass(FAB): (theoretical value: 714.89 g/mol, measured value: 714 g/mol)

Example 131

Preparation of Inv-146

2-(4-(6-bromo-13,13-dimethyl-13H-indeno[1,2-b]anthracen-11-yl)phenyl)-1-phenyl-1H-benzo[d]Imidazole (5 g, 0.0078 mol) and biphenyl-3-ylboronic acid (1.54 g, 0.0078 mol) were dissolved in toluene (150 ml). Then, synthesis was carried out in the same manner as in Example 1 to give Inv-146 (3.2 g, yield=57%).

GC-Mass(FAB): (theoretical value: 714.89 g/mol, measured value: 714 g/mol)

Example 132

Preparation of Inv-147

2-(4-(6-bromo-13,13-dimethyl-13H-indeno[1,2-b]anthracen-11-yl)phenyl)-1-phenyl-1H-benzo[d]Imidazole (5 g, 0.0078 mol) and biphenyl-2-ylboronic acid (1.54 g, 0.0078 mol) were dissolved in toluene (150 ml). Then, synthesis was carried out in the same manner as in Example 1 to give Inv-147 (2.8 g, yield=50%).

GC-Mass(FAB): (theoretical value: 714.89 g/mol, measured value: 714 g/mol)

Example 133

Preparation of Inv-148

2-(4-(6-bromo-13,13-dimethyl-13H-indeno[1,2-b]anthracen-11-yl)phenyl)-1-phenyl-1H-benzo[d]Imidazole (5 g, 0.0078 mol) and 9,9-dimethyl-9H-fluoren-2-ylboronic acid (1.85 g, 0.0078 mol) were dissolved in toluene (150 ml). Then, synthesis was carried out in the same manner as in Example 1 to give Inv-148 (3.1 g, yield=53%).

GC-Mass(FAB): (theoretical value: 754.96 g/mol, measured value: 754 g/mol)

Example 134

Preparation of Inv-149

2-(4-(6-bromo-13,13-dimethyl-13H-indeno[1,2-b]anthracen-11-yl)phenyl)-1-phenyl-1H-benzo[d]Imidazole (5 g, 0.0078 mol) and phenanthren-9-ylboronic acid (1.73 g, 0.0078 mol) were dissolved in toluene (150 ml). Then, synthesis was carried out in the same manner as in Example 1 to give Inv-149 (3.3 g, yield=57%).

GC-Mass(FAB): (theoretical value: 738.91 g/mol, measured value: 738 g/mol)

Example 135

Preparation of Inv-150

2-(4-(6-bromo-13,13-dimethyl-13H-indeno[1,2-b]anthracen-11-yl)phenyl)-1-phenyl-1H-benzo[d]Imidazole (5 g, 0.0078 mol) and fluoranthen-3-ylboronic acid (1.92 g, 0.0078 mol) were dissolved in toluene (150 ml). Then, synthesis was carried out in the same manner as in Example 1 to give Inv-150 (4.1 g, yield=69%).

GC-Mass(FAB): (theoretical value: 762.94 g/mol, measured value: 762 g/mol)

Synthesis Example 48

Preparation of 2-(3-(13,13-dimethyl-13H-indeno[1,2-b]anthracen-11-yl)phenyl)-1-phenyl-1H-benzo[d]imidazole 2-(3-(13,13-dimethyl-13H-indeno[1,2-b]anthracen-11-yl)phenyl)-1-phenyl-1H-benzo[d]imidazole (5.6 g, yield=77%) was obtained in the same manner as in Synthesis Example 34 except that 11-bromo-13,13-dimethyl-13H-indeno[1,2-b]anthracene (5 g, 0.013 mol) and 3-(1-phenyl-1H-benzo[d]imidazol-2-yl)phenylboronic acid (4.08 g, 0.013 mol) were added.

GC-Mass(FAB): (theoretical value: 562.70 g/mol, measured value: 562 g/mol)

Synthesis Example 49

Preparation of 2-(3-(6-bromo-13,13-dimethyl-13H-indeno[1,2-b]anthracen-11-yl)phenyl)-1-phenyl-1H-benzo[d]imidazole 2-(3-(6-bromo-13,13-dimethyl-13H-indeno[1,2-b]anthracen-11-yl)phenyl)-1-phenyl-1H-benzo[d]imidazole (4.8 g, yield=85%) was obtained in the same manner as in Synthesis Example except that 2-(3-(13,13-dimethyl-13H-indeno[1,2-b]anthracen-11-yl)phenyl)-1-phenyl-1H-benzo[d]imidazole (5 g, 0.0088 mol) was added.

GC-Mass(FAB): (theoretical value: 641.60 g/mol, measured value: 641 g/mol)

Example 136

Preparation of Inv-162

2-(3-(6-bromo-13,13-dimethyl-13H-indeno[1,2-b]anthracen-11-yl)phenyl)-1-phenyl-1H-benzo[d]imidazole (5 g, 0.0078 mol) and Phenylboronic acid (0.95 g, 0.0078 mol) were dissolved in toluene (150 ml). Then, synthesis was carried out in the same manner as in Example 1 to give Inv-162 (3.5 g, yield=70%).

GC-Mass(FAB): (theoretical value: 638.80 g/mol, measured value: 638 g/mol)

Example 137

Preparation of Inv-163

2-(3-(6-bromo-13,13-dimethyl-13H-indeno[1,2-b]anthracen-11-yl)phenyl)-1-phenyl-1H-benzo[d]imidazole (5 g, 0.0078 mol) and naphthalen-2-ylboronic acid (1.34 g, 0.0078 mol) were dissolved in toluene (150 ml). Then, synthesis was carried out in the same manner as in Example 1 to give Inv-163 (2.9 g, yield=54%).

GC-Mass(FAB): (theoretical value: 688.86 g/mol, measured value: 688 g/mol)

Example 138

Preparation of Inv-164

2-(3-(6-bromo-13,13-dimethyl-13H-indeno[1,2-b]anthracen-11-yl)phenyl)-1-phenyl-1H-benzo[d]imidazole (5 g, 0.0078 mol) and naphthalen-1-ylboronic acid (1.34 g, 0.0078 mol) were dissolved in toluene (150 ml). Then, synthesis was carried out in the same manner as in Example 1 to give Inv-164 (2.7 g, yield=50%).

GC-Mass(FAB): (theoretical value: 688.86 g/mol, measured value: 688 g/mol)

Example 139

Preparation of Inv-165

2-(3-(6-bromo-13,13-dimethyl-13H-indeno[1,2-b]anthracen-11-yl)phenyl)-1-phenyl-1H-benzo[d]imidazole (5 g, 0.0078 mol) and biphenyl-4-ylboronic acid (1.54 g, 0.0078 mol) were dissolved in toluene (150 ml). Then, synthesis was carried out in the same manner as in Example 1 to give Inv-165 (3.5 g, yield=63%).

GC-Mass(FAB): (theoretical value: 714.89 g/mol, measured value: 714 g/mol)

Example 140

Preparation of Inv-166

2-(3-(6-bromo-13,13-dimethyl-13H-indeno[1,2-b]anthracen-11-yl)phenyl)-1-phenyl-1H-benzo[d]imidazole (5 g, 0.0078 mol) and biphenyl-3-ylboronic acid (1.54 g, 0.0078 mol) were dissolved in toluene (150 ml). Then, synthesis was carried out in the same manner as in Example 1 to give Inv-166 (3.3 g, yield=60%).

GC-Mass(FAB): (theoretical value: 714.89 g/mol, measured value: 714 g/mol)

Example 141

Preparation of Inv-167

2-(3-(6-bromo-13,13-dimethyl-13H-indeno[1,2-b]anthracen-11-yl)phenyl)-1-phenyl-1H-benzo[d]imidazole (5 g, 0.0078 mol) and 9,9-dimethyl-9H-fluoren-2-ylboronic acid (1.85 g, 0.0078 mol) were dissolved in toluene (150 ml). Then, synthesis was carried out in the same manner as in Example 1 to give Inv-167 (3.2 g, yield=54%).

GC-Mass(FAB): (theoretical value: 754.96 g/mol, measured value: 754 g/mol)

Example 142

Preparation of Inv-168

2-(3-(6-bromo-13,13-dimethyl-13H-indeno[1,2-b]anthracen-11-yl)phenyl)-1-phenyl-1H-benzo[d]imidazole (5 g, 0.0078 mol) and phenanthren-9-ylboronic acid (1.73 g, 0.0078 mol) were dissolved in toluene (150 ml). Then, synthesis was carried out in the same manner as in Example 1 to give Inv-168 (3.1 g, yield=54%).

GC-Mass(FAB): (theoretical value: 738.91 g/mol, measured value: 738 g/mol)

Example 143

Preparation of Inv-169

2-(3-(6-bromo-13,13-dimethyl-13H-indeno[1,2-b]anthracen-11-yl)phenyl)-1-phenyl-1H-benzo[d]imidazole (5 g, 0.0078 mol) and fluoranthen-3-ylboronic acid (1.92 g, 0.0078 mol) were dissolved in toluene (150 ml). Then, synthesis was carried out in the same manner as in Example 1 to give Inv-169 (4.5 g, yield=76%).

GC-Mass(FAB): (theoretical value: 762.94 g/mol, measured value: 762 g/mol)

Synthesis Example 50

Preparation of 6,11-dibromo-13,13-dimethyl-13H-indeno[1,2-b]anthracene 13,13-dimethyl-13H-indeno[1,2-b]anthracene (5 g, 0.017 mol) and N-bromosuccinimide (7.68 g, 0.034 mol) were dissolved in carbon tetrachloride (150 ml), and the reaction mixture was stirred under reflux for 5 hours at 60° C. After the reaction was terminated, the reaction solution was extracted with distilled water, and purified by column chromatography to give 6,11-dibromo-13,13-dimethyl-13H-indeno[1,2-b]anthracene (6.1 g, yield=79%).

GC-Mass(FAB): (theoretical value: 452.18 g/mol, measured value: 452 g/mol)

Example 144

Preparation of Inv-242

6,11-dibromo-13,13-dimethyl-13H-indeno[1,2-b]anthracene (5 g, 0.011 mol) and 1-phenyl-1H-benzo[d]imidazol-2-ylboronic acid (5.23 g, 0.022 mol) were dissolved in toluene (150 ml). Then, synthesis was carried out in the same manner as in Example 1 to give Inv-242 (5.6 g, yield=75%).

GC-Mass(FAB): (theoretical value: 678.82 g/mol, measured value: 678 g/mol)

Example 145

Preparation of Inv-243

6,11-dibromo-13,13-dimethyl-13H-indeno[1,2-b]anthracene (5 g, 0.011 mol) and 4-(1-phenyl-1H-benzo[d]imidazol-2-yl)phenylboronic acid (6.91 g, 0.022 mol) were dissolved in toluene (150 ml). Then, synthesis was carried out in the same manner as in Example 1 to give Inv-243 (7.2 g, yield=78%).

GC-Mass(FAB): (theoretical value: 831.01 g/mol, measured value: 830 g/mol)

Example 146

Preparation of Inv-248

6,11-dibromo-13,13-dimethyl-13H-indeno[1,2-b]anthracene (5 g, 0.011 mol) and 3-(1-phenyl-1H-benzo[d]imidazol-2-yl)phenylboronic acid (6.91, 0.022 mol) were dissolved in toluene (150 ml). Then, synthesis was carried out in the same manner as in Example 1 to give Inv-248 (6.7 g, yield=73%).

GC-Mass(FAB): (theoretical value: 831.01 g/mol, measured value: 830 g/mol)

Example 147

Preparation of Inv-251

6,11-dibromo-13,13-dimethyl-13H-indeno[1,2-b]anthracene (5 g, 0.011 mol) and 5-(4,4,5,5-tetramethyl-1,3,2-dioxaborolan-2-yl)-2,2'-bipyridine (6.02 g, 0.022 mol) were dissolved in toluene (150 ml). Then, synthesis was carried out in the same manner as in Example 1 to give Inv-251 (4.3 g, yield=65%).

GC-Mass(FAB): (theoretical value: 602.73 g/mol, measured value: 602 g/mol)

Example 148

Preparation of Inv-252

6,11-dibromo-13,13-dimethyl-13H-indeno[1,2-b]anthracene (5 g, 0.011 mol) and benzo[d]oxazol-2-ylboronic acid (3.58 g, 0.022 mol) were dissolved in toluene (150 ml). Then, synthesis was carried out in the same manner as in Example 1 to give Inv-252 (3.1 g, yield=53%).

GC-Mass(FAB): (theoretical value: 528.60 g/mol, measured value: 528 g/mol)

Example 149

Preparation of Inv-258

6,11-dibromo-13,13-dimethyl-13H-indeno[1,2-b]anthracene (5 g, 0.011 mol) and 4-(benzo[d]oxazol-2-yl)phenylboronic acid (5.25 g, 0.022 mol) were dissolved in toluene (150 ml). Then, synthesis was carried out in the same manner as in Example 1 to give Inv-258 (6.0 g, yield=80%).

GC-Mass(FAB): (theoretical value: 680.79 g/mol, measured value: 680 g/mol)

Example 150

Preparation of Inv-259

6,11-dibromo-13,13-dimethyl-13H-indeno[1,2-b]anthracene (5 g, 0.011 mol) and 4-(benzo[d]thiazol-2-yl)phenylboronic acid (5.61, 0.022 mol) were dissolved in toluene (150 ml). Then, synthesis was carried out in the same manner as in Example 1 to give Inv-259 (5.4 g, yield=69%).

GC-Mass(FAB): (theoretical value: 712.92 g/mol, measured value: 712 g/mol)

Synthesis Example 51

Preparation of 2-(5-bromo-9,9-dimethyl-9H-fluorene-2-carbonyl)benzoic acid 2-(5-bromo-9,9-dimethyl-9H-fluorene-2-carbonyl)benzoic acid (51 g, yield=83%) was obtained in the same manner as in Synthesis Example 2 except that 4-bromo-9,9-dimethyl-9H-fluorene (40 g, 0.146 mol) was added.

GC-Mass(FAB): (theoretical value: 421.28 g/mol, measured value: 421 g/mol)

Synthesis Example 52

Preparation of 4-bromo-13,13-dimethyl-13H-indeno[1,2-b]anthracene-6,11-dione 4-bromo-13,13-dimethyl-13H-indeno[1,2-b]anthracene-6,11-dione (15 g, yield=58%) was obtained in the same manner as in Synthesis Example 3 except that 2-(5-bromo-9,9-dimethyl-9H-fluorene-2-carbonyl)benzoic acid (20 g, 0.061 mol) was added.

GC-Mass(FAB): (theoretical value: 403.27 g/mol, measured value: 403 g/mol)

Synthesis Example 53

Preparation of 4-bromo-13,13-dimethyl-6,11-diphenyl-11,13-dihydro-6H-indeno[1,2-b]anthracene-6,11-diol 4-bromo-13,13-dimethyl-6,11-diphenyl-11,13-dihydro-6H-indeno[1,2-b]anthracene-6,11-diol (8 g, yield=60%) was obtained in the same manner as in Synthesis Example 4 except that 4-bromo-13,13-dimethyl-13H-indeno[1,2-b]anthracene-6,11-dione (10 g, 0.024 mol) was added.

GC-Mass(FAB): (theoretical value: 559.49 g/mol, measured value: 559 g/mol)

Synthesis Example 54

Preparation of 4-bromo-13,13-dimethyl-6,11-diphenyl-13H-indeno[1,2-b]anthracene 4-bromo-13,13-dimethyl-6,11-diphenyl-13H-indeno[1,2-b]anthracene (2.5 g, yield=65%) was obtained in the same manner as in Synthesis Example 5 except that 4-bromo-13,13-dimethyl-6,11-diphenyl-11,13-dihydro-6H-indeno[1,2-b]anthracene-6,11-diol (4.19 g, 0.0075 mol) was added.

GC-Mass(FAB): (theoretical value: 525.48 g/mol, measured value: 525 g/mol)

Example 151

Preparation of Inv-276

4-bromo-13,13-dimethyl-6,11-diphenyl-13H-indeno[1,2-b]anthracene (5 g, 0.0095 mol) and 4-(1-phenyl-1H-benzo[d]imidazol-2-yl)phenylboronic acid (2.98 g, 0.0095 mol) were dissolved in toluene (150 ml). Then, synthesis was carried out in the same manner as in Example 1 to give Inv-276 (3.5 g, yield=52%).

GC-Mass(FAB): (theoretical value: 714.89 g/mol, measured value: 714 g/mol)

ExampleS 152 TO 187, AND COMPARATIVE EXAMPLE 1

Fabrication of an Organic Electroluminescent Device

A glass substrate coated with ITO (Indium tin oxide) (coating thickness: 1500 Å) was ultrasonically washed with distilled water and then with a solvent (such as isopropyl alcohol, acetone, methanol etc.), and dried. Then, the glass substrate was transported to a plasma cleaner, cleaned with oxygen plasma for five minutes and transported to a vacuum deposition machine.

On the ITO transparent electrode as fabricated above, DS-HIL (Doosan Corp.) was deposited under a thermal vacuum to a thickness of 600 Å so as to form a hole injection layer, and a hole transport material, NPB (N,N-di(naphthalene-1-yl)-N, N-diphenylbenzidine) was deposited to a thickness of 150 Å on the hole injection layer to form a hole transport layer. Next, ADN (9,10-di(naphthalen-2-yl)anthracene) performing a role of a light emitting layer, as a host, and DS-405 (Doosan Corp.) as a dopant were deposited thereto with a thickness of 300□ so as to form a light emitting layer.

On the light emitting layer, as an electron injection/transport material, Inv-10 (Example 152), Inv-11 (Example 153), Inv-12 (Example 154), Inv-13 (Example 155), Inv-19 (Example 156), Inv-20 (Example 157), Inv-21 (Example 158), Inv-22 (Example 159), Inv-62 (Example 160), Inv-63 (Example 161), Inv-80 (Example 162), Inv-81 (Example 163), Inv-82 (Example 164), Inv-83 (Example 165), Inv-89 (Example 166), Inv-90 (Example 167), Inv-91 (Example 168), Inv-92 (Example 169), Inv-152 (Example 170), Inv-153 (Example 171), Inv-154 (Example 172), Inv-155 (Example 173), Inv-171 (Example 174), Inv-172 (Example 175), Inv-173 (Example 176), Inv-174 (Example 177), Inv-175 (Example 178), Inv-221 (Example 179), Inv-222 (Example 180), Inv-223 (Example 181), Inv-224 (Example 182), Inv-225 (Example 183), Inv-243 (Example 184), Inv-248 (Example 185), Inv-251 (Example 186), Inv-276 (Example 187) or Alq3 (aluminum tris(8-hydroxyquinoline)) (a control material, Comparative Example 1) was deposited with a thickness of 250□ so as to form electron injection layer and electron transport layer. On the electron injection layer and electron transport layer, sequentially, LiF was deposited to a thickness of 10 Å, and Al was deposited to a thickness of 2000 Å, so as to form an electron injection layer, and a cathode, respectively. Through this process, the device was fabricated.

The characteristics of each of the fabricated organic electroluminescent devices are noted in Table 1.

TABLE 1

| | voltage (V) | luminance (cd/m$^2$) | efficiency (cd/A) |
|---|---|---|---|
| Exp. 152 | 5.4 | 612 | 6.1 |
| Exp. 153 | 5.5 | 620 | 6.2 |
| Exp. 154 | 5.5 | 618 | 6.2 |
| Exp. 155 | 5.3 | 631 | 6.3 |
| Exp. 156 | 5.3 | 617 | 6.2 |
| Exp. 157 | 5.2 | 623 | 6.2 |
| Exp. 158 | 5.2 | 620 | 6.2 |
| Exp. 159 | 5.3 | 633 | 6.3 |
| Exp. 160 | 5.3 | 628 | 6.3 |
| Exp. 161 | 5.1 | 618 | 6.2 |
| Exp. 162 | 5.2 | 620 | 6.2 |
| Exp. 163 | 5.1 | 638 | 6.4 |
| Exp. 164 | 5.2 | 623 | 6.2 |
| Exp. 165 | 5.2 | 634 | 6.3 |
| Exp. 166 | 5.1 | 620 | 6.2 |
| Exp. 167 | 5.2 | 632 | 6.3 |
| Exp. 168 | 5.2 | 631 | 6.3 |
| Exp. 169 | 5.1 | 628 | 6.3 |
| Exp. 170 | 4.8 | 663 | 6.6 |
| Exp. 171 | 4.7 | 667 | 6.7 |
| Exp. 172 | 4.8 | 666 | 6.7 |
| Exp. 173 | 4.7 | 671 | 6.7 |
| Exp. 174 | 4.8 | 661 | 6.6 |
| Exp. 175 | 4.7 | 669 | 6.7 |
| Exp. 176 | 4.8 | 664 | 6.6 |
| Exp. 177 | 4.9 | 654 | 6.5 |
| Exp. 178 | 4.9 | 651 | 6.5 |
| Exp. 179 | 4.9 | 653 | 6.5 |
| Exp. 180 | 4.7 | 661 | 6.6 |
| Exp. 181 | 4.8 | 667 | 6.6 |
| Exp. 182 | 4.9 | 668 | 6.6 |
| Exp. 183 | 5 | 653 | 6.5 |
| Exp. 184 | 5.2 | 623 | 6.2 |
| Exp. 185 | 5.3 | 621 | 6.2 |
| Exp. 186 | 5.1 | 618 | 6.2 |
| Exp. 187 | 5.3 | 641 | 6.4 |
| Comp. Exp. 1 | 5.7 | 600 | 6 |

As can be seen from the above results, the organic electroluminescent devices (Examples 151 to 187) employing the inventive compounds can show a higher performance as compared to a conventional organic electroluminescent device (Comparative Example 1) employing Alq3, in view of voltage and efficiency.

While a preferred embodiment of the present invention has been described, the present invention is not limited thereto. It will be understood that various changes in form and details may be made therein without departing from the scope of the present invention as defined by the following claims, and the detailed description of the invention.

The invention claimed is:

1. A compound represented by following Formula 1:

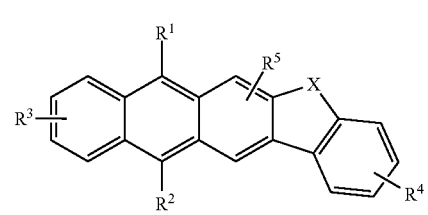

[Formula 1]

wherein in Formula 1, X is selected from the group consisting of $CR^6R^7$, $NR^6$, O, S, S(=O), S(=O)$_2$ and $SiR^6R^7$; and $R^1$ through $R^7$ are the same or different and each independently selected from the group consisting of hydrogen (H), deuterium (D), an alkyl group of $C_1$~$C_{40}$, an alkenyl group of $C_2$~$C_{40}$, an alkynyl group of $C_2$~$C_{40}$, a cycloalkyl group of $C_3$~$C_{40}$, a heterocycloalkyl group of $C_3$~$C_{40}$, an arylalkyl group of $C_6$~$C_{40}$, an alkyloxy group of $C_1$~$C_{40}$, an aryloxy group of $C_5$~$C_{40}$, an aryl group of $C_5$~$C_{40}$, a heteroaryl group of $C_5$~$C_{40}$, a substituent represented by Formula 2 below, and a substituent represented by Formula 3 below, wherein at least one of $R^1$ through $R^4$ is a substituent represented by Formula 2, or a substituent represented by Formula 3,

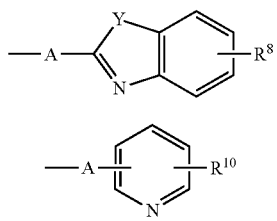

[Formula 2]

[Formula 3]

in Formulas 2 and 3, Y is selected from the group including N—$R^9$, S, and O;

$R^8$ through $R^{10}$ are the same or different and each independently selected from the group consisting of hydrogen (H), deuterium (D), an alkyl group of $C_1$~$C_{40}$, an alkenyl group of $C_2$~$C_{40}$, an alkynyl group of $C_2$~$C_{40}$, a cycloalkyl group of $C_3$~$C_{40}$, a heterocycloalkyl group of $C_3$~$C_{40}$, an arylalkyl group of $C_6$~$C_{40}$, an alkyloxy group of $C_1$~$C_{40}$, an aryloxy group of $C_5$~$C_{40}$, an aryl group of $C_5$~$C_{40}$, and a heteroaryl group of $C_5$~$C_{40}$; and A represents a single bond, an arylene group of $C_5$~$C_{40}$, or a heteroarylene group of $C_5$~$C_{40}$.

2. The compound as claimed in claim 1, wherein in $R^1$ through $R^{10}$, the alkyl group of $C_1$~$C_{40}$, the alkenyl group of $C_2$~$C_{40}$, the alkynyl group of $C_2$~$C_{40}$, the cycloalkyl group of $C_3$~$C_{40}$, the heterocycloalkyl group of $C_3$~$C_{40}$, the arylalkyl group of $C_6$~$C_{40}$, the alkyloxy group of $C_1$~$C_{40}$, the aryloxy group of $C_5$~$C_{40}$, the aryl group of $C_5$~$C_{40}$, and the heteroaryl group of $C_5$~$C_{40}$ are each independently substituted by at least one selected from the group consisting of deuterium, halogen, a nitrile group, a nitro group, an alkyl group of $C_1$~$C_{40}$, an alkenyl group of $C_2$~$C_{40}$, an alkynyl group of $C_2$~$C_{40}$, an alkoxy group of $C_1$~$C_{40}$, an amino group of $C_1$~$C_{40}$, a cycloalkyl group of $C_3$~$C_{40}$, a heterocycloalkyl group of $C_3$~$C_{40}$, an arylalkyl group of $C_6$~$C_{40}$, an aryl group of $C_5$~$C_{40}$ or a heteroaryl group of $C_5$~$C_{40}$.

3. An organic electroluminescent device comprising:
an anode;
a cathode; and
one or more organic material layers intervened between the anode and the cathode,
wherein at least one layer of the organic material layers comprises the compound represented by Formula 1 as claimed in claim 2.

4. The organic electroluminescent device as claimed in claim 3, wherein the organic material layer comprising the compound represented by Formula 1 is an electron transport layer.

5. An organic electroluminescent device comprising:
an anode;
a cathode; and
one or more organic material layers intervened between the anode and the cathode,
wherein at least one layer of the organic material layers comprises the compound represented by Formula 1 as claimed in claim 1.

6. The organic electroluminescent device as claimed in claim 5, wherein the organic material layer comprising the compound represented by Formula 1 is an electron transport layer.

* * * * *